US012714713B2

(12) United States Patent
Buck et al.

(10) Patent No.: US 12,714,713 B2
(45) Date of Patent: Aug. 25, 2026

(54) METHOD OF TREATING CANCERS WITH ALKYNE SUBSTITUTED QUINAZOLINE DERIVATIVES

(71) Applicant: Black Diamond Therapeutics, Inc., Cambridge, MA (US)

(72) Inventors: Elizabeth Buck, Huntington, NY (US); Matthew O'Connor, Massapequa Park, NY (US); Darlene Romashko, Middle Island, NY (US); Tai-An Lin, Jersey City, NJ (US); Alexander Flohr, Basel (CH); Luca Arista, Riehen (CH); Iwona Wrona, Sharon, MA (US); Matthew Lucas, Lexington, MA (US); Chris Roberts, Belmont, MA (US); Giorgio Ottaviani, Riehen (CH); Sherri Smith, South Boston, MA (US); Nigel Waters, Belmont, MA (US); David M. Epstein, Belmont, MA (US)

(73) Assignee: Black Diamond Therapeutics, Inc., Cambridge, MA (US)

( * ) Notice: Subject to any disclaimer, the term of this patent is extended or adjusted under 35 U.S.C. 154(b) by 544 days.

(21) Appl. No.: 18/034,749

(22) PCT Filed: Nov. 2, 2021

(86) PCT No.: PCT/US2021/057724

§ 371 (c)(1),
(2) Date: May 1, 2023

(87) PCT Pub. No.: WO2022/094464

PCT Pub. Date: May 5, 2022

(65) Prior Publication Data

US 2024/0075042 A1 Mar. 7, 2024

Related U.S. Application Data

(60) Provisional application No. 63/244,540, filed on Sep. 15, 2021, provisional application No. 63/237,782,
(Continued)

(51) Int. Cl.
*A61K 31/5377* (2006.01)
*A61K 31/517* (2006.01)
*A61P 35/04* (2006.01)

(52) U.S. Cl.
CPC ........ *A61K 31/5377* (2013.01); *A61K 31/517* (2013.01); *A61P 35/04* (2018.01)

(58) Field of Classification Search
CPC .... A61K 31/5377; A61K 31/517; A61P 35/04
See application file for complete search history.

(56) References Cited

U.S. PATENT DOCUMENTS 6,127,374 A 10/2000 Bridges
6,867,201 B2 3/2005 Kath et al.
(Continued)

FOREIGN PATENT DOCUMENTS

CN 1492860 A 4/2004
CN 101010304 A 8/2007
(Continued)

OTHER PUBLICATIONS

Moffitt Cancer Center ( www. moffitt.org/cancers/brain-tumor/leptomeningeal-disease/, 2025) (Year: 2025).*
(Continued)

*Primary Examiner* — Brandon J Fetterolf
(74) *Attorney, Agent, or Firm* — Fenwick & West LLP; Heidi A. Eriacher; Christine McCain

(57) ABSTRACT

The present disclosure relates to methods of treating or preventing cancer (e.g., advanced solid cancer) using Compound No. 1 or Compound No. 2:
(Continued)

(Compound No. 1)

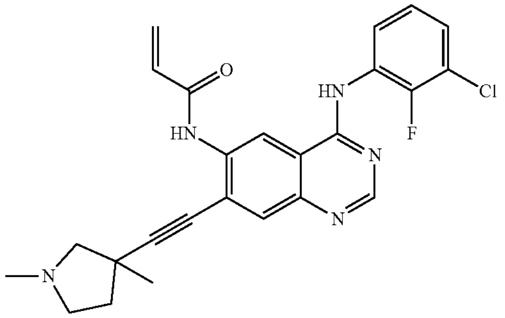

(Compound No. 2)

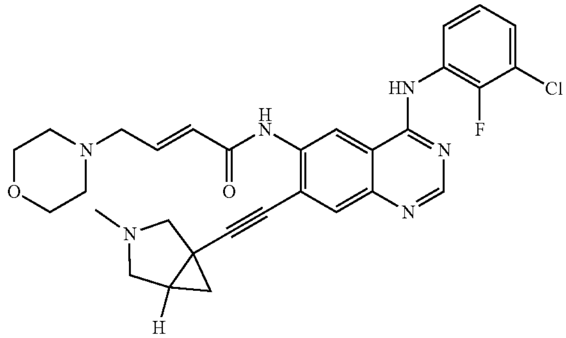

or a pharmaceutically acceptable salt thereof. The present disclosure also relates to pharmaceutical compositions and pharmaceutical kits suitable for the treatment or prevention.

20 Claims, 31 Drawing Sheets

Specification includes a Sequence Listing.

Related U.S. Application Data filed on Aug. 27, 2021, provisional application No. 63/218,717, filed on Jul. 6, 2021, provisional application No. 63/190,067, filed on May 18, 2021, provisional application No. 63/166,045, filed on Mar. 25, 2021.

(56) References Cited

U.S. PATENT DOCUMENTS

| | | | |
|---|---|---|---|
| 7,294,629 | B2 | 11/2007 | Kitano et al. |
| 8,735,409 | B2 | 5/2014 | Zhang et al. |
| 8,987,284 | B2 | 3/2015 | Shen et al. |
| 9,090,588 | B2 | 7/2015 | Shen et al. |
| 9,187,459 | B2 | 11/2015 | Shen et al. |
| 9,890,187 | B2 | 2/2018 | Odysseos et al. |
| 10,221,191 | B2 | 3/2019 | Hadari et al. |
| 10,309,966 | B2 | 6/2019 | Sibilia |
| 10,640,524 | B2 | 5/2020 | Odysseos et al. |
| 10,870,657 | B2 | 12/2020 | Hadari et al. |
| 11,034,672 | B1 | 6/2021 | Flohr et al. |
| 12,435,046 | B2 | 10/2025 | Lucas et al. |
| 2008/0200433 | A1 | 8/2008 | Suzuki et al. |
| 2010/0087482 | A1 | 4/2010 | Haber et al. |
| 2013/0035350 | A1 | 2/2013 | Zhang et al. |
| 2015/0126537 | A1 | 5/2015 | Zhang |
| 2016/0039838 | A1 | 2/2016 | Zhang et al. |
| 2019/0382382 | A1 | 12/2019 | Shen et al. |
| 2020/0299315 | A1 | 9/2020 | Shen et al. |
| 2022/0041613 | A1 | 2/2022 | Flohr et al. |
| 2022/0273665 | A1 | 9/2022 | McGovern et al. |
| 2022/0298120 | A1* | 9/2022 | Lucas et al. |
| 2022/0340523 | A1 | 10/2022 | Dakin et al. |
| 2022/0363666 | A1 | 11/2022 | Flohr et al. |

FOREIGN PATENT DOCUMENTS

| | | | |
|---|---|---|---|
| CN | 101679384 | A | 3/2010 |
| CN | 102382065 | A | 3/2012 |
| CN | 102452989 | A | 5/2012 |
| CN | 102516232 | A | 6/2012 |
| CN | 102731485 | A | 10/2012 |
| CN | 103797006 | A | 5/2014 |
| CN | 103965120 | A | 8/2014 |
| CN | 103998040 | A | 8/2014 |
| CN | 104119350 | A | 10/2014 |
| CN | 105348271 | A | 2/2016 |
| CN | 108473464 | A | 8/2018 |
| CN | 109265449 | A | 1/2019 |
| CN | 113382986 | A | 9/2021 |
| EP | 1000039 | A1 | 5/2000 |
| EP | 1249451 | A2 | 10/2002 |
| EP | 1369418 | A1 | 12/2003 |
| EP | 1000039 | B1 | 6/2004 |
| EP | 1506962 | A2 | 2/2005 |
| EP | 1792898 | A1 | 6/2007 |
| EP | 2612860 | A1 | 7/2013 |
| JP | 5155391 | B2 | 3/2013 |
| WO | WO-9630347 | A1 | 10/1996 |
| WO | WO-9738983 | A1 | 10/1997 |
| WO | WO-9906378 | A1 | 2/1999 |
| WO | WO-9909016 | A1 | 2/1999 |
| WO | WO-0044728 | A1 | 8/2000 |
| WO | WO-0047212 | A1 | 8/2000 |
| WO | WO-0078735 | A1 | 12/2000 |
| WO | WO-0177104 | A1 | 10/2001 |
| WO | WO-0218370 | A1 | 3/2002 |
| WO | WO-0250043 | A1 | 6/2002 |
| WO | WO-02066445 | A1 | 8/2002 |
| WO | WO-03045939 | A1 | 6/2003 |
| WO | WO-03089439 | A1 | 10/2003 |
| WO | WO-2004069791 | A2 | 8/2004 |
| WO | WO-2005026157 | A1 | 3/2005 |
| WO | WO-2005107758 | A1 | 11/2005 |
| WO | WO-2006025490 | A1 | 3/2006 |
| WO | WO-2007013950 | A2 | 2/2007 |
| WO | WO-2007055513 | A1 | 5/2007 |
| WO | WO-2007055514 | A1 | 5/2007 |
| WO | WO-2008020711 | A1 | 2/2008 |
| WO | WO-2008033749 | A2 | 3/2008 |
| WO | WO-2008150118 | A2 | 12/2008 |
| WO | WO-2008157500 | A1 | 12/2008 |
| WO | WO-2010036629 | A2 | 4/2010 |
| WO | WO-2012122058 | A2 | 9/2012 |
| WO | WO-2012136099 | A1 | 10/2012 |
| WO | WO-2013008217 | A1 | 1/2013 |
| WO | WO-2013013640 | A1 | 1/2013 |
| WO | WO-2013131424 | A1 | 9/2013 |
| WO | WO-2013173254 | A1 | 11/2013 |
| WO | WO-2014007951 | A2 | 1/2014 |
| WO | WO-2014071824 | A1 | 5/2014 |
| WO | WO-2014177038 | A1 | 11/2014 |
| WO | WO-2015043515 | A1 | 4/2015 |
| WO | WO-2015054572 | A1 | 4/2015 |
| WO | WO-2016023217 | A1 | 2/2016 |
| WO | WO-2016055982 | A1 | 4/2016 |
| WO | WO-2016105582 | A1 | 6/2016 |
| WO | WO-2016203406 | A1 | 12/2016 |
| WO | WO-2017055859 | A1 | 4/2017 |
| WO | WO-2020068867 | A1 | 4/2020 |
| WO | WO-2020068873 | A1 | 4/2020 |
| WO | WO-2021030711 | A1 | 2/2021 |
| WO | WO-2021154997 | A1 | 8/2021 |
| WO | WO-2021195206 | A1 | 9/2021 |
| WO | WO-2021213800 | A1 | 10/2021 |
| WO | WO-2022040377 | A1 | 2/2022 |

(56) References Cited

FOREIGN PATENT DOCUMENTS

| | | |
|---|---|---|
| WO | WO-2022076671 A1 | 4/2022 |
| WO | WO-2022094464 A1 | 5/2022 |
| WO | WO-2023049168 A1 | 3/2023 |

OTHER PUBLICATIONS

Thomas and Ramirez (Ochsner Journal 2017; 17: 362-378) (Year: 2017).*
Cominelli et al. (JNCI J Natl Cancer Inst (2015); 107(5): djv041) (Year: 2015).*
Limam et al. (Ann Biol Clin 2019; 77(3): 307-317) (Year: 2019).*
Sattler, M. et al., "A Closer Look at EGFR Inhibitor Resistance in Non-Small Cell Lung Cancer through the Lens of Precision Medicine," J Clin Med. Mar. 1, 2023;12(5):1936, 13 pages, doi: 10.3390/jcm12051936.
Wang, D.D. et al., "Personalized prediction of EGFR mutation-induced drug resistance in lung cancer," Scientific Reports, 2013;3:2855, DOI: 10.1038/srep02855, 8 pages.
Argiris, A et al., "Phase III Randomized, Placebo-Controlled Trial of Docetaxel With or Without Gefitinib in Recurrent or Metastatic Head and Neck Cancer: An Eastern Cooperative Oncology Group Trial," Journal of Clinical Oncology, 31(11):1405-1414 (2013).
Asadollahi-Baboli, M., "In silica evaluation, molecular docking and QSAR analysis of quinazoline-based EGFR-T790M inhibitors," Mol Divers, 20:729-739 (2016).
Blair et al., "Structure-guided development of affinity probes for tyrosine kinases using chemical genetics," Nature Chemical Biology, Apr. 2007, 3:229-238.
Caira, M. R., "Crystalline Polymorphism of Organic Compounds", Topics in Current Chemistry (Jan. 1, 1998); 198:163-208.
Carmi, C. et al. "Irreversible Inhibition of Epidermal Growth Factor Receptor Activity by 3-Aminopropanamides," J. Med. Chem., Jan. 26, 2012, 55:2251-2264 (including Supporting Information, 25 pages total).
CAS Registry No. 1012054-59-9, dated Apr. 4, 2008, 1 page.
CAS Registry No. 1092364-38-9, dated Dec. 31, 2008, 1 page.
CAS Registry No. 1110813-31-4, dated Feb. 23, 2009, 1 page.
CAS Registry No. 1131863-89-2, dated Apr. 3, 2009, 1 page.
CAS Registry No. 1197953-54-0, dated Dec. 17, 2009, 1 page.
CAS Registry No. 1213269-23-8, dated Mar. 23, 2010, 1 page.
CAS Registry No. 1214265-56-1, dated Mar. 24, 2010, 1 page.
CAS Registry No. 1214265-57-2, dated Mar. 24, 2010, 1 page.
CAS Registry No. 1374640-70-6, dated May 29, 2012, 1 page.
CAS Registry No. 1398833-56-1, dated Oct. 3, 2012, 1 page.
CAS Registry No. 1421373-65-0, dated Feb. 19, 2013, 1 page.
CAS Registry No. 183319-69-9, dated Nov. 22, 1996, 1 page.
CAS Registry No. 184475-35-2, dated Dec. 26, 1996, 1 page.
CAS Registry No. 187724-61-4, dated Mar. 28, 1997, 1 page.
CAS Registry No. 194423-15-9, dated Sep. 24, 1997, 1 page.
CAS Registry No. 196612-93-8, dated Oct. 31, 1997, 1 page.
CAS Registry No. 212141-54-3, dated Oct. 4, 1998, 1 page.
CAS Registry No. 231277-92-2, dated Aug. 7, 1999, 1 page.
CAS Registry No. 257933-82-7, dated Mar. 3, 2000, 1 page.
CAS Registry No. 267243-28-7, dated May 30, 2000, 1 page.
CAS Registry No. 439081-18-2, dated Jul. 17, 2002, 1 page.
CAS Registry No. 443913-73-3, dated Aug. 14, 2002, 1 page.
CAS Registry No. 451493-31-5, dated Sep. 16, 2002, 1 page.
CAS Registry No. 497839-62-0, dated Mar. 11, 2003, 1 page.
CAS Registry No. 610798-31-7, dated Oct. 30, 2003, 1 page.
CAS Registry No. 692737-80-7, dated Jun. 14, 2004, 1 page.
CAS Registry No. 698387-09-6, dated Jun. 24, 2004, 1 page.
CAS Registry No. 714971-09-2, dated Jul. 23, 2004, 1 page.
CAS Registry No. 781613-23-8, dated Nov. 16, 2004, 1 page.
CAS Registry No. 848133-17-5, dated Apr. 8, 2005, 1 page.
CAS Registry No. 848942-61-0, dated Apr. 21, 2005, 1 page.
CAS Registry No. 871026-44-7, dated Jan. 3, 2006, 1 page.
CAS Registry No. 897383-62-9, dated Jul. 28, 2006, 1 page.
CAS Registry No. 934660-93-2, dated May 13, 2007, 1 page.
Dermer, G.B., "Another Anniversary for the War on Cancer," Bio/Technology, 12:320, 1 page (Mar. 1994).
Freshney R.I., et al., "Culture of Animal Cells," A Manual of Basic Technique, 1983, Alan R. Liss, Inc., New York, p. 4 and pp. 129-133 (9 total pages).
Golub, T. R., et al., "Molecular classification of cancer: class discovery and class prediction by gene expression monitoring", Science (1999); 286: 531-537.
Martins, R. G. et al., "Cisplatin and Radiotherapy With or Without Erlotinib in Locally Advanced Squamous Cell Carcinoma of the Head and Neck: A Randomized Phase II Trial," Journal of Clinical Oncology, 31(11):1415-1421 (2013).
Peereboom, D. M. et al., "Phase II trial of erlotinib with temozolomide and radiation in patients with newly diagnosed glioblastoma multiforme," J Neurooncol, 98:93-99 (2010).
Petrylak, D. P. et al., "Results of the Southwest Oncology Group phase II evaluation (study S0031) of ZD1839 for advanced transitional cell carcinoma of the urothelium," Southwest Oncology Group, 105:317-321 (2009); doi:10.1111/j.1464-41OX.2009.08799.x.
Philips, G. K. et al., "A phase II trial of cisplatin (C), gemcitabine (G) and gefitinib for advanced urothelial tract carcinoma: results of Cancer and Leukemia Group B (CALGB) 90102," Annals of Oncology, 20:1074-1079 (2009).
Reardon, D.A. et al., "Phase I/randomized phase II study of afatinib, an irreversible ErbB family blocker, with or without protracted temozolomide in adults with recurrent glioblastoma," Neuro-Oncology, Advance Access published Aug. 19, 2014, 10 pages; final publication in Neuro Oncol., Mar. 2015;17(3):430-9. doi: 10.1093/neuonc/nou160.
Shen, W. et al. "A41 EO1001: A First-in-Class Irreversible Pan-ErbB Inhibitor with Excellent Brain Penetration," Journal of Thoracic Oncology, 15(2 Suppl):S26, Abstract A41 (Feb. 2020).
Shen, W. et al. "NT113, a potent and selective pan-ErbB inhibitor, is efficacious in vivo and has high brain penetrance," [abstract]. In: Proceedings of the 104th Annual Meeting of the American Association for Cancer Research; Apr. 6-10, 2013; Washington, DC. Philadelphia (PA): Aacr; Cancer Res., 73(8 Suppl):Abstract nr 2089 (2013); doi:10.1158/1538-7445.AM2013-2089.
Simone, J. V. (1996) "Introduction" in Cecil Textbook of Medicine. 20th Ed., vol. I . J. Claude Bennet and F. Plum (Eds.) W.B. Sauders Co.; pp. 1004-1010.
Van Den Bent, M. J. et al., "Randomized Phase II Trial of Erlotinib Versus Temozolomide or Carmustine in Recurrent Glioblastoma: EORTC Brain Tumor Group Study 26034," J Clin Oncol, 27:1268-1274 (2009).
Yin, D. et al. "Studying the Conformation of a Receptor Tyrosine Kinase in Solution by Inhibitor-Based Spin Labeling," Angew Chem Int Ed Engl., 56(29):8417-8421, with Supporting Information, 24 pages (Jul. 10, 2017). doi: 10.1002/anie.201703154. Epub Jun. 19, 2017.
Yoshida, Y. et al. "NT113, a pan-ERBB Inhibitor with High Brain Penetrance, Inhibits the Growth of Glioblastoma Xenografts with EGFR Amplification," Mol. Cancer Ther., Dec. 2014, 13(12):2919-29.

* cited by examiner

Normalized BLI
250
200
150
100
50
40
30
20
10
0
5
10
15
20
25
30
Days after Implantation
Vehicle Control
Compound No. 1A, 5 mg/kg
Compound No. 1A, 15 mg/kg
Compound No. 1A, 50 mg/kg Mean PO (15 mg/kg)
Mean IV bolus (1 mg/kg)
Concentration (ng/mL)
Time (h)
10000
1000
100
10
1
0
4
8
12
16
20
24

FIG. 19B
Nomalized pEGFR (p1068)
2.0
1.5
1.0
0.5
0.0
Control
4hr
8hr
10hr
12hr
24hr

SEQUENCE LISTING

```
<160> NUMBER OF SEQ ID NOS: 8

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190
```

-continued

```
Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
```

-continued

```
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035
```

```
Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210


<210> SEQ ID NO 2
<211> LENGTH: 1255
<212> TYPE: PRT
<213> ORGANISM: Homo sapiens

<400> SEQUENCE: 2

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
```

-continued

```
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605
```

-continued

```
Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020
```

-continued

```
Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val Pro Val
    1250                1255


<210> SEQ ID NO 3
<211> LENGTH: 1225
<212> TYPE: PRT
<213> ORGANISM: Homo sapiens

<400> SEQUENCE: 3

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125
```

-continued

```
Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540
```

-continued

```
Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
```

-continued

```
            965                 970                 975

Ser Leu Leu Glu Asp Asp Asp Met Gly Asp Leu Val Asp Ala Glu Glu
        980                 985                 990

Tyr Leu Val Pro Gln Gln Gly Phe  Phe Cys Pro Asp Pro  Ala Pro Gly
    995                 1000                1005

Ala Gly  Gly Met Val His His  Arg His Arg Ser Ser  Ser Thr Arg
    1010                1015                1020

Ser Gly  Gly Gly Asp Leu Thr  Leu Gly Leu Glu Pro  Ser Glu Glu
    1025                1030                1035

Glu Ala  Pro Arg Ser Pro Leu  Ala Pro Ser Glu Gly  Ala Gly Ser
    1040                1045                1050

Asp Val  Phe Asp Gly Asp Leu  Gly Met Gly Ala Ala  Lys Gly Leu
    1055                1060                1065

Gln Ser  Leu Pro Thr His Asp  Pro Ser Pro Leu Gln  Arg Tyr Ser
    1070                1075                1080

Glu Asp  Pro Thr Val Pro Leu  Pro Ser Glu Thr Asp  Gly Tyr Val
    1085                1090                1095

Ala Pro  Leu Thr Cys Ser Pro  Gln Pro Glu Tyr Val  Asn Gln Pro
    1100                1105                1110

Asp Val  Arg Pro Gln Pro Pro  Ser Pro Arg Glu Gly  Pro Leu Pro
    1115                1120                1125

Ala Ala  Arg Pro Ala Gly Ala  Thr Leu Glu Arg Pro  Lys Thr Leu
    1130                1135                1140

Ser Pro  Gly Lys Asn Gly Val  Val Lys Asp Val Phe  Ala Phe Gly
    1145                1150                1155

Gly Ala  Val Glu Asn Pro Glu  Tyr Leu Thr Pro Gln  Gly Gly Ala
    1160                1165                1170

Ala Pro  Gln Pro His Pro Pro  Pro Ala Phe Ser Pro  Ala Phe Asp
    1175                1180                1185

Asn Leu  Tyr Tyr Trp Asp Gln  Asp Pro Pro Glu Arg  Gly Ala Pro
    1190                1195                1200

Pro Ser  Thr Phe Lys Gly Thr  Pro Thr Ala Glu Asn  Pro Glu Tyr
    1205                1210                1215

Leu Gly  Leu Asp Val Pro Val
    1220                1225


<210> SEQ ID NO 4
<211> LENGTH: 1240
<212> TYPE: PRT
<213> ORGANISM: Homo sapiens

<400> SEQUENCE: 4

Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95
```

-continued

```
Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
```

```
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
    690                 695                 700

Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
            740                 745                 750

Leu Asp Glu Ala Tyr Val Met Ala Gly Val Gly Ser Pro Tyr Val Ser
        755                 760                 765

Arg Leu Leu Gly Ile Cys Leu Thr Ser Thr Val Gln Leu Val Thr Gln
    770                 775                 780

Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
        835                 840                 845

Phe Gly Leu Ala Arg Leu Leu Asp Ile Asp Glu Thr Glu Tyr His Ala
    850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
        915                 920                 925

Pro Pro Ile Cys Thr Ile Asp Val Tyr Met Ile Met Val Lys Cys Trp
    930                 935                 940
```

Met Ile Asp Ser Glu Cys Arg Pro Arg Phe Arg Glu Leu Val Ser Glu
945 950 955 960

Phe Ser Arg Met Ala Arg Asp Pro Gln Arg Phe Val Val Ile Gln Asn
965 970 975

Glu Asp Leu Gly Pro Ala Ser Pro Leu Asp Ser Thr Phe Tyr Arg Ser
980 985 990

Leu Leu Glu Asp Asp Asp Met Gly Asp Leu Val Asp Ala Glu Glu Tyr
995 1000 1005

Leu Val Pro Gln Gln Gly Phe Phe Cys Pro Asp Pro Ala Pro Gly
1010 1015 1020

Ala Gly Gly Met Val His His Arg His Arg Ser Ser Ser Thr Arg
1025 1030 1035

Ser Gly Gly Gly Asp Leu Thr Leu Gly Leu Glu Pro Ser Glu Glu
1040 1045 1050

Glu Ala Pro Arg Ser Pro Leu Ala Pro Ser Glu Gly Ala Gly Ser
1055 1060 1065

Asp Val Phe Asp Gly Asp Leu Gly Met Gly Ala Ala Lys Gly Leu
1070 1075 1080

Gln Ser Leu Pro Thr His Asp Pro Ser Pro Leu Gln Arg Tyr Ser
1085 1090 1095

Glu Asp Pro Thr Val Pro Leu Pro Ser Glu Thr Asp Gly Tyr Val
1100 1105 1110

Ala Pro Leu Thr Cys Ser Pro Gln Pro Glu Tyr Val Asn Gln Pro
1115 1120 1125

Asp Val Arg Pro Gln Pro Pro Ser Pro Arg Glu Gly Pro Leu Pro
1130 1135 1140

Ala Ala Arg Pro Ala Gly Ala Thr Leu Glu Arg Pro Lys Thr Leu
1145 1150 1155

Ser Pro Gly Lys Asn Gly Val Val Lys Asp Val Phe Ala Phe Gly
1160 1165 1170

Gly Ala Val Glu Asn Pro Glu Tyr Leu Thr Pro Gln Gly Gly Ala
1175 1180 1185

Ala Pro Gln Pro His Pro Pro Pro Ala Phe Ser Pro Ala Phe Asp
1190 1195 1200

Asn Leu Tyr Tyr Trp Asp Gln Asp Pro Pro Glu Arg Gly Ala Pro
1205 1210 1215

Pro Ser Thr Phe Lys Gly Thr Pro Thr Ala Glu Asn Pro Glu Tyr
1220 1225 1230

Leu Gly Leu Asp Val Pro Val
1235 1240

<210> SEQ ID NO 5
<211> LENGTH: 1055
<212> TYPE: PRT
<213> ORGANISM: Homo sapiens

<400> SEQUENCE: 5

Met Glu Leu Ala Ala Leu Cys Arg Trp Gly Leu Leu Leu Ala Leu Leu
1 5 10 15

Pro Pro Gly Ala Ala Ser Thr Gln Val Cys Thr Gly Thr Asp Met Lys
20 25 30

Leu Arg Leu Pro Ala Ser Pro Glu Thr His Leu Asp Met Leu Arg His
35 40 45

Leu Tyr Gln Gly Cys Gln Val Val Gln Gly Asn Leu Glu Leu Thr Tyr

-continued

```
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480
```

-continued

```
Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895
```

```
Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Asn Met
    1055


<210> SEQ ID NO 6
<211> LENGTH: 603
<212> TYPE: PRT
<213> ORGANISM: Homo sapiens

<400> SEQUENCE: 6

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205
```

```
Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525
```

-continued

```
His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser
        595                 600


<210> SEQ ID NO 7
<211> LENGTH: 21
<212> TYPE: PRT
<213> ORGANISM: Homo sapiens

<400> SEQUENCE: 7

Lys Glu Ile Leu Asp Glu Ala Tyr Val Met Ala Ser Val Asp Asn Pro
1               5                   10                  15

His Val Cys Ala Arg
            20


<210> SEQ ID NO 8
<211> LENGTH: 20
<212> TYPE: PRT
<213> ORGANISM: Homo sapiens

<400> SEQUENCE: 8

Lys Glu Ile Leu Asp Glu Ala Tyr Val Met Ala Gly Val Gly Ser Pro
1               5                   10                  15

Tyr Val Ser Arg
            20
```

METHOD OF TREATING CANCERS WITH ALKYNE SUBSTITUTED QUINAZOLINE DERIVATIVES

RELATED APPLICATIONS

This application is a U.S. National Phase application, filed under U.S.C. § 371, of International Application No. PCT/US2021/057724, filed Nov. 2, 2021, which claims priority to, and the benefit of, U.S. Provisional Application No. 63/244,540, filed Sep. 15, 2021, U.S. Provisional Application No. 63/237,782, filed Aug. 27, 2021, U.S. Provisional Application No. 63/218,717, filed Jul. 6, 2021, U.S. Provisional Application No. 63/190,067, filed May 18, 2021, U.S. Provisional Application No. 63/166,045, filed Mar. 25, 2021, and U.S. Provisional Application No. 63/108,645, filed Nov. 2, 2020, the entire contents of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 17, 2023, is named "ASET-023_NO1US_SeqList_ST25.txt" and is about 57,948 bytes in size.

BACKGROUND

Mutations affecting either the intracellular catalytic domain or extracellular ligand binding domain of an ErbB receptor can generate oncogenic activity (the ErbB protein family consists of 4 members including ErbB-1, also named epidermal growth factor receptor (EGFR) and Erb-2, also named HER2 in humans). ErbB inhibitors are a known treatment for a number of cancers. However, not every patient responds satisfactorily to this treatment. Thus, there is a long-felt need in the art for new therapies that are able to address the variable responsiveness of cancer patients to known therapies. The present disclosure provides compositions and methods for preventing or treating cancer in patients with these oncogenic mutations without the variable responsiveness observed when patients having these ErbB mutants are treated using the existing standard of care.

SUMMARY

In some aspects, the present disclosure provides a method of treating or preventing cancer in a subject in need thereof, comprising administering to the subject a pharmaceutically effective amount of Compound No. 1 or a pharmaceutically acceptable salt thereof.

In some aspects, the present disclosure provides Compound No. 1, Compound No. 2, or a pharmaceutically acceptable salt thereof for treating or preventing cancer in a subject in need thereof.

In some aspects, the present disclosure provides use of Compound No. 1, Compound No. 2, or a pharmaceutically acceptable salt thereof, in the manufacture of a medicament for treating or preventing cancer in a subject in need thereof.

In some aspects, the present disclosure provides a pharmaceutical composition for treating or preventing cancer, comprising Compound No. 1, Compound No. 2, or a pharmaceutically acceptable salt thereof.

In some aspects, the present disclosure provides a pharmaceutical kit for treating or preventing cancer, comprising Compound No. 1, Compound No. 2, or a pharmaceutically acceptable salt thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTIONS OF FIGURES

DETAILED DESCRIPTION

Figure 1:
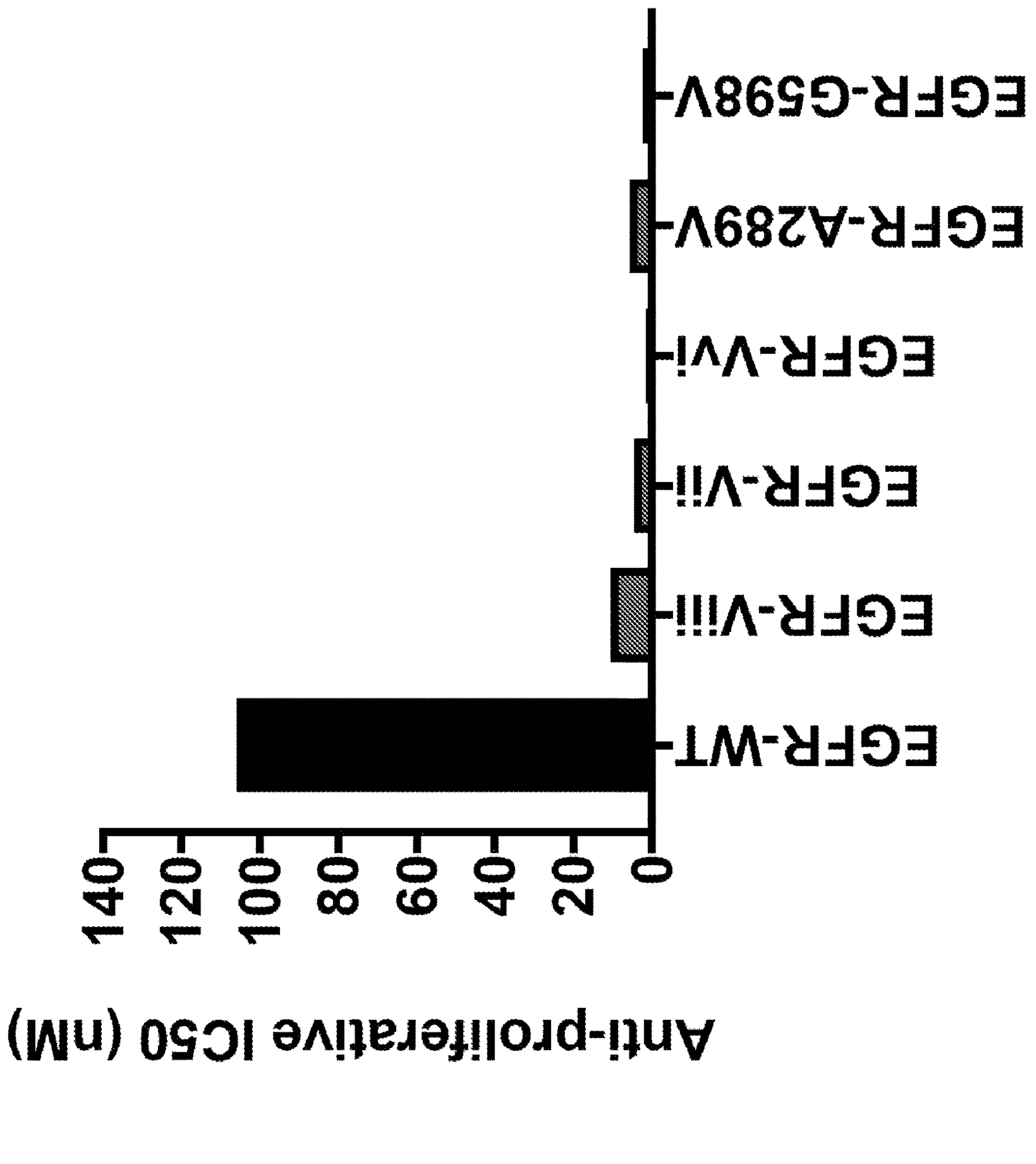
FIG. 1 is a graph showing the anti-proliferative $IC_{50}$ values for Compound No. 1A in EGFR-WT, EGFR-Viii, EGFR-Vii, EGFR-Vvi, EGFR-A289V, and EGFR-G598V.

It is understood that the term “Compound No. 1,” as used herein, refers to a compound having the following structure:

(Compound No. 1)

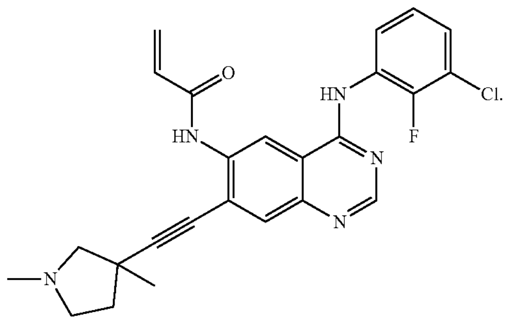

It is understood that the term “Compound No. 1A,” as used herein, refers to a compound having the following structure:

(Compound No. 1A)

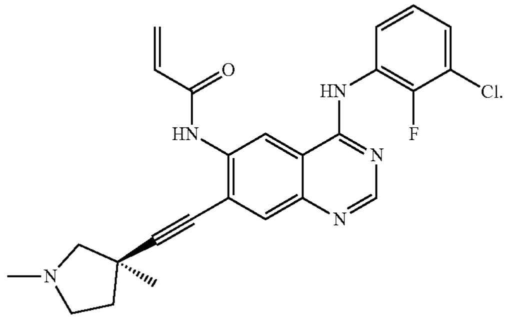

It is understood that the term “Compound No. 1B,” as used herein, refers to a compound having the following structure:

(Compound No. 1B)

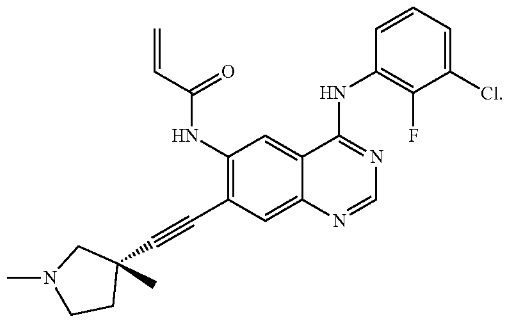

It is understood that the term "Compound No. 2," as used herein, refers to a compound having the following structure:

(Compound No. 2)

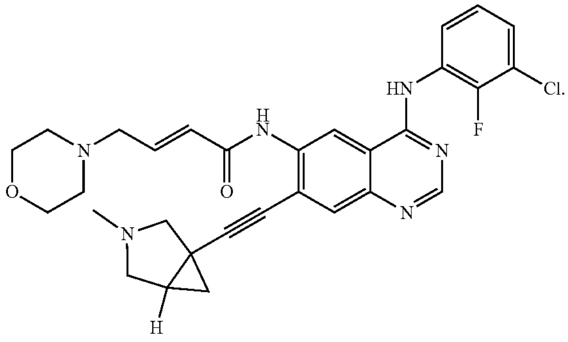

It is understood that the term "Compound No. 2A," as used herein, refers to a compound having the following structure:

(Compound No. 2A)

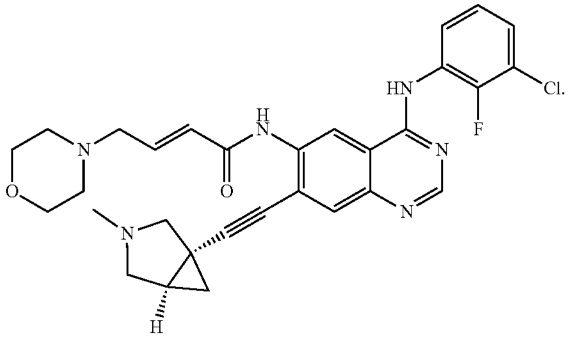

It is understood that the term "Compound No. 2B," as used herein, refers to a compound having the following structure:

(Compound No. 2B)

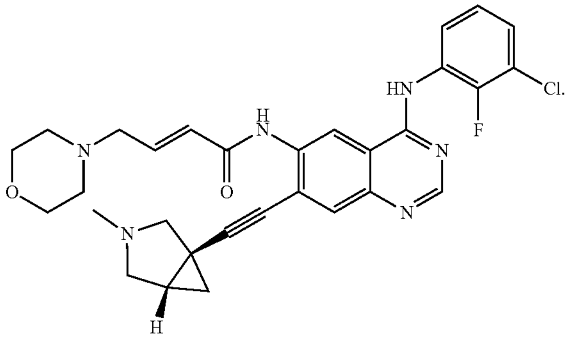

The present disclosure relates to compounds useful as inhibitors of receptor tyrosine kinases (RTK), in particular oncogenic mutants of ErbB-receptors. In some embodiments of the invention, oncogenic mutants of ErbB-receptors are also allosteric mutants of ErbB-receptors. In some embodiments, allosteric mutants may comprise or consist of an ErbB receptor variant having a mutation in a sequence outside of an ATP-binding site. In some embodiments, allosteric mutants may comprise or consist of an ErbB receptor variant having a mutation in a sequence within one or more of exon 18, exon 19, exon 20 or a C1-C2 extracellular dimerization interface.

Mutations affecting either the intracellular catalytic domain or extracellular ligand binding domain of an ErbB receptor can generate oncogenic activity (the ErbB protein family consists of 4 members including ErbB-1, also named epidermal growth factor receptor (EGFR) and Erb-2, also named HER2 in humans). Extracellular mutants of ErbB receptors in cancer, including EGFR-Viii (also EGFR-V3) and HER2-S310F, are constitutively activated in the absence of ligand, exhibit sustained signaling that is resistant to downregulation, and are both transforming and tumorigenic (Nishikawa, Ji et al. 1994, 2013, Francis, Zhang et al. 2014). Their expression is associated with metastasis and with poor long term overall survival.

In non-small cell lung cancer (NSCLC), which accounts for approximately 85% of lung cancer cases worldwide, NSCLC harboring EGFR mutations constitute 10-20% of all lung cancer cases in Europe and North America, and up to 50% of those in Asia. Uncommon EGFR mutations, of which EGFR-G719X, EGFR-S768I, EGFR-L861Q are amongst the most frequent, account for 10-20% of EGFR mutations in NSCLC. The common Exon19del and L858R mutations, that account for 80-90% of EGFR mutations in NSCLC, respond to current generation EGFR inhibitors, but resistance invariably emerges. For example, the exon19del combined with C797S mutation (EGFR-exon19del+C797S) and the EGFR-L858R+C797S mutations impart resistance to first line treatment with current generation irreversible inhibitors (e.g., osimertinib or lazertinib).

In glioblastoma (also glioblastoma multiforme or GBM), EGFR-Viii is expressed by 20% of tumors (Sugawa, Ekstrand et al. 1990, Brennan, Verhaak et al. 2013). Expression of EGFR-Viii in GBM tends to be mutually exclusive with expression of other RTK oncogenes, which are co-expressed with EGFR variants in only 7% of GBM tumors (Furnari, Cloughesy et al. 2015). These data demonstrate how EGFR-Viii in GBM has a dominant and mutually exclusive expression pattern compared with other oncogenic drivers. EGFR-Viii is also expressed by approximately 30% of SCCHN tumors (Sok, Coppelli et al. 2006, Keller, Shroyer et al. 2010, Wheeler, Suzuki et al. 2010, Tinhofer, Klinghammer et al. 2011, Wheeler, Egloff et al. 2015) and 10% of squamous NSCLC (Ji, Zhao et al. 2006, Sasaki, Kawano et al. 2007), and is associated with resistance to current therapeutics including the anti-EGFR antibody cetuximab (Sok, Coppelli et al. 2006, Tinhofer, Klinghammer et al. 2011). Normal tissues do not express this oncogenic receptor variants.

RNA sequencing data has revealed that EGFR-Viii is just one of several aberrantly spliced variants of EGFR expressed in GBM tumors. Two others result in truncation of exons 12-13 (EGFR-Vvi) and 14-15 (EGFR-Vii). Like EGFR-Viii, EGFR-Vii is both transforming and tumorigenic. In addition to splice variants, GBM tumors also express a collection of EGFR point mutations including C620Y, A289V and G598V, which are transforming and tumorigenic.

HER2-S310F is the most common mutation of HER2 expressed in human tumors, expressed by approximately 0.5% of all tumors. HER2-S310F expression is mutually exclusive with expression of HER2 amplification. HER2-S310F is highly oncogenic, transforming BaF3 cells (a murine interleukin-3 (IL-3) dependent pro-B cell line) to IL-3 independence and promoting tumor growth in vivo.

Short insertions of within Exon 20 of EGFR and HER2 are expressed by lung adenocarcinoma tumors and other tumor groups. ErbB Exon 20 insertion mutants are expressed by 4-5% of lung adenocarcinoma tumors. Examples include HER2-YVMA, EGFR-SVD, and EGFR-NPH. These ErbB Exon 20 insertion mutants are highly oncogenic, transforming BaF3 cells to IL-3 independence and promoting tumor growth in vivo.

ErbB inhibitors are a known treatment for a number of cancers. However, not every patient is responsive satisfactorily to this treatment. Thus, there is a long-felt need in the art for new therapies that are able to address the variable responsiveness of cancer patients to known therapies. The present invention is able to overcome some of these drawbacks of the standard of care, as it existed prior to the development of the compositions and methods disclosed herein.

Paradoxic ErbB Receptor Activation

Although the mechanisms described herein apply to any form of cancer in which these EGFR variants of the disclosure are expressed, the prevalence of these variants in glioblastoma (GBM) are provide by way of example. Other cancers expressing the EGFR variants of the disclosure include, but are not limited to, solid cancers, epithelial cancers and/or cancers of epithelial origin, bladder cancer, breast cancer, cervical cancer, colorectal cancer, endometrial cancer, gastric cancer, glioblastoma (GBM), head and neck cancer, lung cancer, and non-small cell lung cancer (NSCLC).

In GBM tumors EGFR is frequently the target of genomic mutations and alternative splicing events that result in alteration of the extracellular dimer interface. Many tumors express more than one aberrant isoform. The disclosure provides the mechanism of activation for the most commonly occurring variants, EGFR-Viii, EGFR-Vii, EGFR-Vvi, EGFR-G598V and EGFR-A289V. Although each isoform/point mutant is the result of a distinct ectodomain alteration, all are activated by a common mechanism involving covalent ligand-independent dimerization.

AMG-595 (Amgen) is an EGFR-Viii isoform selective antibody that has no activity against wild type EGFR or other splice-activated variants. Rindopepimut (Celldex) is a vaccine the produces an immunological response selectively against tumor cells expressing EGFR-Viii but not wild type EGFR or other splice-activated isoforms. Other EGFR isoforms expressed in GBM tumors (EGFR-Vii and EGFR-Vvi) are constitutively active covalent receptors and their expression may limit the breadth and duration of treatment benefit for an ErbB inhibitor that is selective only for EGFR-Viii. Therefore, it may be useful to exclude patients whose tumors express EGFR-Vii, EGFR-Vvi, or EGFR ectodomain point mutants from treatment with an EGFR-Viii selective therapy.

The heterogenenic expression pattern for multiple ectodomain variants of ErbB receptors in tumors indicates that a small molecule inhibitor that inhibits all variants is preferred. The family of covalently-activated EGFR isoforms responds very differently to small molecule ErbB inhibitors compared to EGFR catalytic domain mutations observed in NSCLC. Importantly, Type I inhibitors, including erlotinib, all induce the formation of covalent EGFR dimers and increase EGFR phosphorylation at sub-saturating concentrations, an activity that is further enhanced when ErbB inhibitor is washed away. This manifests in paradoxical activation of proliferation at sub-saturating concentrations.

The discovery of paradoxical activation of proliferation at sub-saturating concentrations of Type I ErbB inhibitors is further demonstrated for a series of extracellular variants of HER2, prevalent in a number of cancers including breast and bladder. All variants existed as covalently activated receptors, and levels of covalent dimers increased following treatment with Type I inhibitors including sapitinib and afatinib. As with covalently-activated EGFR variants, sub-saturating doses of Type I inhibitors paradoxically increased phosphorylation of HER2 variants, increasing the proliferation of cells expressing them.

In contrast to Type I inhibitors, the disclosure demonstrates that Non-Type I (e.g. Type II) inhibitors including neratinib are devoid of paradoxical activation for cells expressing ErbB ectodomain variants. Neratinib is found to exemplify a preferred molecule that is both potent and selective for each member of the covalently-activated EGFR family versus wild type EGFR.

Collectively, the disclosure provides a structure/functional relationship for predicting how structural variations affecting receptor regions distal to the active site can confer dramatically different responses to small molecule active site inhibitors. The discovery described herein of paradoxical activation of covalently-activated ErbB receptor variants by Type I inhibitors has important clinical implications. The data of the disclosure provide a mechanistic explanation for the failed clinical studies for Type I inhibitors in tumor types where expression of covalently-activated ErbB receptors is prevalent. This includes erlotinib and gefitinib in GBM tumors, erlotinib in SCCHN tumors, and sapitinib in breast tumors.

Glioblastoma

Glioblastoma (GBM), grade IV astrocytoma, is the most common form of brain cancer. The outcome for this disease is dismal. Surgery followed by a therapeutic regimen of radiation and temozolomide is standard of care, however this produces a median overall survival (OS) of only 14.6 months and few patients survive for five years. There has been little progress made in extending survival for GBM patients over the past decade. Although bevacizumab showed an improved progression free survival benefit in the recurrent setting, the addition of bevacizumab to standard of care therapy in the front-line setting did not result in an OS benefit.

EGFR is the most frequently altered oncogene in GBM. In addition to EGFR gene amplification, many tumors express variants generated by aberrant splicing or genomic mutation. The first recognized variant is EGFR-Viii, resulting from truncation of exons 2-7 and expressed by approximately 20% of GBM tumors. EGFR-Viii is oncogenic. EGFR-Viii is constitutively activated in the absence of EGF ligand, exhibiting sustained signaling that is resistant to downregulation. Therefore, EGFR-Viii is both transforming and tumorigenic. Expression of EGFR-Viii is associated with poor long term overall survival in GBM.

RNA sequencing data has revealed that EGFR-Viii is just one of several aberrantly spliced variants of EGFR expressed in GBM tumors. Two others result in truncation of exons 12-13 (EGFR-Vvi and 14-15 (EGFR-Vii). Like EGFR-Viii, EGFR-Vii is both transforming and tumorigenic. In addition to splice variants, GBM tumors also express a collection of EGFR point mutations including C620Y, A289V and G598V, which are transforming and tumorigenic. The complex landscape of EGFR alterations in GBM is further compounded by the observation that many tumors express more than one receptor variant.

Because the expression of multiple EGFR variants in GBM gives rise to transforming and tumorigenic activity and because EGFR is the most frequently altered oncogene present in GBM tumors, EGFR is an especially attractive target for small molecule ErbB inhibitors. Following the success for small molecule EGFR therapeutics against NSCLC tumors harboring activating mutations in EGFR (erlotinib, gefitinib, and afatinib), these drugs were tested in GBM. Despite intense clinical investigation of this group of ErbB inhibitors in GBM, involving >30 clinical trials and >1500 patients, all failed to produce any benefit, even for those tumors that expressed EGFR-Viii. Strikingly, some evidence suggests that erlotinib promoted disease progression. A phase 2 study evaluating erlotinib in combination with radiation and temozolomide showed median PFS (mPFS) and median OS (mOS) of 2.8 months and 8.6 months, as compared to 6.9 months and 14.6 months for patients receiving radiation and temozolomide alone. Another randomized phase II trial with erlotinib showed that patients who received erlotinib, including those whose tumors expressed EGFR-Viii, progressed more poorly as compared to those patients who received standard of care therapy. The clinical failures for ErbB inhibitors such as erlotinib in GBM tumors has cast doubt on the role of EGFR as a driver of tumor growth in GBM and led to inquiry as to why ErbB inhibitors that were so effective in treating EGFR mutations in lung cancer were so ineffective in treating EGFR variants in GBM.

A distinctive feature for the EGFR variants expressed in GBM is their location within the extracellular domain. This is in contrast to activating mutations of EGFR found in lung cancer, which often reside in the intracellular catalytic domain. EGFR is composed of four extracellular domains (two ligand binding domains and two cysteine rich regions), a transmembrane domain, and an intracellular catalytic domain. Ligand binding promotes dimerization of the extracellular cysteine rich domains (CR1 and CR2), an event that confers dimerization of the intracellular domain and activation of receptor catalytic activity. Nearly all EGFR splicing events and mutations in GBM affect the extracellular region, specifically two cysteine rich regions (CR1 and CR2) that form the extracellular dimer interface. The CR regions contain >40 cysteine residues, all of which form intramolecular disulfide bonds. In EGFR-Viii, truncation of exons 2-7 results in partial loss of sequence encoding the CR1 region. A consequence is loss of one cysteine from the Cys295-Cys307 pair, leaving Cys307 as a free unpaired cysteine. For EGFR-Viii, this cysteine can form an intermolecular disulfide bond with another EGFR monomer to drive a covalently dimerized and constitutively activated receptor. Mutation of Cysteine 307 to a Serine (C307S) prevents the formation of covalently dimerized EGFR-Viii and is inactive.

Although several recent preclinical studies have suggested that EGFR kinase inhibitors such as erlotinib are quite ineffective at inhibiting EGFR-Viii, there has been no mechanism proposed for this effect. There is also a lack in current understanding for the mechanism responsible for activation of other ectodomain variants in GBM, including EGFR-Vii and EGFR-A289V. The disclosure provides a mechanism of receptor activation and impact on ErbB inhibitor activity for a group of four of the most common ectodomain variants in GBM, EGFR-Viii, EGFR-Vii, EGFR-Vvi, EGFR-G598V and EGFR-A289V.

The disclosure demonstrates that like EGFR-Viii, an additional group of commonly occurring EGFR variants in GBM (EGFR-Vii, EGFR-Vvi, EGFR-G598V and EGFR-A289V) all exist as constitutively active covalent dimers and together form a family of EGFR isoforms that are activated by this common mechanism. Furthermore, the disclosure shows that the propensity of these variants to covalently dimerize is coupled to the conformation of the intracellular catalytic site, conferring distinct activity for classes of small molecules inhibitors binding to this distal site. Inhibitors that stabilize the active conformation of the kinase (Type I inhibitors, including erlotinib) induce the formation of covalent dimers for all covalently-activated EGFR isoforms. This is associated with the propensity of Type I inhibitors to increase EGFR phosphorylation at sub-saturating concentrations and to paradoxically stimulate the proliferation of cells expressing covalently-activated EGFR isoforms.

Neither enhanced dimerization nor paradoxical activation of EGFR is seen with small molecule inhibitors that stabilize the inactive kinase conformation (Type II inhibitors, including lapatinib and neratinib). Examples of Type II inhibitors were identified that were potent inhibitors of covalently-activated EGFR isoforms and which were selective for this family compared to WT-EGFR.

Similar to the mutations identified for EGFR, the disclosure identifies a group of splice events and mutations affecting the CR domains of HER2 and HER4. The disclosure demonstrates that this group of splice events and mutations affecting the CR domains of HER2 and HER4 exists as covalent dimers and are paradoxically activated by agents with a Type I binding mode. These data provide a mechanistic explanation for the failure of multiple clinical trials involving Type I inhibitors, including >30 clinical trials of Type I ErbB inhibitors in GBM. Collectively these data indicate that tumors expressing covalently-activated EGFR isoforms should be excluded from treatment with Type I ErbB inhibitors such as erlotinib because of paradoxical activation. These data further demonstrate the utility for optimizing Type II ErbB inhibitors against the covalently-activated ErbB family.

Methods and Uses of the Present Disclosure

In some aspects, the present disclosure provides a method of treating or preventing (e.g., treating) cancer in a subject in need thereof, comprising administering to the subject a pharmaceutically effective amount of Compound No. 1, Compound No. 2, or a pharmaceutically acceptable salt thereof.

In some aspects, the present disclosure provides a method of treating or preventing (e.g., treating) cancer in a subject in need thereof, comprising administering to the subject a pharmaceutically effective amount of Compound No. 1 (e.g., Compound No. 1A or Compound No. 1B) or a pharmaceutically acceptable salt thereof.

In some aspects, the present disclosure provides a method of treating or preventing (e.g., treating) cancer in a subject in need thereof, comprising administering to the subject a pharmaceutically effective amount of Compound No. 2 (e.g., Compound No. 2A or Compound No. 2B) or a pharmaceutically acceptable salt thereof.

In some aspects, the present disclosure provides Compound No. 1, Compound No. 2, or a pharmaceutically acceptable salt thereof for treating or preventing (e.g., treating) cancer in a subject in need thereof.

In some aspects, the present disclosure provides Compound No. 1 (e.g., Compound No. 1A or Compound No. 1B) or a pharmaceutically acceptable salt thereof for treating or preventing (e.g., treating) cancer in a subject in need thereof.

In some aspects, the present disclosure provides Compound No. 2 (e.g., Compound No. 2A or Compound No. 2B) or a pharmaceutically acceptable salt thereof for treating or preventing (e.g., treating) cancer in a subject in need thereof.

In some aspects, the present disclosure provides use of Compound No. 1, Compound No. 2, or a pharmaceutically acceptable salt thereof, in the manufacture of a medicament for treating or preventing (e.g., treating) cancer in a subject in need thereof.

In some aspects, the present disclosure provides use of Compound No. 1 (e.g., Compound No. 1A or Compound No. 1B) or a pharmaceutically acceptable salt thereof, in the manufacture of a medicament for treating or preventing (e.g., treating) cancer in a subject in need thereof.

In some aspects, the present disclosure provides use of Compound No. 2 (e.g., Compound No. 2A or Compound No. 2B) or a pharmaceutically acceptable salt thereof, in the manufacture of a medicament for treating or preventing (e.g., treating) cancer in a subject in need thereof.

In some embodiments, Compound No. 1A, Compound No. 1B, or the pharmaceutically acceptable salt thereof is administered.

In some embodiments, Compound No. 1A the pharmaceutically acceptable salt thereof is administered.

In some embodiments, Compound No. 1B the pharmaceutically acceptable salt thereof is administered.

In some embodiments, Compound No. 2A, Compound No. 2B, or the pharmaceutically acceptable salt thereof is administered.

In some embodiments, Compound No. 2A or the pharmaceutically acceptable salt thereof is administered.

In some embodiments, Compound No. 2B or the pharmaceutically acceptable salt thereof is administered.

Suitable Subjects and Diseases

In some embodiments, the subject is a mammal. In some embodiments, the subject is a human. In some embodiments, the subject is a human adult (e.g., being 18 years of age or order).

In some embodiments, the subject is a mouse. In some embodiments, the subject is a rat. In some embodiments, the subject is a dog.

The compounds of the disclosure inhibit or modulate the activity of a receptor tyrosine kinase, in particular extracellular mutants of ErbB-receptors, such as, but not limited to, EGFR-Viii, EGFR-Vii, EGFR-Vvi, EGFR-A289V and EGFR-G598V and HER2-S310F. Thus, the compounds and compositions of the disclosure can be useful as a medicament, i.e. as a medicament in therapy, more specifically for the prevention or treatment of cancer, as detailed below. Therefore, in a further aspect, the present disclosure provides a method of prevention or treatment of a mammal, for example, a human, suffering from cancer, as detailed below.

In some aspects, the present disclosure is directed to a method of inhibiting an oncogenic variant of an ErbB receptor (e.g., an oncogenic variant of an EGFR), comprising administering the subject in need thereof a therapeutically effective amount of a compound described herein.

In some aspects, the present disclosure is directed to a method of inhibiting an oncogenic variant of an ErbB receptor (e.g., an oncogenic variant of an EGFR), comprising administering the subject in need thereof a composition described herein.

In some aspects, the present disclosure is directed to a method of preventing or treating cancer, comprising administering the subject in need thereof a therapeutically effective amount of a compound described herein.

In some aspects, the present disclosure is directed to a method of preventing or treating cancer, comprising administering the subject in need thereof a composition described herein.

In some aspects, the present disclosure is directed to a compound described herein for use in the inhibition of an oncogenic variant of an ErbB receptor (e.g., an oncogenic variant of an EGFR).

In some aspects, the present disclosure is directed to a compound described herein for use in the prevention or treatment of cancer.

In some aspects, the present disclosure is directed to a composition described herein for use in the inhibition of an oncogenic variant of an ErbB receptor (e.g., an oncogenic variant of an EGFR).

In some aspects, the present disclosure is directed to a composition described herein for use in the prevention or treatment of cancer.

In some aspects, the present disclosure is directed to use of a compound described herein in the manufacture of a medicament for inhibiting an oncogenic variant of an ErbB receptor (e.g., an oncogenic variant of an EGFR).

In some aspects, the present disclosure is directed to use of a compound described herein in the manufacture of a medicament for preventing or treating cancer.

In some embodiments, the compound is selected from the compounds described in Tables 1 and 2, pharmaceutically acceptable salts thereof, and stereoisomers thereof.

In some embodiments, the compound is selected from the compounds described in Tables 1 and 2 and pharmaceutically acceptable salts thereof.

In some embodiments, the compound is selected from the compounds described in Tables 1 and 2.

In some embodiments, cancer is a solid tumor.

In some embodiments, the cancer is a bladder cancer, a breast cancer, a cervical cancer, a colorectal cancer, an endometrial cancer, a gastric cancer, a glioblastoma (GBM), a head and neck cancer, a lung cancer, a non-small cell lung cancer (NSCLC), or any subtype thereof.

In some embodiments, the cancer is glioblastoma (GBM) or any subtype thereof. In some embodiments, the cancer is glioblastoma.

In some embodiments, the cancer is glioblastoma and the cancer is characterized by overexpression of EGFR.

In some embodiments, the cancer is methylated glioblastoma. In some embodiments, the cancer is unmethylated glioblastoma.

In some embodiments, the cancer is recurrent glioblastoma.

In some embodiments, the cancer is relapsed glioblastoma.

In some embodiments, the cancer is glioblastoma and the cancer, or a tumor or cell thereof, expresses at least one oncogenic variant of EGFR.

In some embodiments, the cancer is relapsed glioblastoma and the cancer, or a tumor or cell thereof, expresses at least one oncogenic variant of EGFR.

In some embodiments, the cancer is recurrent glioblastoma and the cancer, or a tumor or cell thereof, expresses at least one oncogenic variant of EGFR.

In some embodiments, the cancer is non-small cell lung cancer (NSCLC) or any subtype thereof.

In some embodiments, the cancer is non-small cell lung cancer (NSCLC).

In some embodiments, the cancer is recurrent non-small cell lung cancer (NSCLC).

In some embodiments, the cancer is relapsed non-small cell lung cancer (NSCLC).

In some embodiments, the cancer is NSCLC and the cancer, or a tumor or cell thereof, expresses at least one oncogenic variant of EGFR.

In some embodiments, the cancer is recurrent NSCLC and the cancer, or a tumor or cell thereof, expresses at least one oncogenic variant of EGFR.

In some embodiments, the cancer is relapsed NSCLC and the cancer, or a tumor or cell thereof, expresses at least one oncogenic variant of EGFR.

In some embodiments, the cancer is advanced or metastatic NSCLC.

In some embodiments, the cancer is advanced or metastatic NSCLC and the cancer, or a tumor or cell thereof, expresses at least one oncogenic variant of EGFR.

In some embodiments, the cancer is NSCLC, wherein the cancer has metastasized to the central nervous system (CNS).

In some embodiments, the cancer is advanced or metastatic NSCLC, wherein the cancer, or a tumor or cell thereof, expresses at least one oncogenic variant of EGFR, and wherein the cancer has metastasized to the central nervous system (CNS).

In some embodiments, the cancer is advanced or metastatic NSCLC, wherein the cancer, or a tumor or cell thereof, expresses at least one oncogenic variant of EGFR, and wherein the cancer has not metastasized to the central nervous system (CNS).

In some embodiments, the cancer is NSCLC, wherein the cancer has not metastasized to cerebrospinal fluid (CSF).

In some embodiments, the cancer is NSCLC, wherein the cancer has metastasized to cerebrospinal fluid (CSF).

In some embodiments, the cancer is glioblastoma, wherein the cancer has not metastasized to cerebrospinal fluid (CSF).

In some embodiments, the cancer is glioblastoma, wherein the cancer has metastasized to cerebrospinal fluid (CSF).

In some embodiments, the cancer is NSCLC, wherein the cancer has not metastasized to the brain.

In some embodiments, the cancer is NSCLC, wherein the cancer has metastasized to the brain.

In some embodiments, the subject has a central nervous system (CNS) disease.

In some embodiments, the subject does not have any CNS disease.

In some embodiments, the subject has a leptomeningeal disease.

In some embodiments, the subject does not have any leptomeningeal disease.

In some embodiments, the cancer is NSCLC and the subject has leptomeningeal disease.

In some embodiments, the cancer is glioblastoma and the subject has leptomeningeal disease.

In some embodiments, the cancer, or a tumor or a cell thereof, expresses an oncogenic variant of an ErbB receptor.

It is understood that an oncogenic variant of an ErbB receptor is an ErbB receptor protein that comprises at least one oncogenic mutation and that is produced as the result of the expression of a gene encoding the ErbB receptor that comprises at least one oncogenic mutation.

As would be appreciated by the skilled artisan, in the context of a gene (e.g. a gene encoding an ErbB receptor), an oncogenic mutation can include, but is not limited to a mutation that results in the substitution of one amino acid for another at a specific position within an ErbB receptor, a mutation that results in an insertion of one or more amino acids between two positions within an ErbB receptor, a mutation that results in the deletion of one more amino acids between two positions within an ErbB receptor, and mutation that results in a fusion of an ErbB receptor or portion thereof, with another protein, or portion thereof. As would be appreciated by the skilled artisan, in the context of a gene, an oncogenic mutation can include, but is not limited to, a missense mutation, a nonsynonymous mutation, an insertion of one or more nucleotides, a deletion of one or more nucleotides, an inversion and a deletion-insertion.

As would be appreciated by the skilled artisan, in the context of a protein (e.g. an ErbB receptor), an oncogenic mutation can include, but is not limited to, the substitution of one amino acid for another at a specific position within an ErbB receptor, an insertion of one or more amino acids between two positions within an ErbB receptor, a deletion of one more amino acids between two positions within an ErbB receptor, and a fusion of an ErbB receptor, or portion thereof, with another protein, or portion thereof.

In some embodiments, the oncogenic variant of the ErbB receptor comprises an allosteric mutation.

In some embodiments, the oncogenic variant of an ErbB receptor is an allosteric variant of the ErbB receptor.

In some embodiments, the ErbB receptor is an epidermal growth factor receptor (EGFR) or a human epidermal growth factor receptor 2 (HER2) receptor.

In some embodiments, the ErbB receptor is an epidermal growth factor receptor (EGFR).

In some embodiments, the ErbB receptor is a HER2 receptor.

In some embodiments, the ErbB receptor is a HER3 receptor.

In some embodiments, the ErbB receptor is a HER4 receptor.

In some embodiments, the cancer, or a tumor or a cell thereof, expresses an oncogenic variant of an epidermal growth factor receptor (EGFR).

In some embodiments, the oncogenic variant of EGFR is an allosteric variant of EGFR.

In some embodiments, the oncogenic variant of EGFR comprises an allosteric mutation.

In some embodiments, the cancer, or a tumor or a cell thereof, expresses an oncogenic variant of a HER2 receptor.

In some embodiments, the oncogenic variant of the HER2 receptor is an allosteric variant of the HER2 receptor.

In some embodiments, the oncogenic variant of the HER2 receptor comprises an allosteric mutation.

In some embodiments, the oncogenic variant of an EGFR comprises an EGFR variant III (EGFR-Viii) mutation.

In some embodiments, the oncogenic variant of EGFR comprises an EGFR variant II (EGFR-Vii) mutation.

In some embodiments, the oncogenic variant of EGFR comprises an EGFR variant VI (EGFR-Vvi) mutation.

In some embodiments, the oncogenic variant of EGFR comprises a substitution of a lysine (K) for an arginine (R) at position 108 of SEQ ID NO: 1.

In some embodiments, the oncogenic variant of EGFR comprises a substitution of a cysteine (C) for an arginine (R) at position 222 of SEQ ID NO: 1.

In some embodiments, the oncogenic variant of EGFR comprises a substitution of a threonine (T) for an alanine (A) at position 289 of SEQ ID NO: 1.

In some embodiments, the oncogenic variant of EGFR comprises a substitution of a valine (V) for an alanine (A) at position 289 of SEQ ID NO: 1.

In some embodiments, the oncogenic variant of EGFR comprises a substitution of a valine (V) for a glycine (G) at position 598 of SEQ ID NO: 1.

In some embodiments, the oncogenic variant of EGFR comprises a substitution of a phenylalanine (F) for a cysteine (C) at position 231 of SEQ ID NO: 1.

In some embodiments, the oncogenic variant of EGFR comprises a substitution of a serine for a cysteine at position 595 of SEQ ID NO: 1.

In some embodiments, the oncogenic variant of EGFR comprises a substitution of a valine (V) for a glycine (G) at position 598 of SEQ ID NO: 1.

In some embodiments, the oncogenic variant of EGFR comprises a substitution of a cysteine (C) for a serine (S) at position 645 of SEQ ID NO: 1.

In some embodiments, the oncogenic variant of EGFR comprises a substitution of glycine (G) at position 719 of SEQ ID NO: 1, wherein the substitution is selected from cysteine (C), aspartate (D), arginine (R), serine (S), or alanine (A).

In some embodiments, the oncogenic variant of EGFR comprises a substitution of serine (S) for a glycine (G) at position 719 of SEQ ID NO: 1.

In some embodiments, the oncogenic variant of EGFR comprises a substitution of serine (S) for cysteine (C) at position 797 of SEQ ID NO: 1.

In some embodiments, the cancer, or a tumor or a cell thereof, expresses an oncogenic variant of an EGFR and wherein the oncogenic variant of EGFR is an allosteric variant of EGFR, the oncogenic variant of an EGFR comprises a modification of a structure of the EGFR, wherein the oncogenic variant of an EGFR is a capable of forming a covalently linked dimer, wherein the covalently linked dimer is constitutively active and wherein the covalently linked dimer enhances an activity of EGFR when contacted to a Type I ErbB inhibitor. In some embodiments, the modification of the structure of the EGFR comprises a modification of one or more of a nucleic acid sequence, an amino acid sequence, a secondary structure, a tertiary structure, and a quaternary structure. In some embodiments, the oncogenic variant comprises a mutation, a splicing event, a post-translational process, a conformational change or any combination thereof. In some embodiments, the modification of the structure of the EGFR occurs within a first cysteine rich (CR1) and/or second cysteine rich (CR2) region of EGFR. In some embodiments, the first cysteine rich (CR1) and/or second cysteine rich (CR2) region of EGFR comprises amino acid residues T211-R334 and/or C526-S645 of SEQ ID NO: 1, respectively. In some embodiments, the oncogenic variant of an EGFR generates a physical barrier to formation of a disulfide bond within the CR1 and/or the CR2 region. In some embodiments, the oncogenic variant of an EGFR removes a physical barrier to formation of a disulfide bond within the CR1 and/or the CR2 region. In some embodiments, the oncogenic variant of an EGFR comprises one or more free or unpaired Cysteine (C) residues located at a dimer interface of the EGFR. In some embodiments, the oncogenic variant of an EGFR comprises one or more free or unpaired Cysteine (C) residues at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1. In some embodiments, the modification occurs within 10 angstroms or less of an intramolecular disulfide bond at a site selected from the group consisting of C190-C199, C194-C207, C215-C223, C219-C231, C232-C240, C236-C248, C251-C260, C264-C291, C295-C307, C311-C326, C329-C333, C506-C515, C510-C523, C526-C535, C539-C555, C558-C571, C562-C579, C582-C591, C595-C617, C620-C628 and C624-C636 according to SEQ ID NO: 1.

In some embodiments, the cancer, or a tumor or a cell thereof, expresses an oncogenic variant of EGFR and the oncogenic variant of EGFR is a mutation of EGFR, a nucleotide sequence encoding the oncogenic variant of an EGFR comprises a deletion or the substitution comprises one or more amino acids that encode an adenosine triphosphate (ATP) binding site. In some embodiments, the ATP binding site comprises amino acids E746 to A750 of SEQ ID NO: 1. In some embodiments, the ATP binding site or the deletion or substitution thereof comprises L858 of SEQ ID NO: 1. In some embodiments, the deletion comprises L858 of SEQ ID NO: 1. In some embodiments, an arginine (R) is substituted for the leucine (L) at position 858 (L858R) of SEQ ID NO: 1.

In some embodiments, the cancer, or a tumor or a cell thereof, expresses an oncogenic variant of an EGFR and wherein the oncogenic variant of EGFR is an allosteric variant of EGFR, a nucleotide sequence encoding the oncogenic variant of an EGFR comprises an insertion within a sequence encoding exon 20 or a portion thereof. In some embodiments, the sequence encoding exon 20 or a portion thereof comprises a sequence encoding KEILDEAYVMASVDNPHVCAR (SEQ ID NO: 7). In some embodiments, the sequence encoding exon 20 or a portion thereof comprises a sequence encoding a C-helix, a terminal end of the C-helix or a loop following the C-helix. In some embodiments, the insertion comprises the amino acid sequence of ASV, SVD, NPH, or FQEA. In some embodiments, the sequence encoding exon 20 or a portion thereof comprises one or more of: (a) an insertion of the amino acid sequence ASV between positions V769 and D770 of SEQ ID NO: 1; (b) an insertion of the amino acid sequence SVD between positions D770 and N771 of SEQ ID NO: 1; (c) an insertion of the amino acid sequence NPH between positions H773 and V774 of SEQ ID NO: 1; (d) an insertion of the amino acid sequence FQEA between positions A763 and Y764 of SEQ ID NO: 1; (e) an insertion of the amino acid sequence PH between positions H773 and V774 of SEQ ID NO: 1; (f) an insertion of the amino acid G between positions D770 and N771 of SEQ ID NO: 1; (g) an insertion of the amino acid H between positions H773 and V774 of SEQ ID NO: 1; (h) an insertion of the amino acid sequence HV between positions V774 and C775 of SEQ ID NO: 1; (i) an insertion of the amino acid sequence AH between positions H773 and V774 of SEQ ID NO: 1; (j) an insertion of the amino acid sequence SVA between positions A767 and S768 of SEQ ID NO: 1; (k) a substitution of the amino acid sequence GYN for the DN between positions 770 and 771 of SEQ ID NO: 1; (l) an insertion of the amino acid H between positions N771 and P772 of SEQ ID NO: 1; (m) an insertion of the amino acid Y between positions H773 and V774 of SEQ ID NO: 1; (n) an insertion of the amino acid sequence PHVC between positions C775 and R776 of SEQ ID NO: 1; (o) a substitution of the amino acid sequence YNPY for the H at position 773 of SEQ ID NO: 1; (p) an insertion of the amino acid sequence DNP between positions P772 and H773 of SEQ ID NO: 1; (q) an insertion of the amino acid sequence VDS between positions S768 and V769 of SEQ ID NO: 1; (r) an insertion of the amino acid H between positions D770 and N771 of SEQ ID NO: 1; (s) an insertion of the amino acid N between positions N771 and P772 of SEQ ID NO: 1;

(t) an insertion of the amino acid sequence PNP between positions P772 and H773 of SEQ ID NO: 1; (u) a substitution of the amino acid sequence GSVDN for the DN between positions 770 and 771 of SEQ ID NO: 1; (v) a substitution of the amino acid sequence GYP for the NP between positions 771 and 772 of SEQ ID NO: 1; (w) an insertion of the amino acid G between positions N771 and P772 of SEQ ID NO: 1; (x) an insertion of the amino acid sequence GNP between positions P772 and H773 of SEQ ID NO: 1; (y) an insertion of the amino acid sequence GSV between positions V769 and D770 of SEQ ID NO: 1; (z) a substitution of the amino acid sequence GNPHVC for the VC between positions 774 and 775 of SEQ ID NO: 1; (aa) an insertion of the amino acid sequence LQEA between positions A763 and Y764 of SEQ ID NO: 1; (bb) an insertion of the amino acid sequence GL between positions D770 and N771 of SEQ ID NO: 1; (cc) an insertion of the amino acid Y between positions D770 and N771 of SEQ ID NO: 1; (dd) an insertion of the amino acid sequence NPY between positions H773 and V774 of SEQ ID NO: 1; (ee) an insertion of the amino acid sequence TH between positions H773 and V774 of SEQ ID NO: 1; (ff) a substitution of the amino acid sequence KGP for the NP between positions 771 and 772 of SEQ ID NO: 1; (gg) a substitution of the amino acid sequence SVDNP for the NP between positions 771 and 772 of SEQ ID NO: 1; (hh) an insertion of the amino acid sequence NN between positions N771 and P772 of SEQ ID NO: 1; (ii) an insertion of the amino acid T between positions N771 and P772 of SEQ ID NO: 1; and (jj) a substitution of the amino acid sequence STLASV for the SV between positions 768 and 769 of SEQ ID NO: 1.

In some embodiments, an oncogenic variant of EGFR can have or more mutations in exon 18.

In some embodiments, an oncogenic variant of EGFR can have or more mutations in exon 19.

In some embodiments, an oncogenic variant of EGFR can have or more mutations in exon 20.

In some embodiments, the cancer, or a tumor or a cell thereof, expresses an oncogenic variant of an EGFR and wherein the oncogenic variant of EGFR is an allosteric variant of EGFR.

In some embodiments, the oncogenic variant of an EGFR can be any of the following: EGFR-Viii, EGFR-Vii, EGFR-Vvi, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P596S, EGFR-P596L, EGFR-P596R, EGFR-G598V, EGFR-G598A, EGFR-G614D, EGFR-C620Y, EGFR-C614W, EGFR-C628F, EGFR-C628Y, EGFR-C636Y, EGFR-S645C, EGFR-4660, EGFR-4768, EGFR-C231F, EGFR-C231F, EGFR-0595S, EGFR-D761Y, EGFR-G719C, EGFR-G719D, EGFR-G719R, EGFR-L858R, EGFR-E746-A750del, EGFR-E746-A750del+C797S, EGFR-E746-A750del+C797S+T790M, EGFR-C797S or any combination thereof.

In some embodiments, the oncogenic variant of an EGFR is selected from: EGFR-Viii, EGFR-Vii, EGFR-Vvi, EGFR-R108K, EGFR-R222C, EGFR-R252C, EGFR-R252P, EGFR-R256Y, EGFR-T263P, EGFR-Y270C, EGFR-A289T, EGFR-A289V, EGFR-A289D, EGFR-H304Y, EGFR-G331R, EGFR-P596S, EGFR-P596L, EGFR-P596R, EGFR-G598V, EGFR-G598A, EGFR-G614D, EGFR-C620Y, EGFR-C614W, EGFR-C628F, EGFR-C628Y, EGFR-C636Y, EGFR-S645C, EGFR-4660, EGFR-4768, EGFR-V689M, EGFR-N700D, EGFR-E709K, EGFR-E709Q, EGFR-E709A, EGFR-E709G, EGFR-E709V, EGFR-S768I, EGFR-C231F, EGFR-0595S, EGFR-D761Y, EGFR-L718Q, EGFR-G719C, EGFR-G719D, EGFR-G719R, EGFR-G719A, EGFR-G719S, EGFR-G724S, EGFR-L858R, EGFR-L858R+C797S, EGFR-L861Q, EGFR-E746-A750del, EGFR-E746-A750del+C797S, EGFR-E746-A750del+S768I, EGFR-E746-A750del+C797S+T790M, EGFR-C797S, EGFR-Δ19+C797S, EGFR-Δ19+C797S+T790M, EGFR-Δ19+S768I, EGFR-G719C+S768I, EGFR-D716Y or any combination thereof.

In some embodiments, the oncogenic variant of EGFR comprises an insertion within exon 20, wherein the insertion comprises the amino acid sequence of ASV, SVD, NPH or FQEA.

In some embodiments, the oncogenic variant of EGFR comprises an insertion in exon 20, wherein the insertion in exon 20 is selected from the group of insertions recited in Table 1.

TABLE 1

| EGFR Exon 20 insertions (numbering corresponding to SEQ ID NO: 1) Insertion Description |
|---|
| an insertion of the amino acid sequence ASV between positions V769 and D770 (V769_D770insASV; A767_V769dup; A767-V769dupASV) |
| an insertion of the amino acid sequence SVD between positions D770 and N771 (D770_N771insSVD; S768_D770dup; S768_D770dupSVD) |
| an insertion of the amino acid sequence NPH between positions H773 and V774 (H773_V774insNPH; N771_H773dup; N771_H773dupNPH) |
| an insertion of the amino acid sequence FQEA between positions A763 and Y764 (A763_Y764 FQEA; A763_Y764insFQEA) |
| an insertion of the amino acid sequence PH between positions H773 and V774 (H773_V774insPH; P772_H773dup; P772_H773dupPH) |
| an insertion of the amino acid G between positions D770 and N771(D770_N771insG; D771_P772insG) |
| an insertion of the amino acid H between positions H773 and V774 (H773_V774insH; H773dup; H773dupH) |
| an insertion of the amino acid sequence HV between positions V774 and C775 (V774_C775insHV; H773_V774dup; H773_V774dupHV) |
| an insertion of the amino acid sequence AH between positions H773 and V774 (H773_V774insAH) |
| an insertion of the amino acid sequence SVA between positions A767 and S768 (A767_S768insSVA; A767_V769dup; A767_V769dupSVA) |
| an insertion of the amino acid H between positions N771 and P772 |
| an insertion of the amino acid Y between positions H773 and V774 (H773_V774insY) |
| an insertion of the amino acid sequence PHVC between positions C775 and R776 (C775_R776insPHVC) |

TABLE 1-continued

| EGFR Exon 20 insertions (numbering corresponding to SEQ ID NO: 1) Insertion Description |
|---|
| an insertion of the amino acid sequence DNP between positions P772 and H773 (P772_H773insDNP; D770_P772dup; D770_P772dupDNP) |
| an insertion of the amino acid sequence VDS between positions S768 and V769 (S768_V769insVDS) |
| an insertion of the amino acid H between positions D770 and N771 (N771_P772insH) |
| an insertion of the amino acid N between positions N771 and P772 |
| an insertion of the amino acid sequence PNP between positions P772 and H773 (P772_H773insPNP) |
| an insertion of the amino acid G between positions N771 and P772 (N771_P772insG) |
| an insertion of the amino acid sequence GNP between positions P772 and H773 (P772_H773insGNP) |
| an insertion of the amino acid sequence GSV between positions V769 and D770 |
| an insertion of the amino acid sequence LQEA between positions A763 and Y764 |
| an insertion of the amino acid sequence GL between positions D770 and N771 |
| an insertion of the amino acid Y between positions D770 and N771 |
| an insertion of the amino acid sequence NPY between positions H773 and V774 |
| an insertion of the amino acid sequence TH between positions H773 and V774 |
| an insertion of the amino acid sequence NN between positions N771 and P772 |
| an insertion of the amino acid T between positions N771 and P772 |

In some embodiments, the oncogenic variant of EGFR comprises a substitution within exon 20 of EGFR.

In some embodiments, the oncogenic variant of EGFR comprises a substitution in exon wherein the substitution in exon 20 is selected from the group of substitutions recited in Table 2.

TABLE 2

| EGFR Exon 20 substitutions (numbering corresponding to SEQ ID NO: 1) Substitution Description |
|---|
| a substitution of the amino acid sequence GYN for the DN between positions 770 and 771 (D770_N771 > GYN; D770_N771delinsGYN; D770_N771insGYN) |
| a substitution of the amino acid sequence GF for the N at position N771 (N771 > GF; N771delinsGF) |
| a substitution of the amino acid sequence GY for the D at position 770 (D770 > GY; D770delinsGY) |
| a substitution of the amino acid sequence YNPY for the H at position 773 (H773 > YNPY; H773 delins YNPY) |
| a substitution of the amino acid sequence GSVDN for the DN between positions 770 and 771 |
| a substitution of the amino acid sequence GYP for the NP between positions 771 and 772 |
| a substitution of the amino acid sequence GNPHVC for the VC between positions 774 and 775 |
| a substitution of the amino acid sequence KGP for the NP between positions 771 and 772 |
| a substitution of the amino acid sequence SVDNP for the NP between positions 771 and 772 |
| a substitution of the amino acid sequence STLASV for the SV between positions 768 and 769 |

In some embodiments, the oncogenic variant of EGFR can be any of the EGFR variants put forth in Table 3.

TABLE 3

| EGFR oncogenic variants | | |
|---|---|---|
| EGFR-Vii | EGFR-A289V | EGFR-C620Y |
| EGFR-Viii | EGFR-A289D | EGFR-C614W |
| EGFR-Vvi | EGFR-H304Y | EGFR-C628F |
| EGFR-R222C | EGFR-G331R | EGFR-C628Y |
| EGFR-R252C | EGFR-P596S | EGFR-C636Y |
| EGFR-R252P | EGFR-P596L | EGFR-S645C |
| EGFR-R256Y | EGFR-P596R | EGFR-Δ660 |
| EGFR-T263P | EGFR-G598V | EGFR-Δ768 |
| EGFR-Y270C | EGFR-G598A | EGFR-L858R |
| EGFR-A289T | EGFR-G614D | EGFR-Δ19 (deletion of Exon 19) |
| EGFR-R108K | EGFR-V689M | EGFR-N700D |
| EGFR-E709K | EGFR-E709Q | EGFR-E709A |
| EGFR-E709G | EGFR-E709V | EGFR-S768I |
| EGFR-L718Q | EGFR-G719A | EGFR-G719S |
| EGFR-G724S | EGFR-L858R + C797S | EGFR-Δ19 + C797S |

TABLE 3-continued

| EGFR oncogenic variants | | |
|---|---|---|
| EGFR-C231F | EGFR-C595S | EGFR-G719C |
| EGFR-G719D | EGFR-G719R | EGFR-Δ19 + C797S + T790M |
| EGFR-C797S | EGFR-E746-A750del + C797S | EGFR-E746-A750del |
| EGFR-E746-A750del + C797S + T790M | EGFR-E746-A750del + S768I | EGFR-Δ19 + S768I |
| EGFR-G791S | EGFR-G719C + S768I | EGFR-D716Y |

In some embodiments, Δ19 can comprise the deletion of residues E746-A750 of EGFR (SEQ ID NO: 1).

In some embodiments, the cancer, or a tumor or a cell thereof, expresses one or more of: (a) a wild type human epidermal growth factor receptor 2 (HER2) receptor or an oncogenic variant of a HER2 receptor.

In some embodiments, the cancer, or a tumor or a cell thereof, expresses a wild type HER2 receptor, the wild type HER2 receptor comprises the amino acid sequence of SEQ ID NO: 2, 3, 4, 5, or 6.

In some embodiments, the cancer, or a tumor or a cell thereof, expresses an oncogenic variant of a HER2 receptor, the oncogenic variant of a HER2 receptor is an allosteric variant of the HER2 receptor.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a phenylalanine (F) for a serine (S) at position 310 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a tyrosine (Y) for a serine (S) at position 310 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a glutamine (Q) for an arginine (R) at position 678 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a leucine (L) for a valine (V) at position 777 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a methionine (M) for a valine (V) at position 777 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of an isoleucine (I) for a valine (V) at position 842 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of an alanine (A) for a leucine (L) at position 755 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a proline (P) for a leucine (L) at position 755 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises a substitution of a serine (S) for a leucine (L) at position 755 of SEQ ID NO: 2 or 5.

In some embodiments, the cancer, or a tumor or a cell thereof, expresses an oncogenic variant of a HER2 receptor and wherein the oncogenic variant of a HER2 receptor is an allosteric variant of the HER2 receptor, a nucleotide sequence encoding the oncogenic variant of a HER2 receptor comprises an insertion within a sequence encoding exon 20 or a portion thereof. In some embodiments, the sequence encoding exon 20 or a portion thereof comprises a sequence encoding KEILDEAYVMAGVGSPYVSR(SEQ ID NO: 8). In some embodiments, the sequence encoding exon 20 or a portion thereof comprises a sequence encoding a C-helix, a terminal end of the C-helix or a loop following the C-helix. In some embodiments, the insertion comprises the amino acid sequence of GSP or YVMA. In some embodiments, the sequence encoding exon 20 or a portion thereof comprises one or more of: (a) an insertion of the amino acid sequence YVMA between positions A775 and G776 of SEQ ID NO: 2; (b) an insertion of the amino acid sequence GSP between positions P780 and Y781 of SEQ ID NO: 2; (c) an insertion of the amino acid sequence YVMA between positions A771 and Y772 of SEQ ID NO: 2; (d) an insertion of the amino acid sequence YVMA between positions A775 and G776 of SEQ ID NO: 2; (e) an insertion of the amino acid V between positions V777 and G778 of SEQ ID NO: 2; (f) an insertion of the amino acid V between positions V777 and G778 of SEQ ID NO: 2; (g) a substitution of the amino acid sequence AVGCV for the GV between positions 776 and 777 of SEQ ID NO: 2; (h) a substitution of the amino acid sequence LC for the G between position 776 of SEQ ID NO: 2; (i) a substitution of the amino acid sequence LCV for the G between position 776 of SEQ ID NO: 2; (j) an insertion of the amino acid sequence GSP between positions V777 and G778 of SEQ ID NO: 2; (k) a substitution of the amino acid sequence PS for the LRE between positions 755 and 757 of SEQ ID NO: 2; (1) a substitution of the amino acid sequence CPGSP for the SP between positions 779 and 780 of SEQ ID NO: 2; (m) an insertion of the amino acid C between positions V777 and G778 of SEQ ID NO: 2; (n) a substitution of the amino acid sequence VVMA for the AG between positions 775 and 776 of SEQ ID NO: 2; (o) a substitution of the amino acid sequence VV for the G at position 776 of SEQ ID NO: 2; (p) a substitution of the amino acid sequence AVCV for the GV between positions 776 and 777 of SEQ ID NO: 2; (q) a substitution of the amino acid sequence VCV for the GV between positions 776 and 777 of SEQ ID NO: 2; (r) an insertion of the amino acid G between positions G778 and S779 of SEQ ID NO: 2; (s) a substitution of the amino acid sequence PK for the LRE between positions 755 and 757 of SEQ ID NO: 2; (t) an insertion of the amino acid V between positions A775 and G776 of SEQ ID NO: 2; (u) an insertion of the amino acid sequenceYAMA between positions A775 and G776 of SEQ ID NO: 2; (v) a substitution of the amino acid sequence CV for the G at position 776 of SEQ ID NO: 2; (w) a substitution of the amino acid sequence AVCGG for the GVG between positions 776 and 778 of SEQ ID NO: 2; (x) a substitution of the amino acid sequence CVCG for the GVG between positions 776 and 778 of SEQ ID NO: 2; (y) a substitution of the amino acid sequence VVVG for the GVG between positions 776 and 778 of SEQ ID NO: 2; (z) a substitution of the amino acid sequence SVGG for the GVGS between positions 776 and 779 of SEQ ID NO: 2; (aa) a substitution of the amino acid sequence VVGES for the GVGS between positions 776 and 779 of SEQ ID NO: 2; (bb) a substitution of the amino acid sequence AVGSGV for the GV between positions 776 and 777 of SEQ ID NO: 2; (cc) a substitution of the amino acid sequence CVC for the GV between positions 776 and 777 of SEQ ID NO: 2; (dd) a substitution of the amino acid sequence HVC for the GV between positions 776 and 777 of SEQ ID NO: 2; (ee) a substitution of the amino acid sequence VAAGV for the GV between positions 776 and 777 of SEQ ID NO: 2; (ff) a substitution of the amino acid sequence VAGV for the GV between positions 776 and 777 of SEQ ID NO: 2; (gg) a substitution of the amino acid sequence VVV for the GV between positions 776 and 777 of SEQ ID NO: 2; (hh) an insertion of the amino acid sequence FPG between positions G778 and S779 of SEQ ID NO: 2; (ii) an insertion of the amino acid sequence GS between positions S779 and P780 of SEQ ID NO: 2; (jj) a substitution of the amino acid sequence VPS for the VLRE between positions 754 and 757 of SEQ ID NO: 2; (kk) an insertion of the amino acid E between positions V777 and G778 of SEQ ID NO: 2; (ll) an insertion of the amino acid sequence MAGV between positions V777 and G778 of SEQ ID NO: 2; (mm) an insertion of the amino acid S between positions V777 and G778 of SEQ ID NO: 2; (nn) an insertion of the amino acid sequence SCV between positions V777 and G778 of SEQ ID NO: 2; and (oo) an insertion of the amino acid sequence LMAY between positions Y772 and V773 of SEQ ID NO: 2.

In some embodiments, the cancer, or a tumor or a cell thereof, expresses an oncogenic variant of a HER2 receptor and wherein the oncogenic variant of a HER2 receptor is an allosteric variant of the HER2 receptor, the oncogenic variant of a HER2 receptor comprises HER2-416, HER2-C311R, HER2-S310F, p95-HER2-M611 or any combination thereof.

In some embodiments, the oncogenic variant of HER2 comprises an insertion within exon wherein the insertion comprises the amino acid sequence of GSP or YVMA.

In some embodiments, the oncogenic variant of HER2 comprises an insertion in exon 20, wherein the insertion in exon 20 is selected from the group of insertions recited in Table 4.

TABLE 4

| HER2 Exon 20 insertions (numbering corresponding to SEQ ID NO: 2) Insertion Description |
|---|
| an insertion of the amino acid sequence YVMA between positions A775 and G776 (A775_G776insYVMA; Y772_A775dup) |
| an insertion of the amino acid sequence YVMD between positions A775 and G776 (A775_G776insYVMD) |
| an insertion of the amino acid sequence SVMA between positions A775 and G776 (A775_G776insSVMA) |
| an insertion of the amino acid sequence GSP between positions P780 and Y781 (P780_Y781insGSP; G778_P780dup) |
| an insertion of the amino acid sequence YVMA between positions A771 and Y772 (A771_Y772insYVMA; Y772_A775dup) |
| an insertion of the amino acid V between positions V777 and G778 (V777_G778insV; V777dup) |
| an insertion of the amino acid sequence GSP between positions V777 and G778 (V777_G778insGSP; G778_P780dup) |
| an insertion of the amino acid C between positions V777 and G778 (V777_G778insC) |
| an insertion of the amino acid G between positions G778 and S779 (G778_S779insG; G778dup) |
| an insertion of the amino acid V between positions A775 and G776 (A775_G776insV) |
| an insertion of the amino acid sequence VVMA between positions A775 and G776 (A775_G776insVVMA) |
| an insertion of the amino acid sequence YAMA between positions A775 and G776(A775_G776insYAMA) |
| an insertion of the amino acid sequence FPG between positions G778 and S779 |
| an insertion of the amino acid sequence CPG between positions G778 and S779 (G778_S779insCPG) |
| an insertion of the amino acid sequence GS between positions S779 and P780 |
| an insertion of the amino acid E between positions V777 and G778 |
| an insertion of the amino acid sequence MAGV between positions V777 and G778 |
| an insertion of the amino acid S between positions V777 and G778 |
| an insertion of the amino acid sequence SCV between positions V777 and G778 |
| an insertion of the amino acid sequence LMAY between positions Y772 and V773 |
| an insertion of the amino acid sequence VC at position G776 (G776insVC) |

In some embodiments, the oncogenic variant of HER2 comprises a substitution within exon 20 of HER2.

In some embodiments, the oncogenic variant of EGFR comprises a substitution in exon 20, wherein the substitution in exon 20 is selected from the group of substitutions recited in Table 5.

TABLE 5

| HER2 Exon 20 substitutions (numbering corresponding to SEQ ID NO: 2) Substitution Description |
|---|
| a substitution of the amino acid sequence AVGCV for the GV between positions 776 and 777 |
| a substitution of the amino acid sequence LC for the G at position 776 (G776delinsLC) |
| a substitution of the amino acid sequence VC for the G at position 776 (G776delinsVC) |
| a substitution of the amino acid sequence LCV for the G at position 776 |

TABLE 5-continued

| HER2 Exon 20 substitutions (numbering corresponding to SEQ ID NO: 2) Substitution Description |
|---|
| a substitution of the amino acid sequence PS for the LRE between positions 755 and 757 |
| a substitution of the amino acid sequence CPGSP for the SP between positions 779 and 780 |
| a substitution of the amino acid sequence VVMA for the AG between positions 775 and 776 |
| a substitution of the amino acid sequence VV for the G at position 776 |
| a substitution of the amino acid sequence AVCV for the GV between positions 776 and 777 (G776_V777 > AVCV; G776_V777delinsAVCV) |
| a substitution of the amino acid sequence AVGCV for the GV between positions 776 and 777 (G776_V777 > AVGCV; G776_V777delinsAVGC) |
| a substitution of the amino acid sequence LCV for the GV between positions 776 and 777 (G776_V777 > LCV; G776_V777delinsLCV) |
| a substitution of the amino acid sequence VCV for the GV between positions 776 and 777 |
| a substitution of the amino acid sequence PK for the LRE between positions 755 and 757 |
| a substitution of the amino acid sequence CV for the G at position 776 |
| a substitution of the amino acid sequence AVCGG for the GVG between positions 776 and 778 |
| a substitution of the amino acid sequence CVCG for the GVG between positions 776 and 778 |
| a substitution of the amino acid sequence VVVG for the GVG between positions 776 and 778 |
| a substitution of the amino acid sequence SVGG for the GVGS between positions 776 and 779 |
| a substitution of the amino acid sequence VVGES for the GVGS between positions 776 and 779 |
| a substitution of the amino acid sequence AVGSGV for the GV between positions 776 and 777 |
| a substitution of the amino acid sequence CVC for the GV between positions 776 and 777 |
| a substitution of the amino acid sequence HVC for the GV between positions 776 and 777 |
| a substitution of the amino acid sequence VAAGV for the GV between positions 776 and 777 |
| a substitution of the amino acid sequence VAGV for the GV between positions 776 and 777 |
| a substitution of the amino acid sequence VVV for the GV between positions 776 and 777 |
| a substitution of the amino acid sequence VPS for the VLRE between positions 754 and 757 |

In some embodiments, the oncogenic variant of HER2 is any of the HER2 variants put forth in Table 6.

TABLE 6

| HER2 Oncogenic Variants | | |
|---|---|---|
| HER2-S310F | HER2-G58R | HER2-V659E |
| HER2-S310Y | HER2-R103Q | HER2-G660D |
| HER2-R678Q | HER2-P122L | HER2-Q709L |
| HER2-V777L | HER2-V219I | HER2-T733I |
| HER2-V777M | HER2-G292C | HER2-D769H |
| HER2-V842I | HER2-G292R | HER2-D769Y |
| HER2-L755A | HER2-A293T | HER2-G776A |
| HER2-L755P | HER2-R434Q | HER2-G776V |
| HER2-L755S | HER2-A510T | HER2-V773M |
| HER2-Δ16 | HER2-A588V | HER2-T862A |
| HER2-C311R | HER2-G603C | HER2-L869R |
| p95-HER2-M611 | HER2-E645K | HER2-H878Y |
| HER2-A232V | HER2-G229R | HER2-A516T |
| HER2-E717V | HER2-R1230Q | |

In some embodiments, the cancer, or a tumor or cell thereof, expresses an oncogenic variant of a HER3 receptor. In some embodiments, the oncogenic variant of HER3 is any of the variants put forth in Table 7.

TABLE 7

| HER3 Oncogenic Variants |
|---|
| HER3-V104M |
| HER3-A232V |
| HER3-G284R |
| HER3-D297Y |
| HER3-E928G |

In some embodiments, the cancer, or a tumor or a cell thereof, expresses an oncogenic variant of a HER4 receptor. In some embodiments, the oncogenic variant of the HER4 receptor is an allosteric variant of the HER4 receptor. In some embodiments, the oncogenic variant of a HER4 receptor comprises deletion of exon 16 (HER4-Δ16).

In some embodiments, the cancer, or a tumor or a cell thereof, expresses an oncogenic variant of an EGFR, wherein the sequence encoding the oncogenic variant of the EGFR comprises a deletion of exon 20 or a portion thereof and wherein the cancer, the tumor or the cell thereof does not comprise a second oncogenic variation in a sequence other than exon 20 of EGFR. In some embodiments, the second oncogenic variation comprises a sequence encoding one or more of an EGFR kinase domain (KD), BRAF, NTRK, and KRAS.

In some embodiments, the cancer, or a tumor or a cell thereof, expresses an oncogenic variant of an EGFR, wherein the sequence encoding the oncogenic variant of the EGFR comprises a deletion of exon 20 or a portion thereof and wherein the cancer, the tumor or the cell thereof does not comprise a marker indicating responsiveness to immunotherapy.

In some embodiments, the oncogenic variant (e.g., allosteric variant) or the oncogenic mutation (e.g., allosteric mutation) is detected by a Food and Drug Administration (FDA)-approved diagnosis.

In some embodiments, the cancer, or a tumor or a cell thereof, expresses an oncogenic variant of a phosphatidylinositol-3-kinase (PI3K). In some embodiments, the cancer, or a tumor or cell thereof, expresses a mutant form of a PI3K, wherein the mutant form of the PI3K differs from the wildtype sequence of the PI3K. In some embodiments, the cancer is glioblastoma, and the cancer, or a tumor or cell thereof, expresses an oncogenic variant of a PI3K. In some embodiments, the cancer is glioblastoma, and the cancer, or a tumor or cell thereof, expresses a mutant form of a PI3K, wherein the mutant form of the PI3K differs from the wildtype sequence of the PI3K.

It is understood that an oncogenic variant of a PI3K is a PI3K protein that comprises at least one oncogenic mutation and that is produced as the result of the expression of a gene encoding the PI3K that comprises at least one oncogenic mutation.

As would be appreciated by the skilled artisan, in the context of a gene (e.g. a gene encoding a PI3K), an oncogenic mutation can include, but is not limited to a mutation that results in the substitution of one amino acid for another at a specific position within a PI3K, a mutation that results in an insertion of one or more amino acids between two positions within PI3K, a mutation that results in the deletion of one more amino acids between two positions within a PI3K, and a mutation that results in a fusion of a PI3K or portion thereof, with another protein, or portion thereof. As would be appreciated by the skilled artisan, in the context of a gene, an oncogenic mutation can include, but is not limited to, a missense mutation, a nonsynonymous mutation, an insertion of one or more nucleotides, a deletion of one or more nucleotides, an inversion and a deletion-insertion.

As would be appreciated by the skilled artisan, in the context of a protein (e.g. a PI3K), an oncogenic mutation can include, but is not limited to, the substitution of one amino acid for another at a specific position within a PI3K, an insertion of one or more amino acids between two positions within a PI3K, a deletion of one more amino acids between two positions within a PI3K, and a fusion of a PI3K, or portion thereof, with another protein, or portion thereof.

In some embodiments, the cancer, or a tumor or cell thereof, has an amplification of the MET gene, which encodes the receptor tyrosine kinase c-MET (also referred to as MET).

In some aspects, the cancer is glioblastoma, and the cancer, or a tumor or cell thereof, expresses EGFRvIII. In some aspects, the cancer is glioblastoma, and the cancer, or a tumor or cell thereof, expresses EGFRvII. In some aspects, the cancer is glioblastoma, and the cancer, or a tumor or cell thereof, expresses EGFRvVI. In some aspects, the cancer is glioblastoma, and the cancer, or a tumor or cell thereof, expresses EGFR-R108K. In some aspects, the cancer is glioblastoma, and the cancer, or a tumor or cell thereof, expresses EGFR-R222C. In some aspects, the cancer is glioblastoma, and the cancer, or a tumor or cell thereof, expresses EGFR-C231F. In some aspects, the cancer is glioblastoma, and the cancer, or a tumor or cell thereof, expresses EGFR-A289T. In some aspects, the cancer is glioblastoma, and the cancer, or a tumor or cell thereof, expresses EGFR-A289V. In some aspects, the cancer is glioblastoma, and the cancer, or a tumor or cell thereof, expresses EGFR-0595S. In some aspects, the cancer is glioblastoma, and the cancer, or a tumor or cell thereof, expresses EGFR-G598V. In some aspects, the cancer is glioblastoma, and the cancer, or a tumor or cell thereof, expresses EGFR-S645C. In some aspects, the cancer is NSCLC, and the cancer, or a tumor or cell thereof expresses EGFR-C797S. some aspects, the cancer is NSCLC, and the cancer, or a tumor or cell thereof expresses EGFR-G719S. In some aspects, the cancer is advanced and/or metastatic NSCLC, and the cancer, or a tumor or cell thereof expresses EGFR-C797S. In some aspects, the cancer is advanced and/or metastatic NSCLC, and the cancer, or a tumor or cell thereof expresses EGFR-G719S. In some aspects, the cancer is NSCLC, and the cancer, or a tumor or cell thereof, expresses EGFR-C797S, wherein the cancer, or a tumor or cell thereof, is insensitive or resistant to treatment with a therapeutic agent different from the compound of the present disclosure (e.g., osimertinib or lazertinib). In some aspects, the cancer is NSCLC, and the cancer, or a tumor or cell thereof, expresses EGFR-C797S as a resistance mechanism, wherein the cancer, or a tumor or cell thereof, is insensitive or resistant to treatment with a therapeutic agent different from the compound of the present disclosure (e.g., osimertinib or lazertinib).

In some aspects, a deletion of exon 19 can comprise a deletion of E746-A750 (EGFR-E746-A750del).

In some aspects, the cancer is NSCLC, and the cancer, or a tumor or cell thereof, expresses an oncogenic variant of EGFR comprising a deletion of exon 19. In some aspects, the deletion of exon 19 is a deletion of E746-A750 (EGFR-E746-A750del).

In some aspects, the cancer is NSCLC, and the cancer, or a tumor or cell thereof, expresses an oncogenic variant of EGFR comprising a deletion of exon 19+C797S. In some aspects, the deletion of exon 19 is a deletion of E746-A750 (EGFR-E746-A750del).

In some aspects, the cancer is NSCLC, and the cancer, or a tumor or cell thereof, expresses an oncogenic variant of EGFR comprising a deletion of exon 19+C797S, wherein the cancer, or a tumor or cell thereof, is insensitive or resistant to treatment with a therapeutic agent different from the compound of the present disclosure (e.g., osimertinib or lazertinib). In some aspects, the deletion of exon 19 is a deletion of E746-A750 (EGFR-E746-A750del). In some aspects, the cancer is NSCLC, and the cancer, or a tumor or cell thereof, expresses EGFR-L858R.

In some aspects, the cancer is NSCLC, and the cancer, or a tumor or cell thereof, expresses EGFR-C797S+L858R.

In some aspects, the cancer is NSCLC, and the cancer, or a tumor or cell thereof, expresses EGFR-C797S+L858R, wherein the cancer, or a tumor or cell thereof, is insensitive or resistant to treatment with a therapeutic agent different from the compound of the present disclosure (e.g., osimertinib or lazertinib).

In some aspects, the cancer is NSCLC, and the cancer, or a tumor or cell thereof, expresses an oncogenic variant of EGFR comprising an oncogenic mutation in Exon 18.

In some aspects, the cancer is NSCLC, and the cancer, or a tumor or cell thereof, expresses EGFR-G719C, EGFR-G719D, EGFR-G719R, EGFR-G719A, or EGFR-G719S.

In some aspects, the cancer is NSCLC, and the cancer, or a tumor or cell thereof, expresses EGFR-G719C, EGFR-G719D, EGFR-G719R, EGFR-G719A, EGFR-G719S, EGFR-S768I, EGFR-V769L, EGFR-E709G, EGFR-E709A, EGFR-D716Y or any combination thereof.

In some aspects, the cancer is NSCLC, and the cancer, or a tumor or cell thereof, expresses EGFR-S768I.

In some aspects, the cancer is NSCLC, and the cancer, or a tumor or cell thereof, expresses EGFR-L861Q.

In some aspects, the cancer is NSCLC, and the cancer, or a tumor or cell thereof, has an amplification of the MET gene.

In some embodiments, prior to the treatment with the compound of the present disclosure, the subject has not undergone any surgery for treating the cancer.

In some embodiments, prior to the treatment with the compound of the present disclosure, the subject has undergone one or more surgeries for treating the cancer.

In some embodiments, prior to the treatment with the compound of the present disclosure, the subject has received at least one chemoradiotherapy.

In some embodiments, the subject has recurrent GBM and has previously undergone one or more surgeries and have received at least one chemoradiotherapy.

In some embodiments, prior to the treatment with the compound of the present disclosure, the subject is treated with a therapeutic agent different from the compound of the present disclosure.

In some embodiments, the cancer, or a tumor or a cell thereof, is insensitive or resistant to treatment with a third-generation EGFR inhibitor.

In some embodiments, the cancer, or a tumor or a cell thereof, is insensitive or resistant to treatment with an EGFR inhibitor different from a compound of the present disclosure.

A non-exhaustive and non-limiting list of third-generation EGFR inhibitors consists of afatinib, avitinib, dacomitinib, erlotinib, gefitinib, lazertinib, mavelertinib, naquotinib, nazartinib, olmutinib, osimertinib, and rociletinib.

In some embodiments, the cancer, or a tumor or a cell thereof, is insensitive or resistant to treatment with one or more of afatinib, avitinib, dacomitinib, erlotinib, gefitinib, lazertinib, mavelertinib, naquotinib, nazartinib, olmutinib, osimertinib, and rociletinib.

In some embodiments, the cancer, or a tumor or a cell thereof, is insensitive or resistant to treatment with osimertinib or lazertinib.

In some embodiments, the cancer is NSCLC and is insensitive or resistant to treatment with a third-generation EGFR inhibitor. In some embodiments, the cancer is NSCLC and is insensitive or resistant to treatment with a third-generation EGFR inhibitor in combination with a platinum containing chemotherapy.

In some embodiments, the cancer is NSCLC and is insensitive or resistant to treatment with a third-generation EGFR inhibitor, and wherein the cancer, or a tumor or cell thereof, expresses at least one oncogenic variant of EGFR. In some embodiments, the cancer is NSCLC and is insensitive or resistant to treatment with a third-generation EGFR inhibitor in combination with a platinum containing chemotherapy, and wherein the cancer, or a tumor or cell thereof, expresses at least one oncogenic variant of EGFR. In some embodiments, the oncogenic variant of EGFR can be EGFR-C797S, EGFR-L861Q, EGFR-G719C, EGFR-G719D, EGFR-G719R, EGFR-G719A, EGFR-G719S, EGFR-S768I or EGFR-V769L.

In some embodiments, the cancer is advanced and/or metastatic NSCLC and is insensitive or resistant to treatment with a third-generation EGFR inhibitor. In some embodiments, the cancer is advanced and/or metastatic NSCLC and is insensitive or resistant to treatment with a third-generation EGFR inhibitor in combination with a platinum containing chemotherapy.

In some embodiments, the cancer is advanced and/or metastatic NSCLC and is insensitive or resistant to treatment with a third-generation EGFR inhibitor, and wherein the cancer, or a tumor or cell thereof, expresses at least one oncogenic variant of EGFR. In some embodiments, the cancer is advanced and/or metastatic NSCLC and is insensitive or resistant to treatment with a third-generation EGFR inhibitor in combination with a platinum containing chemotherapy, and wherein the cancer, or a tumor or cell thereof, expresses at least one oncogenic variant of EGFR. In some embodiments, the oncogenic variant of EGFR can be EGFR-C797S, EGFR-L861Q, EGFR-G719C, EGFR-G719D, EGFR-G719R, EGFR-G719A, EGFR-G719S, EGFR-S768I or EGFR-V769L.

In some embodiments, the cancer is NSCLC and is insensitive or resistant to treatment with one or more of afatinib, avitinib, dacomitinib, erlotinib, gefitinib, lazertinib, mavelertinib, naquotinib, nazartinib, olmutinib, osimertinib, and rociletinib.

In some embodiments, the cancer is NSCLC and is insensitive or resistant to treatment with osimertinib or lazertinib.

In some embodiments, the cancer, or a tumor or a cell thereof, is insensitive or resistant to treatment with a therapeutic agent different from the compound of the present disclosure. In some embodiments, the cancer, or a tumor or a cell thereof, is insensitive or resistant to treatment with a Type I inhibitor. In some embodiments, the cancer, or a tumor or a cell thereof, is insensitive or resistant to treatment with one or more of gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 and AZD9291.

In some embodiments, the subject has an adverse reaction to treatment with a therapeutic agent different from the compound of the present disclosure. In some embodiments, the subject has an adverse reaction to treatment with a Type I inhibitor. In some embodiments, the subject has an adverse reaction to treatment with one or more of gefinitinib, erlotinib, afatinib, osimertinib, necitunumab, crizotinib, alectinib, ceritinib, dabrafenib, trametinib, afatinib, sapitinib, dacomitinib, canertinib, pelitinib, WZ4002, WZ8040, WZ3146, CO-1686 and AZD9291. In some embodiments, the adverse reaction is an activation of the oncogenic variant of an EGFR and wherein the oncogenic variant comprises a mutation in an extracellular domain of the receptor. In some embodiments, the adverse reaction is an activation of the oncogenic variant of a HER2 Receptor and wherein the oncogenic variant comprises a mutation in an extracellular domain of the receptor.

In some embodiments, the subject has been previously administered at least one initial therapy that is different from a compound of the present disclosure, and the subject has experienced disease progression despite the administration of said at least one initial therapy, wherein the initial therapy comprises the administration of at least one EGFR inhibitor different from a compound of the present disclosure, at least one platinum containing chemotherapy, at least one anti-PD-L1 therapy or any combination thereof.

In some embodiments, the subject can have NSCLC and the subject has been previously administered at least one initial therapy that is different from a compound of the present disclosure for the treatment of said NSCLC, and the subject has experienced disease progression despite the administration of said at least one initial therapy, wherein the initial therapy comprises the administration of at least one EGFR inhibitor different from a compound of the present disclosure, at least one platinum containing chemotherapy, at least one anti-PD-L1 therapy or any combination thereof.

In some embodiments, the subject has advanced and/or metastatic NSCLC, wherein the NSCLC, or a tumor or cell thereof, expresses at least one oncogenic variant of EGFR, and wherein the subject has been previously administered at least one EGFR inhibitor different from a compound of the present disclosure in combination with at least one platinum containing chemotherapy. In some embodiments, the subject has advanced and/or metastatic NSCLC, wherein the NSCLC, or a tumor or cell thereof, expresses at least one oncogenic variant of EGFR, and wherein the subject has been previously administered at least one EGFR inhibitor different from a compound of the present disclosure in combination with at least one platinum containing chemotherapy and at least one anti-PD-L1 therapy. In some embodiments, the at least one EGFR inhibitor can be Osimertinib. In some aspects, the at least one oncogenic variant of EGFR can be EGFR-Δ19, EGFR-L858R, EGFR-L861Q, EGFR-G719C, EGFR-G719D, EGFR-G719R, EGFR-G719A, EGFR-G719S, EGFR-S768I, EGFR-V769L or EGFR-C797S.

In some embodiments, the subject has advanced and/or metastatic NSCLC, wherein the NSCLC, or a tumor or cell thereof, expresses at least one oncogenic variant of EGFR, and wherein the subject has been previously administered at least one EGFR inhibitor different from a compound of the present disclosure in combination with at least one platinum containing chemotherapy. In some embodiments, the subject has advanced and/or metastatic NSCLC, wherein the NSCLC, or a tumor or cell thereof, expresses at least one oncogenic variant of EGFR, and wherein the subject has been previously administered at least one EGFR inhibitor different from a compound of the present disclosure in combination with at least one platinum containing chemotherapy and at least one anti-PD-L1 therapy. In some embodiments, the at least one EGFR inhibitor can be Osimertinib. In some aspects, the at least one oncogenic variant of EGFR can be EGFR-G719C, EGFR-G719D, EGFR-G719R, EGFR-G719A, EGFR-G719S, EGFR-S768I, EGFR-V769L, EGFR-E709G, EGFR-E709A or EGFR-D716Y. In some embodiments, the NSCLC can have metastasized to the CNS. In some embodiments, the NSCLC can have not metastasized to the CNS.

In some embodiments, the subject has advanced and/or metastatic NSCLC, wherein the NSCLC, or a tumor or cell thereof, expresses at least one oncogenic variant of EGFR, wherein the at least one oncogenic variant of EGFR is EGFR-C797S, and wherein the subject has been previously administered at least one EGFR inhibitor different from a compound of the present disclosure in combination with at least one platinum containing chemotherapy. In some embodiments, the subject has advanced and/or metastatic NSCLC, wherein the NSCLC, or a tumor or cell thereof, expresses at least one oncogenic variant of EGFR, wherein the at least one oncogenic variant of EGFR is EGFR-C797S, and wherein the subject has been previously administered at least one EGFR inhibitor different from a compound of the present disclosure in combination with at least one platinum containing chemotherapy and at least one anti-PD-L1 therapy. In some embodiments, the at least one EGFR inhibitor can be Osimertinib. In some embodiments, the NSCLC can have metastasized to the CNS. In some embodiments, the NSCLC can have not metastasized to the CNS.

In some embodiments, the subject has advanced and/or metastatic NSCLC, wherein the NSCLC, or a tumor or cell thereof, expresses at least one oncogenic variant of EGFR, and wherein the subject has been previously administered at least one platinum containing chemotherapy. In some embodiments, the subject has advanced and/or metastatic NSCLC, wherein the NSCLC, or a tumor or cell thereof, expresses at least one oncogenic variant of EGFR, and wherein the subject has been previously administered at least one platinum containing chemotherapy in combination with at least one anti-PD-L1 therapy. In some embodiments, the at least one oncogenic variant of EGFR can be EGFR-G719C, EGFR-G719D, EGFR-G719R, EGFR-G719A, or EGFR-G719S. In some embodiments, the NSCLC can have metastasized to the CNS. In some embodiments, the NSCLC can have not metastasized to the CNS.

Non-limiting examples of anti-PD-L1 therapy can include, but are not limited to, anti-PD-L1 antibodies known in the art (e.g. atezolizumab, avelumab, and durvalumab).

In some embodiments, the method further comprises administering to the subject in need thereof a therapeutically effective amount of a non-Type I inhibitor. In some embodiments, the non-Type I inhibitor comprises a small molecule Type II inhibitor.

In some embodiments, the method further comprises administering to the subject in need thereof a therapeutically effective amount of a non-Type I inhibitor. In some embodiments, the non-Type I inhibitor comprises a small molecule Type II inhibitor.

In some embodiments, the compound is used in combination with a therapeutically effective amount of a non-Type I inhibitor. In some embodiments, the non-Type I inhibitor comprises a small molecule Type II inhibitor.

In some embodiments, the composition further comprises a non-Type I inhibitor. In some embodiments, the non-Type I inhibitor comprises a small molecule Type II inhibitor.

In some embodiments, the method further comprises administering to the subject in need thereof a therapeutically effective amount of temozolomide.

In some embodiments, the compound is administered in combination with a therapeutically effective amount of temozolomide.

In some embodiments, the composition further comprises temozolomide.

In some embodiments, the compound is administered in combination with a therapeutically effective amount of a phosphatidylinositol-3-kinase (PI3K) inhibitor.

In some embodiments, the compound is administered in combination with a therapeutically effective amount of a phosphatidylinositol-3-kinase (PI3K) inhibitor.

In some embodiments, the composition further comprises a phosphatidylinositol-3-kinase (PI3K) inhibitor.

In some embodiments, the method further comprises administering to the subject in need thereof a therapeutically effective amount of amivantamab, capmatinib, or a combination thereof.

In some embodiments, the compound is administered in combination with a therapeutically effective amount of amivantamab, capmatinib, or a combination thereof.

In some embodiments, the composition further comprises amivantamab, capmatinib, or a combination thereof.

In some embodiments, the method further comprises administering to the subject in need thereof a therapeutically effective amount of osimertinib.

In some embodiments, the compound is administered in combination with a therapeutically effective amount of osimertinib.

In some embodiments, the composition further comprises osimertinib.

In some embodiments, the method further comprises administering to the subject in need thereof a therapeutically effective amount of alpelisib.

In some embodiments, the compound is administered in combination with a therapeutically effective amount of alpelisib.

In some embodiments, the composition further comprises alpelisib.

In some embodiments, the method further comprises administering to the subject in need thereof a therapeutically effective amount of paxalisib.

In some embodiments, the compound is administered in combination with a therapeutically effective amount of paxalisib.

In some embodiments, the composition further comprises paxalisib.

In some embodiments, the therapeutically effective amount reduces a severity of a sign or symptom of the cancer.

In some embodiments, the sign of the cancer comprises a tumor grade and wherein a reduction of the severity of the sign comprises a decrease of the tumor grade.

In some embodiments, the sign of the cancer comprises a tumor metastasis and wherein a reduction of the severity of the sign comprises an elimination of the metastasis or a reduction in the rate or extent the metastasis.

In some embodiments, the sign of the cancer comprises a tumor volume and wherein a reduction of the severity of the sign comprises an elimination of the tumor or a reduction in the volume.

In some embodiments, the symptom of the cancer comprises pain and wherein a reduction of the severity of the sign comprises an elimination or a reduction in the pain.

In some embodiments, the therapeutically effective amount induces a period of remission.

In some embodiments, the therapeutically effective amount improves a prognosis of the subject.

Such a use (or method of prevention or treatment) of a subject comprises administering to a subject in need of such prevention or treatment a therapeutically effective amount of a compound of the disclosure or pharmaceutically acceptable salts thereof or a pharmaceutical composition thereof by targeting allosteric and/or oncogenic variants of EGFR and HER2 receptor.

Administration of Compound No. 1

In some embodiments, the subject is a human.

In some embodiments, Compound No. 1 (e.g., Compound No. 1A or Compound No. 1B) or the pharmaceutically acceptable salt thereof is orally administered.

In some embodiments, Compound No. 1 (e.g., Compound No. 1A or Compound No. 1B) or the pharmaceutically acceptable salt thereof is administered at a dosage (e.g., a daily dosage) of:

- about 15±10 mg, about 15±5 mg, about 15±4 mg, about 15±3 mg, about 15±2 mg, or about mg (e.g., about 15 mg);
- about 25±10 mg, about 25±5 mg, about 25±4 mg, about 25±3 mg, about 25±2 mg, or about mg (e.g., about 25 mg);
- about 50±10 mg, about 50±5 mg, about 50±4 mg, about 50±3 mg, about 50±2 mg, or about mg (e.g., about 50 mg);
- about 100±20 mg, about 100±10 mg, about 100±5 mg, about 100±4 mg, about 100±3 mg, about 100±2 mg, or about 100±1 mg (e.g., about 100 mg);
- about 150±20 mg, about 150±10 mg, about 150±5 mg, about 150±4 mg, about 150±3 mg, about 150±2 mg, or about 150±1 mg (e.g., about 150 mg); about 200±20 mg, about 200±10 mg, about 200±5 mg, about 200±4 mg, about 200±3 mg, about 200±2 mg, or about 200±1 mg (e.g., about 200 mg);
- about 300±20 mg, about 300±10 mg, about 300±5 mg, about 300±4 mg, about 300±3 mg, about 300±2 mg, or about 300±1 mg (e.g., about 300 mg);
- about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg);
- about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg);
- about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg);
- about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg); or about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

In some embodiments, Compound No. 1 (e.g., Compound No. 1A or Compound No. 1B) or the pharmaceutically acceptable salt thereof is administered at a dosage (e.g., a daily dosage) of about 15±10 mg, about 15±5 mg, about 15±4 mg, about 15±3 mg, about 15±2 mg, or about 15±1 mg (e.g., about 15 mg).

In some embodiments, Compound No. 1 (e.g., Compound No. 1A or Compound No. 1B) or the pharmaceutically acceptable salt thereof is administered at a dosage (e.g., a daily dosage) of about 25±10 mg, about 25±5 mg, about 25±4 mg, about 25±3 mg, about 25±2 mg, or about 25±1 mg (e.g., about 25 mg).

In some embodiments, Compound No. 1 (e.g., Compound No. 1A or Compound No. 1B) or the pharmaceutically acceptable salt thereof is administered at a dosage (e.g., a daily dosage) of about 50±10 mg, about 50±5 mg, about 50±4 mg, about 50±3 mg, about 50±2 mg, or about 50±1 mg (e.g., about 50 mg).

In some embodiments, Compound No. 1 (e.g., Compound No. 1A or Compound No. 1B) or the pharmaceutically acceptable salt thereof is administered at a dosage (e.g., a daily dosage) of about 100±20 mg, about 100±10 mg, about 100±5 mg, about 100±4 mg, about 100±3 mg, about 100±2 mg, or about 100±1 mg (e.g., about 100 mg).

In some embodiments, Compound No. 1 (e.g., Compound No. 1A or Compound No. 1B) or the pharmaceutically acceptable salt thereof is administered at a dosage (e.g., a daily dosage) of about 150±20 mg, about 150±10 mg, about 150±5 mg, about 150±4 mg, about 150±3 mg, about 150±2 mg, or about 150±1 mg (e.g., about 150 mg).

In some embodiments, Compound No. 1 (e.g., Compound No. 1A or Compound No. 1B) or the pharmaceutically acceptable salt thereof is administered at a dosage (e.g., a daily dosage) of about 200±20 mg, about 200±10 mg, about 200±5 mg, about 200±4 mg, about 200±3 mg, about 200±2 mg, or about 200±1 mg (e.g., about 200 mg).

In some embodiments, Compound No. 1 (e.g., Compound No. 1A or Compound No. 1B) or the pharmaceutically acceptable salt thereof is administered at a dosage (e.g., a daily dosage) of about 300±20 mg, about 300±10 mg, about 300±5 mg, about 300±4 mg, about 300±3 mg, about 300±2 mg, or about 300±1 mg (e.g., about 300 mg).

In some embodiments, Compound No. 1 (e.g., Compound No. 1A or Compound No. 1B) or the pharmaceutically acceptable salt thereof is administered at a dosage (e.g., a daily dosage) of about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg).

In some embodiments, Compound No. 1 (e.g., Compound No. 1A or Compound No. 1B) or the pharmaceutically acceptable salt thereof is administered at a dosage (e.g., a daily dosage) of about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg).

In some embodiments, Compound No. 1 (e.g., Compound No. 1A or Compound No. 1B) or the pharmaceutically acceptable salt thereof is administered at a dosage (e.g., a daily dosage) of about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg).

In some embodiments, Compound No. 1 (e.g., Compound No. 1A or Compound No. 1B) or the pharmaceutically acceptable salt thereof is administered at a dosage (e.g., a daily dosage) of about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg).

In some embodiments, Compound No. 1 (e.g., Compound No. 1A or Compound No. 1B) or the pharmaceutically acceptable salt thereof is administered at a dosage (e.g., a daily dosage) of about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

In some embodiments, Compound No. 1 (e.g., Compound No. 1A or Compound No. 1B) or the pharmaceutically acceptable salt thereof is administered at a dosage (e.g., a daily dosage) of:

about 60±10 mg/kg, about 60±5 mg/kg, about 60±4 mg/kg, about 60±3 mg/kg, about 60±2 mg/kg, or about 60±1 mg/kg (e.g., about 60 mg/kg);

about 180±20 mg/kg, about 180±10 mg/kg, about 180±5 mg/kg, about 180±4 mg/kg, about 180±3 mg/kg, about 180±2 mg/kg, or about 180±1 mg/kg (e.g., about 180 mg/kg);

about 600±50 mg/kg, about 600±40 mg/kg, about 600±30 mg/kg, about 600±20 mg/kg, about 600±10 mg/kg, about 600±5 mg/kg, about 600±4 mg/kg, about 600±3 mg/kg, about 600±2 mg/kg, or about 600±1 mg/kg (e.g., about 600 mg/kg); or about 1800±50 mg/kg, about 1800±40 mg/kg, about 1800±30 mg/kg, about 1800±20 mg/kg, about 1800±10 mg/kg, about 1800±5 mg/kg, about 1800±4 mg/kg, about 1800±3 mg/kg, about 1800±2 mg/kg, or about 1800±1 mg/kg (e.g., about 1800 mg/kg).

In some embodiments, Compound No. 1 (e.g., Compound No. 1A or Compound No. 1B) or the pharmaceutically acceptable salt thereof is administered at a dosage (e.g., a daily dosage) of about 60±10 mg/kg, about 60±5 mg/kg, about 60±4 mg/kg, about 60±3 mg/kg, about 60±2 mg/kg, or about 60±1 mg/kg (e.g., about 60 mg/kg).

In some embodiments, Compound No. 1 (e.g., Compound No. 1A or Compound No. 1B) or the pharmaceutically acceptable salt thereof is administered at a dosage (e.g., a daily dosage) of about 180±20 mg/kg, about 180±10 mg/kg, about 180±5 mg/kg, about 180±4 mg/kg, about 180±3 mg/kg, about 180±2 mg/kg, or about 180±1 mg/kg (e.g., about 180 mg/kg).

In some embodiments, Compound No. 1 (e.g., Compound No. 1A or Compound No. 1B) or the pharmaceutically acceptable salt thereof is administered at a dosage (e.g., a daily dosage) of about 600±50 mg/kg, about 600±40 mg/kg, about 600±30 mg/kg, about 600±20 mg/kg, about 600±10 mg/kg, about 600±5 mg/kg, about 600±4 mg/kg, about 600±3 mg/kg, about 600±2 mg/kg, or about 600±1 mg/kg (e.g., about 600 mg/kg).

In some embodiments, Compound No. 1 (e.g., Compound No. 1A or Compound No. 1B) or the pharmaceutically acceptable salt thereof is administered at a dosage (e.g., a daily dosage) of about 1800±50 mg/kg, about 1800±40 mg/kg, about 1800±30 mg/kg, about 1800±20 mg/kg, about 1800±10 mg/kg, about 1800±5 mg/kg, about 1800±4 mg/kg, about 1800±3 mg/kg, about 1800±2 mg/kg, or about 1800±1 mg/kg (e.g., about 1800 mg/kg).

In some embodiments, the subject is a mouse.

In some embodiments, the subject is a rat.

In some embodiments, the subject is a dog.

In some embodiments, Compound No. 1 (e.g., Compound No. 1A or Compound No. 1B) or the pharmaceutically acceptable salt thereof is administered at a dosage (e.g., a daily dosage) of:

about 1±3 mg/kg, about 1±2 mg/kg, about 1±1 mg/kg, or about 1±0.1 mg/kg (e.g., about 1 mg/kg);

about 5±3 mg/kg, about 5±2 mg/kg, or about 5±1 mg/kg (e.g., about 5 mg/kg);

about 15±5 mg/kg, about 15±4 mg/kg, about 15±3 mg/kg, about 15±2 mg/kg, or about mg/kg (e.g., about 15 mg/kg);

about 30±10 mg/kg, about 30±5 mg/kg, about 30±4 mg/kg, about 30±3 mg/kg, about 30±2 mg/kg, or about 30±1 mg/kg (e.g., about 30 mg/kg);

about 50±10 mg/kg, about 50±5 mg/kg, about 50±4 mg/kg, about 50±3 mg/kg, about 50±2 mg/kg, or about 50±1 mg/kg (e.g., about 50 mg/kg); or about 150±20 mg/kg, about 150±10 mg/kg, about 150±5 mg/kg, about 150±4 mg/kg, about 150±3 mg/kg, about 150±2 mg/kg, or about 150±1 mg/kg (e.g., about 150 mg/kg).

In some embodiments, Compound No. 1 (e.g., Compound No. 1A or Compound No. 1B) or the pharmaceutically acceptable salt thereof is administered at a dosage (e.g., a daily dosage) of about 1±3 mg/kg, about 1±2 mg/kg, about 1±1 mg/kg, or about 1±0.1 mg/kg (e.g., about 1 mg/kg).

In some embodiments, Compound No. 1 (e.g., Compound No. 1A or Compound No. 1B) or the pharmaceutically acceptable salt thereof is administered at a dosage (e.g., a daily dosage) of about 5±3 mg/kg, about 5±2 mg/kg, or about 5±1 mg/kg (e.g., about 5 mg/kg).

In some embodiments, Compound No. 1 (e.g., Compound No. 1A or Compound No. 1B) or the pharmaceutically acceptable salt thereof is administered at a dosage (e.g., a daily dosage) of about 15±5 mg/kg, about 15±4 mg/kg, about 15±3 mg/kg, about 15±2 mg/kg, or about 15±1 mg/kg (e.g., about 15 mg/kg).

In some embodiments, Compound No. 1 (e.g., Compound No. 1A or Compound No. 1B) or the pharmaceutically acceptable salt thereof is administered at a dosage (e.g., a daily dosage) of about 30±10 mg/kg, about 30±5 mg/kg, about 30±4 mg/kg, about 30±3 mg/kg, about 30±2 mg/kg, or about 30±1 mg/kg (e.g., about 30 mg/kg).

In some embodiments, Compound No. 1 (e.g., Compound No. 1A or Compound No. 1B) or the pharmaceutically acceptable salt thereof is administered at a dosage (e.g., a daily dosage) of about 50±10 mg/kg, about 50±5 mg/kg, about 50±4 mg/kg, about 50±3 mg/kg, about 50±2 mg/kg, or about 50±1 mg/kg (e.g., about 50 mg/kg).

In some embodiments, Compound No. 1 (e.g., Compound No. 1A or Compound No. 1B) or the pharmaceutically acceptable salt thereof is administered at a dosage (e.g., a daily dosage) of about 150±20 mg/kg, about 150±10 mg/kg, about 150±5 mg/kg, about 150±4 mg/kg, about 150±3 mg/kg, about 150±2 mg/kg, or about 150±1 mg/kg (e.g., about 150 mg/kg).

In some embodiments, Compound No. 1 (e.g., Compound No. 1A or Compound No. 1B) or the pharmaceutically acceptable salt thereof is administered with one or more drug holidays.

In some embodiments, Compound No. 1 (e.g., Compound No. 1A or Compound No. 1B) or the pharmaceutically acceptable salt thereof is administered without any drug holiday.

In some embodiments, prior to the administration, the subject is fasted for at least about 30 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, or at least about 12 hours.

In some embodiments, prior to the administration, the subject is fed with about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

Administration Lengths and Frequencies

In some embodiments, Compound No. 1 (e.g., Compound No. 1A or Compound No. 1B) or the pharmaceutically acceptable salt thereof is administered once daily.

In some embodiments, Compound No. 1 (e.g., Compound No. 1A or Compound No. 1B) or the pharmaceutically acceptable salt thereof is administered twice daily.

In some embodiments, Compound No. 1 (e.g., Compound No. 1A or Compound No. 1B) or the pharmaceutically acceptable salt thereof is administered for about 21 days, about 42 days, about 63 days, about 84 days, about 105 days, about 126 days, about 147 days, about 168 days, about 189 days, or about 210 days.

In some embodiments, Compound No. 1 (e.g., Compound No. 1A or Compound No. 1B) or the pharmaceutically acceptable salt thereof is administered for longer than 210 days.

In some embodiments, Compound No. 1 (e.g., Compound No. 1A or Compound No. 1B) or the pharmaceutically acceptable salt thereof is administered until a progression of cancer or an adverse effect (e.g., an intolerable toxicity) is observed.

In some embodiments, Compound No. 1 (e.g., Compound No. 1A or Compound No. 1B) or the pharmaceutically acceptable salt thereof is administered for about 21 days.

In some embodiments, Compound No. 1 (e.g., Compound No. 1A or Compound No. 1B) or the pharmaceutically acceptable salt thereof is administered for about 21 days, followed by a 30-day drug holiday.

In some embodiments, the treatment lasts about 1 month, about 2 months, about 3 months, about 6 months, about 9 months, about 12 months, about 15 months, about 18 months, about 21 months, or about 24 months.

In some embodiments, the treatment comprises one or more treatment cycles, wherein each treatment cycle comprises administering Compound No. 1 (e.g., Compound No. 1A or Compound No. 1B) or the pharmaceutically acceptable salt thereof for about 21 days, followed by a 30-day drug holiday.

Administrations of Compound No. 2

In some embodiments, the subject is a human.

In some embodiments, Compound No. 2 (e.g., Compound No. 2A or Compound No. 2B) or the pharmaceutically acceptable salt thereof is orally administered.

In some embodiments, Compound No. 2 (e.g., Compound No. 2A or Compound No. 2B) or the pharmaceutically acceptable salt thereof is administered at a dosage (e.g., a daily dosage) of:

- about 15±10 mg, about 15±5 mg, about 15±4 mg, about 15±3 mg, about 15±2 mg, or about mg (e.g., about 15 mg);
- about 25±10 mg, about 25±5 mg, about 25±4 mg, about 25±3 mg, about 25±2 mg, or about mg (e.g., about 25 mg);
- about 50±10 mg, about 50±5 mg, about 50±4 mg, about 50±3 mg, about 50±2 mg, or about mg (e.g., about 50 mg);
- about 100±20 mg, about 100±10 mg, about 100±5 mg, about 100±4 mg, about 100±3 mg, about 100±2 mg, or about 100±1 mg (e.g., about 100 mg);
- about 150±20 mg, about 150±10 mg, about 150±5 mg, about 150±4 mg, about 150±3 mg, about 150±2 mg, or about 150±1 mg (e.g., about 150 mg);
- about 200±20 mg, about 200±10 mg, about 200±5 mg, about 200±4 mg, about 200±3 mg, about 200±2 mg, or about 200±1 mg (e.g., about 200 mg);
- about 300±20 mg, about 300±10 mg, about 300±5 mg, about 300±4 mg, about 300±3 mg, about 300±2 mg, or about 300±1 mg (e.g., about 300 mg);
- about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg);
- about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg);
- about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg);
- about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg); or
- about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

In some embodiments, Compound No. 2 (e.g., Compound No. 2A or Compound No. 2B) or the pharmaceutically acceptable salt thereof is administered at a dosage (e.g., a daily dosage) of about 15±10 mg, about 15±5 mg, about 15±4 mg, about 15±3 mg, about 15±2 mg, or about 15±1 mg (e.g., about 15 mg).

In some embodiments, Compound No. 2 (e.g., Compound No. 2A or Compound No. 2B) or the pharmaceutically acceptable salt thereof is administered at a dosage (e.g., a daily dosage) of about 25±10 mg, about 25±5 mg, about 25±4 mg, about 25±3 mg, about 25±2 mg, or about 25±1 mg (e.g., about 25 mg).

In some embodiments, Compound No. 2 (e.g., Compound No. 2A or Compound No. 2B) or the pharmaceutically acceptable salt thereof is administered at a dosage (e.g., a daily dosage) of about 50±10 mg, about 50±5 mg, about 50±4 mg, about 50±3 mg, about 50±2 mg, or about 50±1 mg (e.g., about 50 mg).

In some embodiments, Compound No. 2 (e.g., Compound No. 2A or Compound No. 2B) or the pharmaceutically acceptable salt thereof is administered at a dosage (e.g., a daily dosage) of about 100±20 mg, about 100±10 mg, about 100±5 mg, about 100±4 mg, about 100±3 mg, about 100±2 mg, or about 100±1 mg (e.g., about 100 mg).

In some embodiments, Compound No. 2 (e.g., Compound No. 2A or Compound No. 2B) or the pharmaceutically acceptable salt thereof is administered at a dosage (e.g., a daily dosage) of about 150±20 mg, about 150±10 mg, about 150±5 mg, about 150±4 mg, about 150±3 mg, about 150±2 mg, or about 150±1 mg (e.g., about 150 mg).

In some embodiments, Compound No. 2 (e.g., Compound No. 2A or Compound No. 2B) or the pharmaceutically acceptable salt thereof is administered at a dosage (e.g., a daily dosage) of about 200±20 mg, about 200±10 mg, about 200±5 mg, about 200±4 mg, about 200±3 mg, about 200±2 mg, or about 200±1 mg (e.g., about 200 mg).

In some embodiments, Compound No. 2 (e.g., Compound No. 2A or Compound No. 2B) or the pharmaceutically acceptable salt thereof is administered at a dosage (e.g., a daily dosage) of about 300±20 mg, about 300±10 mg, about 300±5 mg, about 300±4 mg, about 300±3 mg, about 300±2 mg, or about 300±1 mg (e.g., about 300 mg).

In some embodiments, Compound No. 2 (e.g., Compound No. 2A or Compound No. 2B) or the pharmaceutically acceptable salt thereof is administered at a dosage (e.g., a daily dosage) of about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg).

In some embodiments, Compound No. 2 (e.g., Compound No. 2A or Compound No. 2B) or the pharmaceutically acceptable salt thereof is administered at a dosage (e.g., a daily dosage) of about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg).

In some embodiments, Compound No. 2 (e.g., Compound No. 2A or Compound No. 2B) or the pharmaceutically acceptable salt thereof is administered at a dosage (e.g., a daily dosage) of about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg).

In some embodiments, Compound No. 2 (e.g., Compound No. 2A or Compound No. 2B) or the pharmaceutically acceptable salt thereof is administered at a dosage (e.g., a daily dosage) of about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg).

In some embodiments, Compound No. 2 (e.g., Compound No. 2A or Compound No. 2B) or the pharmaceutically acceptable salt thereof is administered at a dosage (e.g., a daily dosage) of about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

In some embodiments, Compound No. 2 (e.g., Compound No. 2A or Compound No. 2B) or the pharmaceutically acceptable salt thereof is administered at a dosage (e.g., a daily dosage) of:

- about 60±10 mg/kg, about 60±5 mg/kg, about 60±4 mg/kg, about 60±3 mg/kg, about 60±2 mg/kg, or about 60±1 mg/kg (e.g., about 60 mg/kg);
- about 180±20 mg/kg, about 180±10 mg/kg, about 180±5 mg/kg, about 180±4 mg/kg, about 180±3 mg/kg, about 180±2 mg/kg, or about 180±1 mg/kg (e.g., about 180 mg/kg);
- about 600±50 mg/kg, about 600±40 mg/kg, about 600±30 mg/kg, about 600±20 mg/kg, about 600±10 mg/kg, about 600±5 mg/kg, about 600±4 mg/kg, about 600±3 mg/kg, about 600±2 mg/kg, or about 600±1 mg/kg (e.g., about 600 mg/kg); or
- about 1800±50 mg/kg, about 1800±40 mg/kg, about 1800±30 mg/kg, about 1800±20 mg/kg, about 1800±10 mg/kg, about 1800±5 mg/kg, about 1800±4 mg/kg, about 1800±3 mg/kg, about 1800±2 mg/kg, or about 1800±1 mg/kg (e.g., about 1800 mg/kg).

In some embodiments, Compound No. 2 (e.g., Compound No. 2A or Compound No. 2B) or the pharmaceutically acceptable salt thereof is administered at a dosage (e.g., a daily dosage) of about 60±10 mg/kg, about 60±5 mg/kg, about 60±4 mg/kg, about 60±3 mg/kg, about 60±2 mg/kg, or about 60±1 mg/kg (e.g., about 60 mg/kg).

In some embodiments, Compound No. 2 (e.g., Compound No. 2A or Compound No. 2B) or the pharmaceutically acceptable salt thereof is administered at a dosage (e.g., a daily dosage) of about 180±20 mg/kg, about 180±10 mg/kg, about 180±5 mg/kg, about 180±4 mg/kg, about 180±3 mg/kg, about 180±2 mg/kg, or about 180±1 mg/kg (e.g., about 180 mg/kg).

In some embodiments, Compound No. 2 (e.g., Compound No. 2A or Compound No. 2B) or the pharmaceutically acceptable salt thereof is administered at a dosage (e.g., a daily dosage) of about 600±50 mg/kg, about 600±40 mg/kg, about 600±30 mg/kg, about 600±20 mg/kg, about 600±10 mg/kg, about 600±5 mg/kg, about 600±4 mg/kg, about 600±3 mg/kg, about 600±2 mg/kg, or about 600±1 mg/kg (e.g., about 600 mg/kg).

In some embodiments, Compound No. 2 (e.g., Compound No. 2A or Compound No. 2B) or the pharmaceutically acceptable salt thereof is administered at a dosage (e.g., a daily dosage) of about 1800±50 mg/kg, about 1800±40 mg/kg, about 1800±30 mg/kg, about 1800±20 mg/kg, about 1800±10 mg/kg, about 1800±5 mg/kg, about 1800±4 mg/kg, about 1800±3 mg/kg, about 1800±2 mg/kg, or about 1800±1 mg/kg (e.g., about 1800 mg/kg).

In some embodiments, the subject is a mouse.

In some embodiments, the subject is a rat.

In some embodiments, the subject is a dog.

In some embodiments, Compound No. 2 (e.g., Compound No. 2A or Compound No. 2B) or the pharmaceutically acceptable salt thereof is administered at a dosage (e.g., a daily dosage) of:

- about 1±3 mg/kg, about 1±2 mg/kg, about 1±1 mg/kg, or about 1±0.1 mg/kg (e.g., about 1 mg/kg);
- about 5±3 mg/kg, about 5±2 mg/kg, or about 5±1 mg/kg (e.g., about 5 mg/kg);
- about 15±5 mg/kg, about 15±4 mg/kg, about 15±3 mg/kg, about 15±2 mg/kg, or about mg/kg (e.g., about 15 mg/kg);
- about 30±10 mg/kg, about 30±5 mg/kg, about 30±4 mg/kg, about 30±3 mg/kg, about 30±2 mg/kg, or about 30±1 mg/kg (e.g., about 30 mg/kg);
- about 50±10 mg/kg, about 50±5 mg/kg, about 50±4 mg/kg, about 50±3 mg/kg, about 50±2 mg/kg, or about 50±1 mg/kg (e.g., about 50 mg/kg); or
- about 150±20 mg/kg, about 150±10 mg/kg, about 150±5 mg/kg, about 150±4 mg/kg, about 150±3 mg/kg, about 150±2 mg/kg, or about 150±1 mg/kg (e.g., about 150 mg/kg).

In some embodiments, Compound No. 2 (e.g., Compound No. 2A or Compound No. 2B) or the pharmaceutically acceptable salt thereof is administered at a dosage (e.g., a daily dosage) of about 1±3 mg/kg, about 1±2 mg/kg, about 1±1 mg/kg, or about 1±0.1 mg/kg (e.g., about 1 mg/kg).

In some embodiments, Compound No. 2 (e.g., Compound No. 2A or Compound No. 2B) or the pharmaceutically acceptable salt thereof is administered at a dosage (e.g., a daily dosage) of about 5±3 mg/kg, about 5±2 mg/kg, or about 5±1 mg/kg (e.g., about 5 mg/kg).

In some embodiments, Compound No. 2 (e.g., Compound No. 2A or Compound No. 2B) or the pharmaceutically acceptable salt thereof is administered at a dosage (e.g., a daily dosage) of about 15±5 mg/kg, about 15±4 mg/kg, about 15±3 mg/kg, about 15±2 mg/kg, or about 15±1 mg/kg (e.g., about 15 mg/kg).

In some embodiments, Compound No. 2 (e.g., Compound No. 2A or Compound No. 2B) or the pharmaceutically acceptable salt thereof is administered at a dosage (e.g., a daily dosage) of about 30±10 mg/kg, about 30±5 mg/kg, about 30±4 mg/kg, about 30±3 mg/kg, about 30±2 mg/kg, or about 30±1 mg/kg (e.g., about 30 mg/kg).

In some embodiments, Compound No. 2 (e.g., Compound No. 2A or Compound No. 2B) or the pharmaceutically acceptable salt thereof is administered at a dosage (e.g., a daily dosage) of about 50±10 mg/kg, about 50±5 mg/kg, about 50±4 mg/kg, about 50±3 mg/kg, about 50±2 mg/kg, or about 50±1 mg/kg (e.g., about 50 mg/kg).

In some embodiments, Compound No. 2 (e.g., Compound No. 2A or Compound No. 2B) or the pharmaceutically acceptable salt thereof is administered at a dosage (e.g., a daily dosage) of about 150±20 mg/kg, about 150±10 mg/kg, about 150±5 mg/kg, about 150±4 mg/kg, about 150±3 mg/kg, about 150±2 mg/kg, or about 150±1 mg/kg (e.g., about 150 mg/kg).

In some embodiments, Compound No. 2 (e.g., Compound No. 2A or Compound No. 2B) or the pharmaceutically acceptable salt thereof is administered with one or more drug holidays.

In some embodiments, Compound No. 2 (e.g., Compound No. 2A or Compound No. 2B) or the pharmaceutically acceptable salt thereof is administered without any drug holiday.

In some embodiments, prior to the administration, the subject is fasted for at least about 30 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, or at least about 12 hours.

In some embodiments, prior to the administration, the subject is fed with about 30 minutes, about 1 hour, about 2 hours, about 3 hours, about 4 hours, about 5 hours, about 6 hours, about 7 hours, about 8 hours, about 9 hours, about 10 hours, about 11 hours, or about 12 hours.

Administration Lengths and Frequencies

In some embodiments, Compound No. 2 (e.g., Compound No. 2A or Compound No. 2B) or the pharmaceutically acceptable salt thereof is administered once daily.

In some embodiments, Compound No. 2 (e.g., Compound No. 2A or Compound No. 2B) or the pharmaceutically acceptable salt thereof is administered twice daily.

In some embodiments, Compound No. 2 (e.g., Compound No. 2A or Compound No. 2B) or the pharmaceutically acceptable salt thereof is administered for about 21 days, about 42 days, about 63 days, about 84 days, about 105 days, about 126 days, about 147 days, about 168 days, about 189 days, or about 210 days.

In some embodiments, Compound No. 2 (e.g., Compound No. 2A or Compound No. 2B) or the pharmaceutically acceptable salt thereof is administered for longer than 210 days.

In some embodiments, Compound No. 2 (e.g., Compound No. 2A or Compound No. 2B) or the pharmaceutically acceptable salt thereof is administered until a progression of cancer or an adverse effect (e.g., an intolerable toxicity) is observed.

In some embodiments, Compound No. 2 (e.g., Compound No. 2A or Compound No. 2B) or the pharmaceutically acceptable salt thereof is administered for about 21 days.

In some embodiments, Compound No. 2 (e.g., Compound No. 2A or Compound No. 2B) or the pharmaceutically acceptable salt thereof is administered for about 21 days, followed by a drug holiday.

In some embodiments, the treating or preventing lasts about 1 month, about 2 months, about 3 months, about 6 months, about 9 months, about 12 months, about 15 months, about 18 months, about 21 months, or about 24 months.

In some embodiments, the treating or preventing comprises one or more treatment cycles, wherein each treatment cycle comprises administering Compound No. 2 (e.g., Compound No. 2A or Compound No. 2B) or the pharmaceutically acceptable salt thereof for about 21 days, followed by a 30-day drug holiday.

Combination with Temozolomide (TMZ)

In some embodiments, the method further comprises administering a therapeutically effective amount of temozolomide.

In some embodiments, Compound No. 2 (e.g., Compound No. 2A or Compound No. 2B) or the pharmaceutically acceptable salt thereof is administered in combination with a therapeutically effective amount of temozolomide.

In some embodiments, Compound No. 2 (e.g., Compound No. 2A or Compound No. 2B), or the pharmaceutically acceptable salt thereof, and temozolomide are administered simultaneously, sequentially, or in alternation.

In some embodiments, Compound No. 2 (e.g., Compound No. 2A or Compound No. 2B), or the pharmaceutically acceptable salt thereof, and temozolomide are administered simultaneously.

In some embodiments, Compound No. 2 (e.g., Compound No. 2A or Compound No. 2B), or the pharmaceutically acceptable salt thereof, and temozolomide are administered sequentially.

In some embodiments, Compound No. 2 (e.g., Compound No. 2A or Compound No. 2B), or the pharmaceutically acceptable salt thereof, and temozolomide are administered temporal proximity.

In some embodiments, Compound No. 2 (e.g., Compound No. 2A or Compound No. 2B), or the pharmaceutically acceptable salt thereof, and temozolomide are administered in alternation.

In some embodiments, Compound No. 2 (e.g., Compound No. 2A or Compound No. 2B), or the pharmaceutically acceptable salt thereof, and temozolomide are administered in separate formulations.

In some embodiments, Compound No. 2 (e.g., Compound No. 2A or Compound No. 2B), or the pharmaceutically acceptable salt thereof, and temozolomide are administered in a co-formulation.

In some embodiments, Compound No. 2 (e.g., Compound No. 2A or Compound No. 2B), or the pharmaceutically acceptable salt thereof, and temozolomide are administered about 28 days.

In some embodiments, Compound No. 2 (e.g., Compound No. 2A or Compound No. 2B), or the pharmaceutically acceptable salt thereof, and temozolomide are administered about 28 days, about 56 days, about 84 days, about 112 days, about 140 days, about 168 days, about 196 days, about 224 days, about 252 days, or about 280 days.

In some embodiments, Compound No. 2 (e.g., Compound No. 2A or Compound No. 2B) or the pharmaceutically acceptable salt thereof is administered for longer than 280 days.

In some embodiments, Compound No. 2 (e.g., Compound No. 2A or Compound No. 2B) or the pharmaceutically acceptable salt thereof is administered until a progression of cancer or an adverse effect (e.g., an intolerable toxicity) is observed.

Exemplary Embodiments

Exemplary Embodiment No. 1. A method of treating or preventing cancer in a subject in need thereof, comprising administering to the subject a pharmaceutically effective amount of Compound No. 1, Compound No. 2, or a pharmaceutically acceptable salt thereof.

Exemplary Embodiment No. 2. A method of treating or preventing cancer in a subject in need thereof, comprising administering to the subject a pharmaceutically effective amount of Compound No. 1 or a pharmaceutically acceptable salt thereof.

Exemplary Embodiment No. 3. A method of treating or preventing cancer in a subject in need thereof, comprising administering to the subject a pharmaceutically effective amount of Compound No. 2 or a pharmaceutically acceptable salt thereof.

Exemplary Embodiment No. 4. Compound No. 1, Compound No. 2, or a pharmaceutically acceptable salt thereof for treating or preventing cancer in a subject in need thereof.

Exemplary Embodiment No. 5. Compound No. 1 or a pharmaceutically acceptable salt thereof for treating or preventing cancer in a subject in need thereof.

Exemplary Embodiment No. 6. Compound No. 2 or a pharmaceutically acceptable salt thereof for treating or preventing cancer in a subject in need thereof.

Exemplary Embodiment No. 7. Use of Compound No. 1, Compound No. 2, or a pharmaceutically acceptable salt thereof, in the manufacture of a medicament for treating or preventing cancer in a subject in need thereof.

Exemplary Embodiment No. 8. Use of Compound No. 1 or a pharmaceutically acceptable salt thereof, in the manufacture of a medicament for treating or preventing cancer in a subject in need thereof.

Exemplary Embodiment No. 9. Use of Compound No. 2 or a pharmaceutically acceptable salt thereof, in the manufacture of a medicament for treating or preventing cancer in a subject in need thereof.

Exemplary Embodiment No. 10. The method, compound, or use of any one of the preceding Embodiments, wherein the cancer is glioblastoma (GBM) or any subtype thereof.

Exemplary Embodiment No. 11. The method, compound, or use of any one of the preceding Embodiments, wherein the cancer is glioblastoma.

Exemplary Embodiment No. 12. The method, compound, or use of any one of the preceding Embodiments, wherein the cancer is non-small cell lung cancer (NSCLC) or any subtype thereof.

Exemplary Embodiment No. 13. The method, compound, or use of any one of the preceding Embodiments, wherein the cancer is non-small cell lung cancer (NSCLC).

Exemplary Embodiment No. 14. The method, compound, or use of any one of the preceding Embodiments, wherein Compound No. 1A, Compound No. 1B, or the pharmaceutically acceptable salt thereof is administered.

Exemplary Embodiment No. 15. The method, compound, or use of any one of the preceding Embodiments, wherein Compound No. 1A the pharmaceutically acceptable salt thereof is administered.

Exemplary Embodiment No. 16. The method, compound, or use of any one of the preceding Embodiments, wherein Compound No. 1B the pharmaceutically acceptable salt thereof is administered.

Exemplary Embodiment No. 17. The method, compound, or use of any one of the preceding Embodiments, wherein Compound No. 2A, Compound No. 2B, or the pharmaceutically acceptable salt thereof is administered.

Exemplary Embodiment No. 18. The method, compound, or use of any one of the preceding Embodiments, wherein Compound No. 2A the pharmaceutically acceptable salt thereof is administered.

Exemplary Embodiment No. 19. The method, compound, or use of any one of the preceding Embodiments, wherein Compound No. 2B the pharmaceutically acceptable salt thereof is administered.

Exemplary Embodiment No. 20. The method, compound, or use of any one of the preceding Embodiments, wherein the subject is a human.

Exemplary Embodiment No. 21. The method, compound, or use of any one of the preceding Embodiments, wherein the subject is a mouse.

Exemplary Embodiment No. 22. The method, compound, or use of any one of the preceding Embodiments, wherein Compound No. 1 or the pharmaceutically acceptable salt thereof is administered at a daily dosage of:

about 25±10 mg, about 25±5 mg, about 25±4 mg, about 25±3 mg, about 25±2 mg, or about mg (e.g., about 25 mg);

about 50±10 mg, about 50±5 mg, about 50±4 mg, about 50±3 mg, about 50±2 mg, or about mg (e.g., about 50 mg);

about 100±20 mg, about 100±10 mg, about 100±5 mg, about 100±4 mg, about 100±3 mg, about 100±2 mg, or about 100±1 mg (e.g., about 100 mg);

about 200±20 mg, about 200±10 mg, about 200±5 mg, about 200±4 mg, about 200±3 mg, about 200±2 mg, or about 200±1 mg (e.g., about 200 mg);

about 300±20 mg, about 300±10 mg, about 300±5 mg, about 300±4 mg, about 300±3 mg, about 300±2 mg, or about 300±1 mg (e.g., about 300 mg);

about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg);

about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg);

about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg);

about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg); or about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

Exemplary Embodiment No. 23. The method, compound, or use of any one of the preceding Embodiments, wherein Compound No. 1 or the pharmaceutically acceptable salt thereof is administered at a daily dosage of:

- about 60±10 mg/kg, about 60±5 mg/kg, about 60±4 mg/kg, about 60±3 mg/kg, about 60±2 mg/kg, or about 60±1 mg/kg;
- about 180±20 mg/kg, about 180±10 mg/kg, about 180±5 mg/kg, about 180±4 mg/kg, about 180±3 mg/kg, about 180±2 mg/kg, or about 180±1 mg/kg;
- about 600±50 mg/kg, about 600±40 mg/kg, about 600±30 mg/kg, about 600±20 mg/kg, about 600±10 mg/kg, about 600±5 mg/kg, about 600±4 mg/kg, about 600±3 mg/kg, about 600±2 mg/kg, or about 600±1 mg/kg; or
- about 1800±50 mg/kg, about 1800±40 mg/kg, about 1800±30 mg/kg, about 1800±20 mg/kg, about 1800±10 mg/kg, about 1800±5 mg/kg, about 1800±4 mg/kg, about 1800±3 mg/kg, about 1800±2 mg/kg, or about 1800±1 mg/kg.

Exemplary Embodiment No. 24. The method, compound, or use of any one of the preceding Embodiments, wherein Compound No. 1 or the pharmaceutically acceptable salt thereof is administered at a daily dosage of:

- about 1±3 mg/kg, about 1±2 mg/kg, about 1±1 mg/kg, or about 1±0.1 mg/kg (e.g., about 1 mg/kg);
- about 5±3 mg/kg, about 5±2 mg/kg, or about 5±1 mg/kg;
- about 15±5 mg/kg, about 15±4 mg/kg, about 15±3 mg/kg, about 15±2 mg/kg, or about mg/kg;
- about 30±10 mg/kg, about 30±5 mg/kg, about 30±4 mg/kg, about 30±3 mg/kg, or about mg/kg, or about 30±1 mg/kg (e.g., about 30 mg/kg);
- about 50±10 mg/kg, about 50±5 mg/kg, about 50±4 mg/kg, about 50±3 mg/kg, about 50±2 mg/kg, or about 50±1 mg/kg; or
- about 150±20 mg/kg, about 150±10 mg/kg, about 150±5 mg/kg, about 150±4 mg/kg, about 150±3 mg/kg, about 150±2 mg/kg, or about 150±1 mg/kg.

Exemplary Embodiment No. 25. The method, compound, or use of any one of the preceding Embodiments, wherein Compound No. 2 or the pharmaceutically acceptable salt thereof is administered at a daily dosage of:

- about 25±10 mg, about 25±5 mg, about 25±4 mg, about 25±3 mg, about 25±2 mg, or about mg (e.g., about 25 mg);
- about 50±10 mg, about 50±5 mg, about 50±4 mg, about 50±3 mg, about 50±2 mg, or about mg (e.g., about 50 mg);
- about 100±20 mg, about 100±10 mg, about 100±5 mg, about 100±4 mg, about 100±3 mg, about 100±2 mg, or about 100±1 mg (e.g., about 100 mg);
- about 200±20 mg, about 200±10 mg, about 200±5 mg, about 200±4 mg, about 200±3 mg, about 200±2 mg, or about 200±1 mg (e.g., about 200 mg);
- about 300±20 mg, about 300±10 mg, about 300±5 mg, about 300±4 mg, about 300±3 mg, about 300±2 mg, or about 300±1 mg (e.g., about 300 mg);
- about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg);
- about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg);
- about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg);
- about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg); or
- about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

Exemplary Embodiment No. 26. The method, compound, or use of any one of the preceding Embodiments, wherein Compound No. 2 or the pharmaceutically acceptable salt thereof is administered at a daily dosage of:

- about 60±10 mg/kg, about 60±5 mg/kg, about 60±4 mg/kg, about 60±3 mg/kg, about 60±2 mg/kg, or about 60±1 mg/kg;
- about 180±20 mg/kg, about 180±10 mg/kg, about 180±5 mg/kg, about 180±4 mg/kg, about 180±3 mg/kg, about 180±2 mg/kg, or about 180±1 mg/kg;
- about 600±50 mg/kg, about 600±40 mg/kg, about 600±30 mg/kg, about 600±20 mg/kg, about 600±10 mg/kg, about 600±5 mg/kg, about 600±4 mg/kg, about 600±3 mg/kg, about 600±2 mg/kg, or about 600±1 mg/kg; or
- about 1800±50 mg/kg, about 1800±40 mg/kg, about 1800±30 mg/kg, about 1800±20 mg/kg, about 1800±10 mg/kg, about 1800±5 mg/kg, about 1800±4 mg/kg, about 1800±3 mg/kg, about 1800±2 mg/kg, or about 1800±1 mg/kg.

Exemplary Embodiment No. 27. The method, compound, or use of any one of the preceding Embodiments, wherein Compound No. 2 or the pharmaceutically acceptable salt thereof is administered at a daily dosage of:

- about 1±3 mg/kg, about 1±2 mg/kg, about 1±1 mg/kg, or about 1±0.1 mg/kg (e.g., about 1 mg/kg);
- about 5±3 mg/kg, about 5±2 mg/kg, or about 5±1 mg/kg;
- about 15±5 mg/kg, about 15±4 mg/kg, about 15±3 mg/kg, about 15±2 mg/kg, or about mg/kg;
- about 30±10 mg/kg, about 30±5 mg/kg, about 30±4 mg/kg, about 30±3 mg/kg, or about mg/kg, or about 30±1 mg/kg (e.g., about 30 mg/kg);
- about 50±10 mg/kg, about 50±5 mg/kg, about 50±4 mg/kg, about 50±3 mg/kg, about 50±2 mg/kg, or about 50±1 mg/kg; or
- about 150±20 mg/kg, about 150±10 mg/kg, about 150±5 mg/kg, about 150±4 mg/kg, about 150±3 mg/kg, about 150±2 mg/kg, or about 150±1 mg/kg.

Exemplary Embodiment No. 28. The method of any one of the preceding Embodiments, further comprising administering to the subject in need thereof a therapeutically effective amount of temozolomide.

Exemplary Embodiment No. 29. The compound of any one of the preceding Embodiments, wherein the compound is used in combination with a therapeutically effective amount of temozolomide.

Exemplary Embodiment No. 30. The method of any one of the preceding Embodiments, further comprising administering to the subject in need thereof a therapeutically effective amount of a phosphatidylinositol-3-kinase (PI3K) inhibitor.

Exemplary Embodiment No. 31. The compound of any one of the preceding Embodiments, wherein the compound is used in combination with a therapeutically effective amount of a phosphatidylinositol-3-kinase (PI3K) inhibitor.

Exemplary Embodiment No. 32. The method of any one of the preceding Embodiments, further comprising administering to the subject in need thereof a therapeutically effective amount of amivantamab, capmatinib, or a combination thereof.

Exemplary Embodiment No. 33. The compound of any one of the preceding Embodiments, wherein the compound is used in combination with a therapeutically effective amount of amivantamab, capmatinib, or a combination thereof.

Exemplary Embodiment No. 34. The method of any one of the preceding Embodiments, further comprising administering to the subject in need thereof a therapeutically effective amount of osimertinib.

Exemplary Embodiment No. 35. The compound of any one of the preceding Embodiments, wherein the compound is used in combination with a therapeutically effective amount of osimertinib.

Exemplary Embodiment No. 36. The method of any one of the preceding Embodiments, further comprising administering to the subject in need thereof a therapeutically effective amount of alpelisib.

Exemplary Embodiment No. 37. The compound of any one of the preceding Embodiments, wherein the compound is used in combination with a therapeutically effective amount of alpelisib.

Exemplary Embodiment No. 38. The method of any one of the preceding Embodiments, further comprising administering to the subject in need thereof a therapeutically effective amount of paxalisib.

Exemplary Embodiment No. 39. The compound of any one of the preceding Embodiments, wherein the compound is used in combination with a therapeutically effective amount of paxalisib.

Definitions

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof; while the presentation further intends to refer to the specific configuration of the compound.

Further, it will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture." As used herein, the term "chiral centre" refers to a carbon atom bonded to four nonidentical substituents.

As used herein, the term "chiral isomer" means a compound with at least one chiral centre. Compounds with more than one chiral centre may exist either as an individual diastereomer or as a mixture of diastereomers, termed "diastereomeric mixture." When one chiral centre is present, a stereoisomer may be characterised by the absolute configuration (R or S) of that chiral centre. Absolute configuration refers to the arrangement in space of the substituents attached to the chiral centre. The substituents attached to the chiral centre under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

The terms "nucleic acid" and "polynucleotide" are used interchangeably herein to refer to single- or double-stranded RNA, DNA, or mixed polymers. Polynucleotides may include genomic sequences, extra-genomic and plasmid sequences, and smaller engineered gene segments that express, or may be adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A "native sequence" polynucleotide is one that has the same nucleotide sequence as a polynucleotide derived from nature. A "native sequence" polypeptide is one that has the same amino acid sequence as a polypeptide (e.g. EGFR) derived from nature (e.g., from any species). Such native sequence polynucleotides and polypeptides can be isolated from nature or can be produced by recombinant or synthetic means.

A polynucleotide "variant," as the term is used herein, is a polynucleotide that typically differs from a polynucleotide specifically disclosed herein in one or more substitutions, deletions, additions and/or insertions.

A polypeptide "variant," as the term is used herein, is a polypeptide that typically differs from a polypeptide specifically disclosed herein in one or more substitutions, deletions, additions and/or insertions, or inversions. Such variants may be naturally occurring, non-naturally occurring, or may be synthetically generated.

EGFR mutations (or variants) of the disclosure may comprise one or more substitutions, deletions, additions and/or insertions, or inversions of the amino acid sequence that are alter the function of the resultant protein. Mutations may be detected, for example, by comparison or alignment of a nucleic or amino acid sequence with a wild type sequence.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M.O. (1978) A model of evolutionary change in proteins—Matrices for detecting distant relationships. In Dayhoff, M.O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, CA; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, CA; Wilbur, W. J. and Lipman, D. J. (1983) *Proc. Natl. Acad., Sci. USA*

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

A wild type EGFR sequence of the disclosure may comprise or consist of the amino acid sequence of:

1 mrpsgtagaa llallaalcp asraleekkv cqgtsnkltq lgtfedhfls lqrmfnncev 61 vlgnleityv qrnydlsflk tiqevagyvl ialntverip lenlqiirgn myyensyala 121 vlsnydankt glkelpmrnl qeilhgavrf snnpalcnve siqwrdivss dflsnmsmdf 181 qnhlgscqkc dpscpngscw gageencqkl tkiicaqqcs grcrgkspsd cchnqcaagc 241 tgpresdclv crkfrdeatc kdtcpplmly npttyqmdvn pegkysfgat cvkkcprnyv 301 vtdhgscvra cgadsyemee dgvrkckkce gpcrkvengi gigefkdsls inatnikhfk 361 nctsisgdlh ilpvafrgds fthtppldpq eldilktvke itgflliqaw penrtdlhaf 421 enleiirgrt kqhgqfslav vslnitslgl rslkeisdgd viisgnknlc yantinwkkl 481 fgtsgqktki isnrgensck atgqvchalc spegcwgpep rdcvscrnvs rgrecvdkck 541 llegeprefv enseciqchp eclpqamnit ctgrgpdnci qcahyidgph cvktcpagvm 601 genntlvwky adaghvchlc hpnctygctg pglegcptng pkipsiatgm vgalllllvv 661 algiglfmrr rhivrkrtlr rllqerelve pltpsgeapn qallrilket efkkikvlgs 721 gafgtvykgl wipegekvki pvaikelrea tspkankeil deayvmasvd nphvcrllgi 781 cltstvqlit qlmpfgclld yvrehkdnig sqyllnwcvq iakgmnyled rrlvhrdlaa 841 rnvlvktpqh vkitdfglak llgaeekeyh aeggkvpikw malesilhri ythqsdvwsy 901 gvtvwelmtf gskpydgipa seissilekg erlpqppict idvymimvkc wmidadsrpk 961 freliiefsk mardpqrylv iqgdermhlp sptdsnfyra lmdeedmddv vdadeylipq 1021 qgffsspsts rtpllsslsa tsnnstvaci drnglqscpi kedsflqrys sdptgalted 1081 siddtflpvp eyinqsvpkr pagsvqnpvy hnqplnpaps rdphyqdphs tavgnpeyln 1141 tvqptcvnst fdspahwaqk gshqisldnp dyqqdffpke akpngifkgs taenaeylrv 1201 apqssefiga (SEQ ID NO: 1, corresponding to epidermal growth factor receptor [*Homo sapiens*] and Genbank Accession No. CAA25240).

A wild type HER2 Receptor sequence of the disclosure may comprise or consist of the amino acid sequence of:

1 melaalcrwg lllallppga astqvctgtd mklrlpaspe thldmlrhly qgcqvvqgnl 61 eltylptnas lsflqdigev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gacqpcpinc thscvdlddk gcpaegrasp ltsiisavvg 661 illvvvlgvv fgilikrrqq kirkytmrrl lqetelvepl tpsgampnga qmrilketel 721 rkvkvlgsga fgtvykgiwi pdgenvkipv aikvlrents pkankeilde ayvmagvgsp 781 yvsrllgicl tstvqlvtql mpygclldhv renrgrlgsq dllnwcmqia kgmsyledvr 841 lvhrdlaarn vlvkspnhvk itdfglarll dideteyhad ggkvpikwma lesilrrrft -continued 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag gmvhhrhrss strsgggdlt lglepseeea prsplapseg 1081 agsdvfdgdl gmgaakglqs lpthdpsplq rysedptvpl psetdgyvap ltcspqpeyv 1141 nqpdvrpqpp spregplpaa rpagatlerp ktlspgkngv vkdvfafgga venpeyltpq 1201 ggaapqphpp pafspafdnl yywdqdpper gappstfkgt ptaenpeylg ldvpv (SEQ ID NO: 2, corresponding to receptor tyrosine-protein kinase erbB-2 isoform a precursor [*Homo sapiens*] and GenBank Accession No. NP_004439).

A wild type HER2 Receptor sequence of the disclosure may comprise or consist of the amino acid sequence of:

1 mklrlpaspe thldmlrhly qgcqvvqgnl eltylptnas lsflqdiqev qgyvliahnq 61 vrqvplqrlr ivrgtqlfed nyalavldng dplnnttpvt gaspgglrel qlrslteilk 121 ggvliqrnpq lcyqdtilwk difhknnqla ltlidtnrsr achpcspmck gsrcwgesse 181 dcqsltrtvc aggcarckgp lptdccheqc aagctgpkhs dclaclhfnh sgicelhcpa 241 lvtyntdtfe smpnpegryt fgascvtacp ynylstdvgs ctlvcplhnq evtaedgtqr 301 cekcskpcar vcyglgmehl revravtsan iqefagckki fgslaflpes fdgdpasnta 361 plqpeqlqvf etleeitgyl yisawpdslp dlsvfqnlqv irgrilhnga ysltlqglgi 421 swlglrslre lgsglalihh nthlcfvhtv pwdqlfrnph qallhtanrp edecvgegla 481 chqlcarghc wgpgptqcvn csqflrgqec veecrvlqgl preyvnarhc lpchpecqpq 541 ngsvtcfgpe adqcvacahy kdppfcvarc psgvkpdlsy mpiwkfpdee gacqpcpinc 601 thscvdlddk gcpaeqrasp ltsiisavvg illvvvlgw fgilikrrqq kirkytmrrl 661 lqetelvepl tpsgampnga qmrilketel rkvkvlgsga fgtvykgiwi pdgenvkipv 721 aikvlrents pkankeilde ayvmagvgsp yvsrllgicl tstvqlvtql mpygclldhv 781 renrgrlgsq dllnwcmqia kgmsyledvr lvhrdlaarn vlvkspnhvk itdfglarll 841 dideteyhad ggkvpikwma lesilrrrft hqsdvwsygv tvwelmtfga kpydgipare 901 ipdllekger lpqppictid vymimvkcwm idsecrprfr elvsefsrma rdpqrfvviq 961 nedlgpaspl dstfyrslle dddmgdlvda eeylvpqqgf fcpdpapgag gmvhhrhrss 1021 strsgggdlt lglepseeea prsplapseg agsdvfdgdl gmgaakglqs lpthdpsplq 1081 rysedptvpl psetdgyvap ltcspqpeyv ngpdvrpqpp spregplpaa rpagatlerp 1141 ktlspgkngv vkdvfafgga venpeyltpq ggaapqphpp pafspafdnl yywdqdpper 1201 gappstfkgt ptaenpeylg ldvpv (SEQ ID NO: 3, corresponding to receptor tyrosine-protein kinase erbB-2 isoform b [*Homo sapiens*] and GenBank Accession No. NP_001005862).

A wild type HER2 Receptor sequence of the disclosure may comprise or consist of the amino acid sequence of:

1 mprgswkpqv ctgtdmklrl paspethldm lrhlyqgcqv vqgnleltyl ptnaslsflq 61 digevqgyvl iahnqvrqvp lqrlrivrgt qlfednyala vldngdplnn ttpvtgaspg 121 glrelqlrsl teilkggvli qrnpqlcyqd tilwkdifhk nnqlaltlid tnrsrachpc 181 spmckgsrcw gessedcqsl trtvcaggca rckgplptdc cheqcaagct gpkhsdclac 241 lhfnhsgice lhcpalvtyn tdtfesmpnp egrytfgasc vtacpynyls tdvgsctlvc 301 plhnqevtae dgtqrcekcs kpcarvcygl gmehlrevra vtsanigefa gckkifgsla -continued 361 flpesfdgdp asntaplqpe qlqvfetlee itgylyisaw pdslpdlsvf qnlqvirgri 421 lhngaysltl qglgiswlgl rslrelgsgl alihhnthlc fvhtvpwdql frnphqallh 481 tanrpedecv geglachqlc arghcwgpgp tqcvncsqfl rgqecveecr vlqglpreyv 541 narhclpchp ecqpqngsvt cfgpeadqcv acahykdppf cvarcpsgvk pdlsympiwk 601 fpdeegacqp cpincthscv dlddkgcpae graspltsii savvgillvv vlgvvfgili 661 krrqqkirky tmrrllqete lvepltpsga mpnqaqmril ketelrkvkv lgsgafgtvy 721 kgiwipdgen vkipvaikvl rentspkank eildeayvma gvgspyvsrl lgicltstvq 781 lvtqlmpygc lldhvrenrg rlgsqdllnw cmqiakgmsy ledvrlvhrd laarnvlvks 841 pnhvkitdfg larlldidet eyhadggkvp ikwmalesil rrrfthqsdv wsygvtvwel 901 mtfgakpydg ipareipdll ekgerlpqpp ictidvymim vkcwmidsec rprfrelvse 961 fsrmardpqr fvvignedlg paspldstfy rslledddmg dlvdaeeylv pqqgffcpdp 1021 apgaggmvhh rhrssstrsg ggdltlglep seeeaprspl apsegagsdv fdgdlgmgaa 1081 kglqslpthd psplqrysed ptvplpsetd gyvapltcsp qpeyvnqpdv rpqppspreg 1141 plpaarpaga tlerpktlsp gkngvvkdvf afggavenpe yltpqggaap qphpppafsp 1201 afdnlyywdq dppergapps tfkgtptaen peylgldvpv (SEQ ID NO: 4, corresponding to receptor tyrosine-protein kinase erbB-2 isoform c [*Homo sapiens*] and GenBank Accession No. NP_001276865).

A wild type HER2 Receptor sequence of the disclosure may comprise or consist of the amino acid sequence of:

1 melaalcrwg lllallppga astqvctgtd mklrlpaspe thldmlrhly qgcqvvqgnl 61 eltylptnas lsflqdiqev qgyvliahnq vrqvplqrlr ivrgtqlfed nyalavldng 121 dplnnttpvt gaspgglrel qlrslteilk ggvliqrnpq lcyqdtilwk difhknnqla 181 ltlidtnrsr achpcspmck gsrcwgesse dcqsltrtvc aggcarckgp lptdccheqc 241 aagctgpkhs dclaclhfnh sgicelhcpa lvtyntdtfe smpnpegryt fgascvtacp 301 ynylstdvgs ctlvcplhnq evtaedgtqr cekcskpcar vcyglgmehl revravtsan 361 iqefagckki fgslaflpes fdgdpasnta plqpeqlqvf etleeitgyl yisawpdslp 421 dlsvfqnlqv irgrilhnga ysltlqglgi swlglrslre lgsglalihh nthlcfvhtv 481 pwdqlfrnph qallhtanrp edecvgegla chqlcarghc wgpgptqcvn csqflrgqec 541 veecrvlqgl preyvnarhc lpchpecqpq ngsvtcfgpe adqcvacahy kdppfcvarc 601 psgvkpdlsy mpiwkfpdee gacqpcpinc thscvdlddk gcpaegrasp ltsiisavvg 661 illvvvlgvv fgilikrrqq kirkytmrrl lqetelvepl tpsgampnga qmrilketel 721 rkvkvlgsga fgtvykgiwi pdgenvkipv aikvlrents pkankeilde ayvmagvgsp 781 yvsrllgicl tstvqlvtql mpygclldhv renrgrlgsq dllnwcmqia kgmsyledvr 841 lvhrdlaarn vlvkspnhvk itdfglarll dideteyhad ggkvpikwma lesilrrrft 901 hqsdvwsygv tvwelmtfga kpydgipare ipdllekger lpqppictid vymimvkcwm 961 idsecrprfr elvsefsrma rdpqrfvviq nedlgpaspl dstfyrslle dddmgdlvda 1021 eeylvpqqgf fcpdpapgag gmvhhrhrss strnm (SEQ ID NO: 5, corresponding to receptor tyrosine-protein kinase erbB-2 isoform d precursor [*Homo sapiens*] and GenBank Accession No. NP_001276866).

A wild type HER2 Receptor sequence of the disclosure may comprise or consist of the amino acid sequence of:

```
  1 mklrlpaspe thldmlrhly qgcqvvqgnl eltylptnas lsflqdiqev qgyvliahnq
 61 vrqvplqrlr ivrgtqlfed nyalavldng dplnnttpvt gaspgglrel qlrslteilk
121 ggvliqrnpq lcyqdtilwk difhknnqla ltlidtnrsr achpcspmck gsrcwgesse
181 dcqsltrtvc aggcarckgp lptdccheqc aagctgpkhs dclaclhfnh sgicelhcpa
241 lvtyntdtfe smpnpegryt fgascvtacp ynylstdvgs ctlvcplhnq evtaedgtqr
301 cekcskpcar vcyglgmehl revravtsan igefagckki fgslaflpes fdgdpasnta
361 plqpeqlqvf etleeitgyl yisawpdslp dlsvfqnlqv irgrilhnga ysltlqglgi
421 swlglrslre lgsglalihh nthlcfvhtv pwdqlfrnph qallhtanrp edecvgegla
481 chqlcarghc wgpgptqcvn csqflrgqec veecrvlqgl preyvnarhc lpchpecqpq
541 ngsvtcfgpe adqcvacahy kdppfcvarc psgvkpdlsy mpiwkfpdee gacqpcpinc
601 ths (SEQ ID NO: 6, corresponding to receptor tyrosine-protein
kinase erbB-2 isoform e [Homo sapiens]and GenBank Accession No.
NP_001276867).
```

Based on the definitions given throughout the application the skilled person knows which combinations are synthetically feasible and realistic, e.g. typically combinations of groups leading to heteroatoms directly linked to each other are not contemplated.

As used herein, the term "about" refers to a range covering any normal fluctuations appreciated by one of ordinary skill in the relevant art. In some embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "pharmaceutically acceptable salt" refers to a derivative of the compound of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc. Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3. It is to be understood that all references to pharmaceutically acceptable salts include solvent addition forms (solvates) or crystal forms (polymorphs) as defined herein, of the same salt.

It is understood that the compounds described herein include the compounds themselves, as well as their pharmaceutically acceptable salts, and their solvates, if applicable. A pharmaceutically acceptable salt, for example, can be formed between a pharmaceutically acceptable anion and a positively charged group (e.g., amino) on a compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

It is understood that the compounds of the present disclosure, for example, the salts of the compounds, can exist in either hydrated or unhydrated (the anhydrous) form or as solvates with other solvent molecules. Nonlimiting examples of hydrates include monohydrates and dihydrates. Nonlimiting examples of solvates include ethanol solvates and acetone solvates.

As used herein, the expressions "one or more of A, B, or C," "one or more A, B, or C," "one or more of A, B, and C," "one or more A, B, and C," "selected from the group consisting of A, B, and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

It is understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* $5^{th}$ edition, John Wiley & Sons: New York, 2001; Greene, T. W., Wuts, P. G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. *Fieser, Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art.

As used herein, the term "subject" includes human and non-human mammal, as well as cell lines, cell culture, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof", refers to a subject having a disease (to be treated) or having an increased risk of developing the disease (to be prevented). A subject in need thereof can be one who has been previously diagnosed or identified as having a disease or disorder disclosed herein. A subject in need thereof can also be one who has (e.g., is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that doesn't respond or hasn't yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

It is understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

As used herein, the term "temporal proximity" refers to that administration of one therapeutic agent (Compound No. 2 (e.g., Compound No. 2A or Compound No. 2B)) occurs within a time period before or after the administration of another therapeutic agent (e.g., temozolomide), such that the therapeutic effect of the one therapeutic agent overlaps with the therapeutic effect of the other therapeutic agent. In some embodiments, the therapeutic effect of the one therapeutic agent completely overlaps with the therapeutic effect of the other therapeutic agent. In some embodiments, "temporal proximity" means that administration of one therapeutic agent occurs within a time period before or after the administration of another therapeutic agent, such that there is a synergistic effect between the one therapeutic agent and the other therapeutic agent. "Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, or within 24 hours. In some embodiments, multiple administration of one therapeutic agent can occur in temporal proximity to a single administration of another therapeutic agent. In some embodiments, temporal proximity may change during a treatment cycle or within a dosing regimen.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically effective amount", refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician.

It is understood that, for the compounds of the present disclosure being capable of further forming salts, all of these forms are also contemplated within the scope of the claimed disclosure.

As used herein, the term "pharmaceutically acceptable salts" refer to derivatives of the compounds of the present disclosure wherein the parent compound is modified by making acid or base salts thereof. In some embodiments, the pharmaceutically acceptable salt of a compound is also a prodrug of the compound. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It is understood that all references to pharmaceutically acceptable salts include solvent addition forms (solvates) or crystal forms (polymorphs) as defined herein, of the same salt.

As used herein, the term "prodrug" refers to any agent which, when administered to a mammal, is converted in whole or in part to a targeted compound. In some embodiments, the prodrug of a compound is also a pharmaceutically acceptable salt of the compound.

It is understood that the compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the disclosure can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1. Selectivity of Compound No. 1A for Allosteric EGFR Variants Expressed in GBM To assess the selectivity for Compound No. 1A for EGFR allosteric mutants, anti-proliferative $IC_{50}$ values were determined for Compound No. 1A in EGFR-WT, EGFR-Viii, EGFR-Vii, EGFR-Vvi, EGFR-A289V, and EGFR-G598V. See, e.g., FIG. 1.

Example 2. Plasma and Brain Concentration for Compound No. 1A

Figure 2:
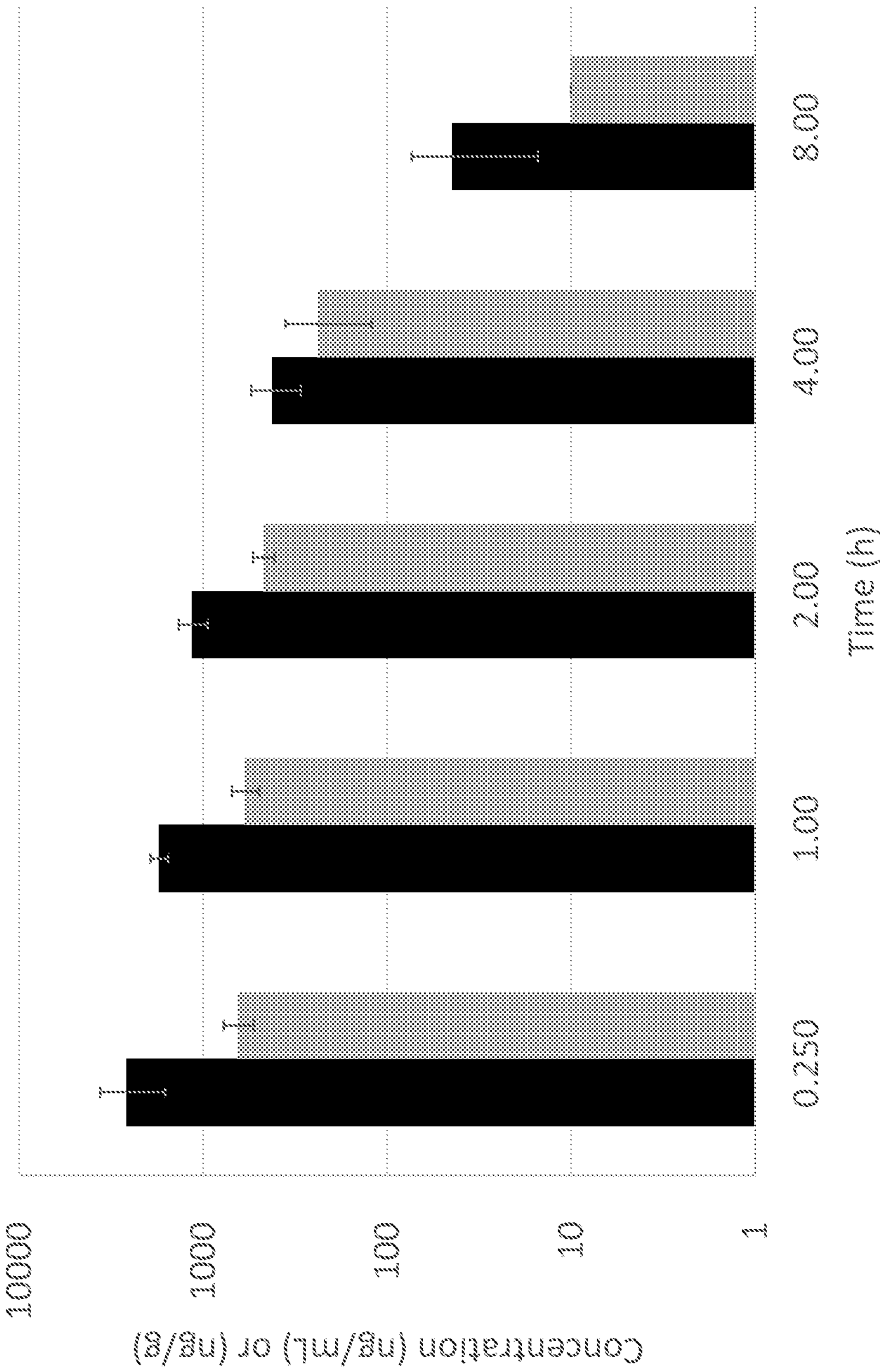
FIG. 2 is a graph showing the mean plasma and brain concentration of Compound No. 1A (15 mg/kg), wherein the black bars represent plasma concentration and the gray bars represent brain concentration.
Figure 10:
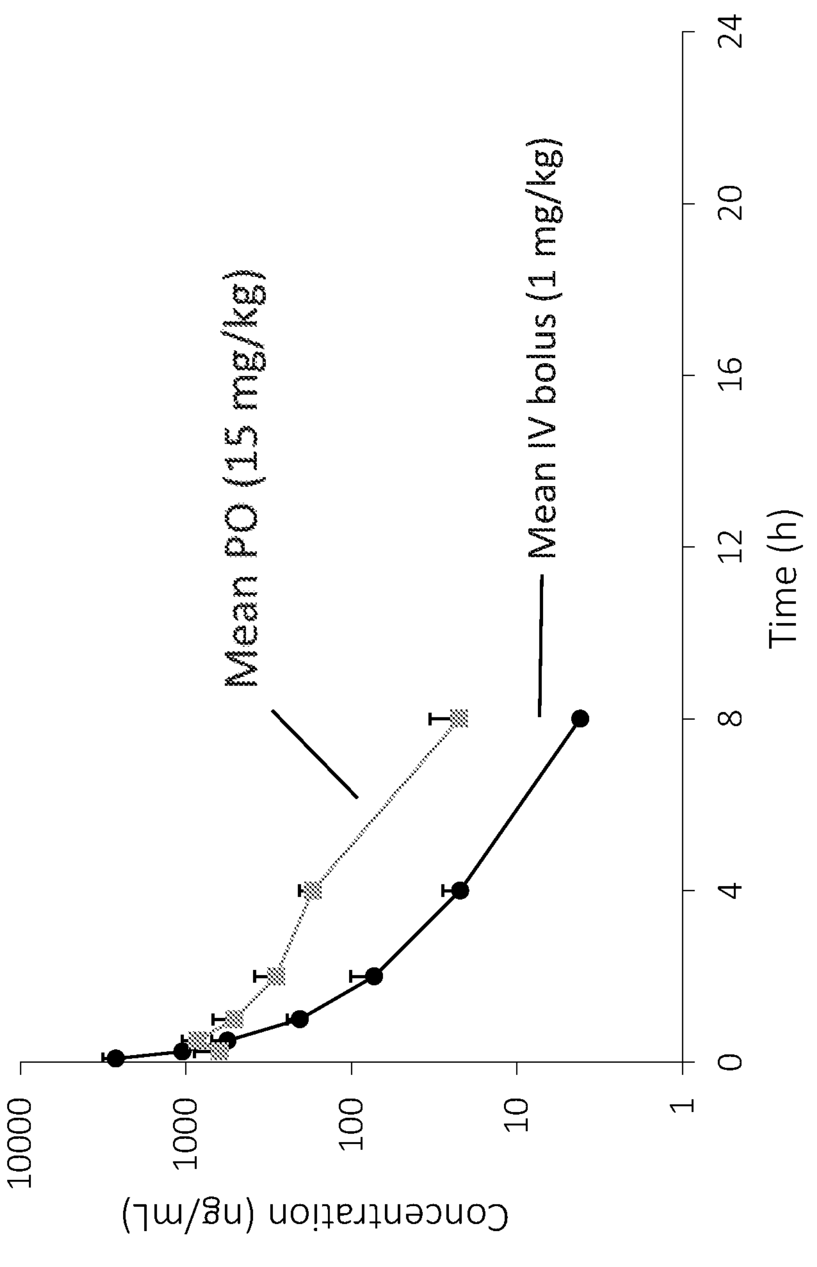
FIG. 10 is a graph showing mean plasma concentration of Compound No. 1A in mice when administered orally (PO) at 15 mg/kg and when administered via IV bolus at 1 mg/kg.

To assess the ability for Compound No. 1A to penetrate the brain, mean plasma and brain concentration was determined for Compound No. 1A when dosed at 15 mg/kg. The unbound partition coefficient ($K_{puu}$) was determined to be 0.19. See, e.g., FIG. 2. FIG. 10 shows the mean plasma concentration of Compound No. 1A in mice when administered orally (PO) at 15 mg/kg and when administered via IV bolus at 1 mg/kg. Pharmacokinetic (PK) parameters were measured for mice after being administered Compound No. 1A orally (P0) at 15 mg/kg and when administered via IV bolus at 1 mg/kg as shown in Table A below.

TABLE A

| | Mouse (BalbC) |
|---|---|
| IV Dose | 1 mg/kg[a] |
| $C_0$ (ng/ml) | 4241 |
| $T_{1/2}$ (h) | 1.15 |
| $Vd_{ss}$ (L/kg) | 0.60 |
| Cl (mL/min/kg) | 14 |
| $AUC_{0\text{-}last}$ (ng · h/mL) | 1184 |
| PO Dose | 15 mg/kg[b] |
| $C_{max}$ (ng/mL) | 855 |
| $T_{max}$ (h) | 0.5 |
| $T_{1/2}$ (h) | 1.7 |
| $AUC_{0\text{-}last}$ (ng · h/mL) | 1716 |
| Bioavailability (%) | 13 |
| AUClast_brain/AUClast_plasma | 0.375 |

[a]0.5 mg/ml in 50% PEG400/50% water, clear solution;
[b]1.5 mg/ml in 0.5% methylcellulose and 0.4% Tween 80, clear solution. The data presented in Table A are approximate and subject to experimental and instrumental variations.

Example 3. Engagement of Allosteric EGFR Mutants In Vivo with Compound No. 1A

Figure 3:
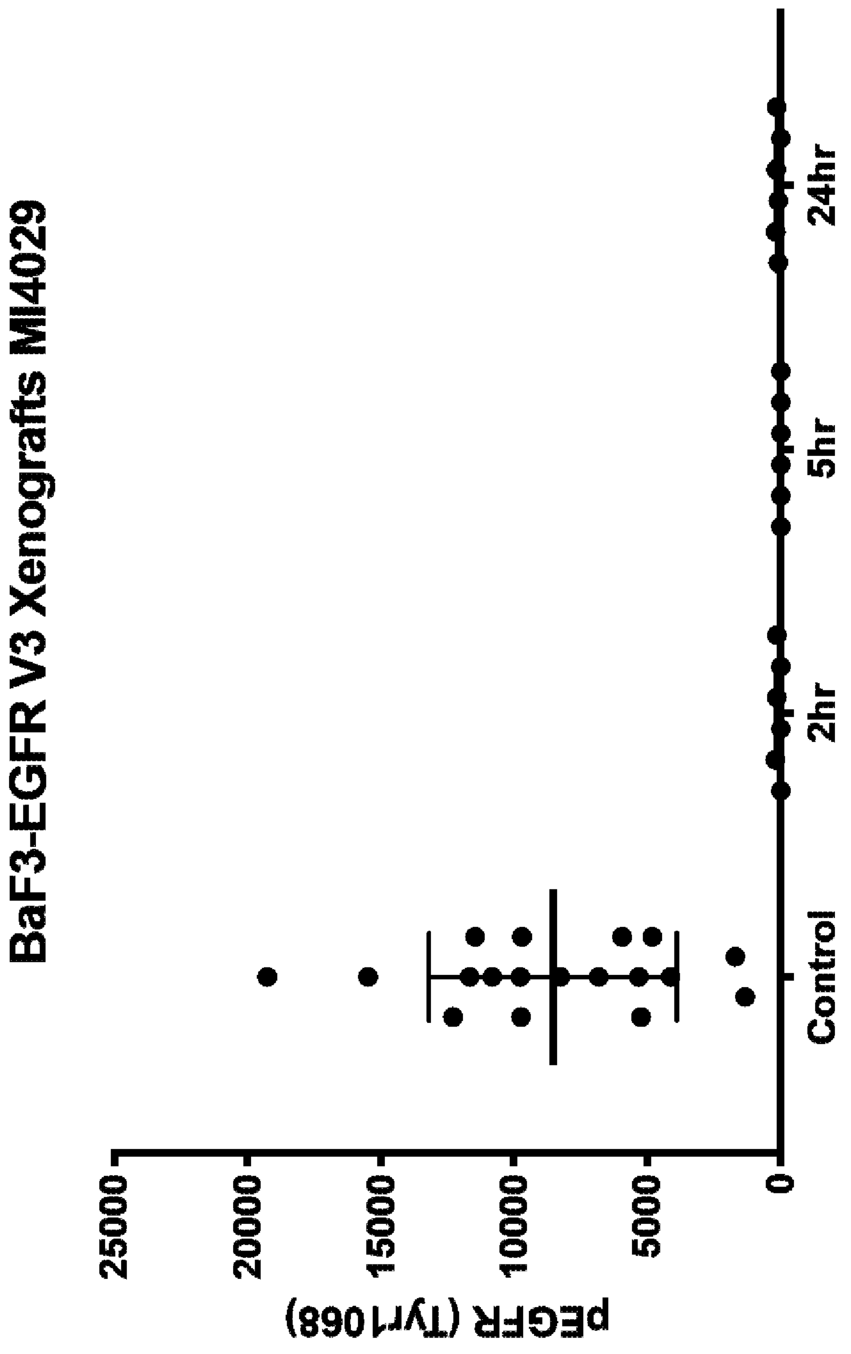
FIG. 3 is a graph showing the relationship between pEGFR (Tyr1068) and the administration of Compound No. 1A at 15 mg/kg.

The relationship between pEGFR and administration of Compound No. 1A was determined in BaF3-EGFR V2 Xenografts MI4029. See, e.g., FIG. 3.

Figure 4:
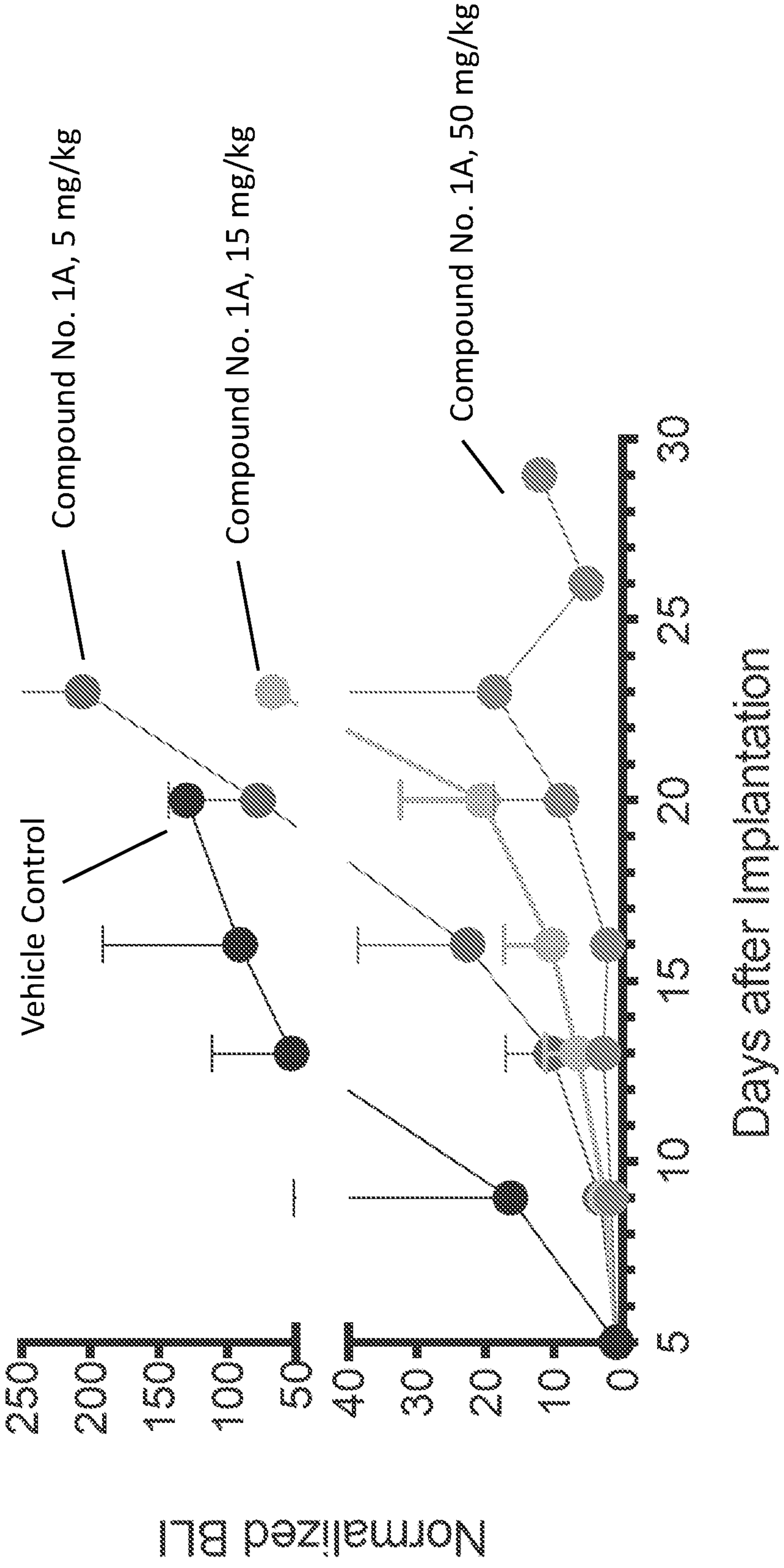
FIG. 4 is a graph showing the normalized bioluminescence intensity (BLI) of GBM6 orthotopic brain patient derived xenograft tumors expressing EGFR-Viii when treated with Compound No. 1A at 50 mg/kg, 15 mg/kg, or 5 mg/kg.

Example 4. Compound No. 1A Inhibits Tumor Growth of Intracranial PDX Tumors Expressing Allosteric EGFR Mutants To assess the ability of Compound No. 1A to inhibit tumor growth, the normalized bioluminescence intensity (BLI) of GBM6 orthotopic brain patient derived xenograft tumors expressing EGFR-Viii was determined when treated with Compound No. 1A at 50 mg/kg, 15 mg/kg, or 5 mg/kg. See, e.g., FIG. 4.

Figure 5:
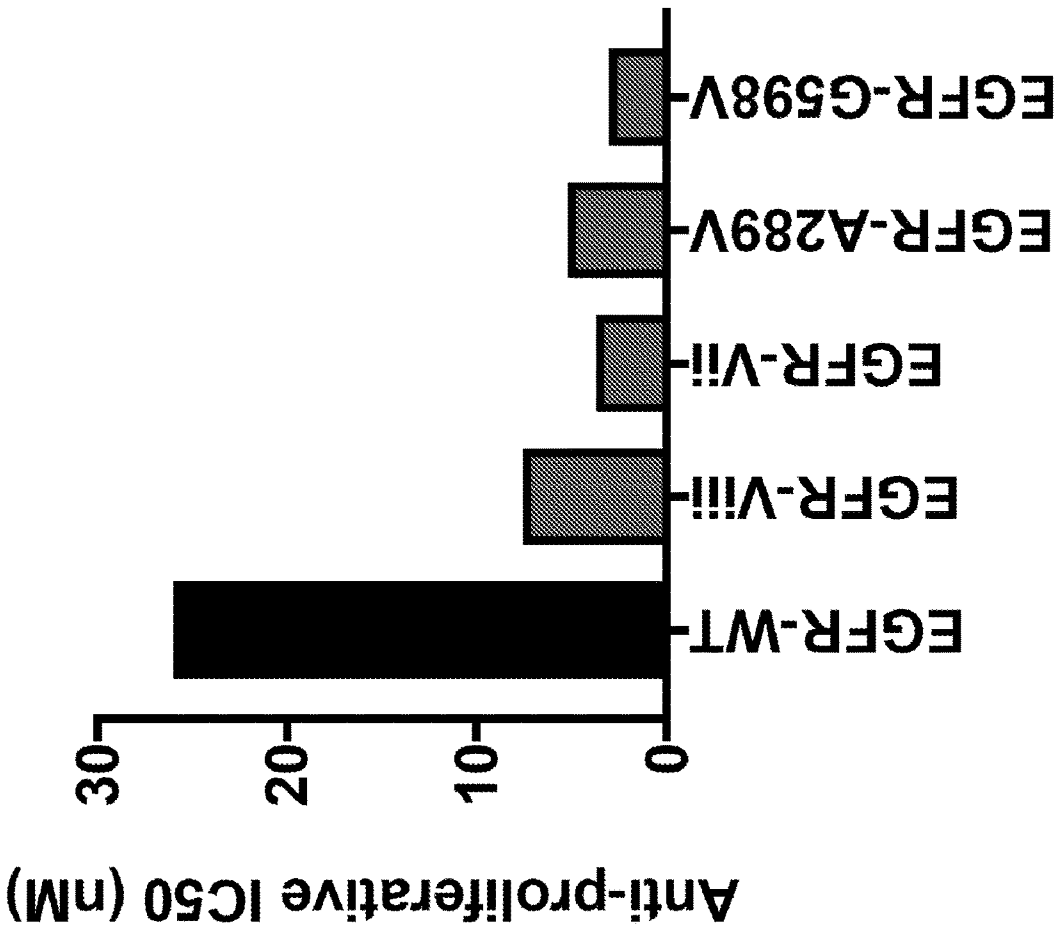
FIG. 5 is a graph showing the anti-proliferative $IC_{50}$ values for Compound No. 2B in EGFR-WT, EGFR-Viii, EGFR-Vii, EGFR-A289V, and EGFR-G598V.

Example 5. Selectivity of Compound No. 2B for Allosteric EGFR Variants Expressed in GBM To assess the selectivity for Compound No. 2B for EGFR allosteric mutants, anti-proliferative $IC_{50}$ values were determined for Compound No. 2B in EGFR-WT, EGFR-Viii, EGFR-Vii, EGFR-A289V, and EGFR-G598V. See, e.g., FIG. 5.

Example 6. Plasma and Brain Concentration for Compound No. 2B

Figure 6:
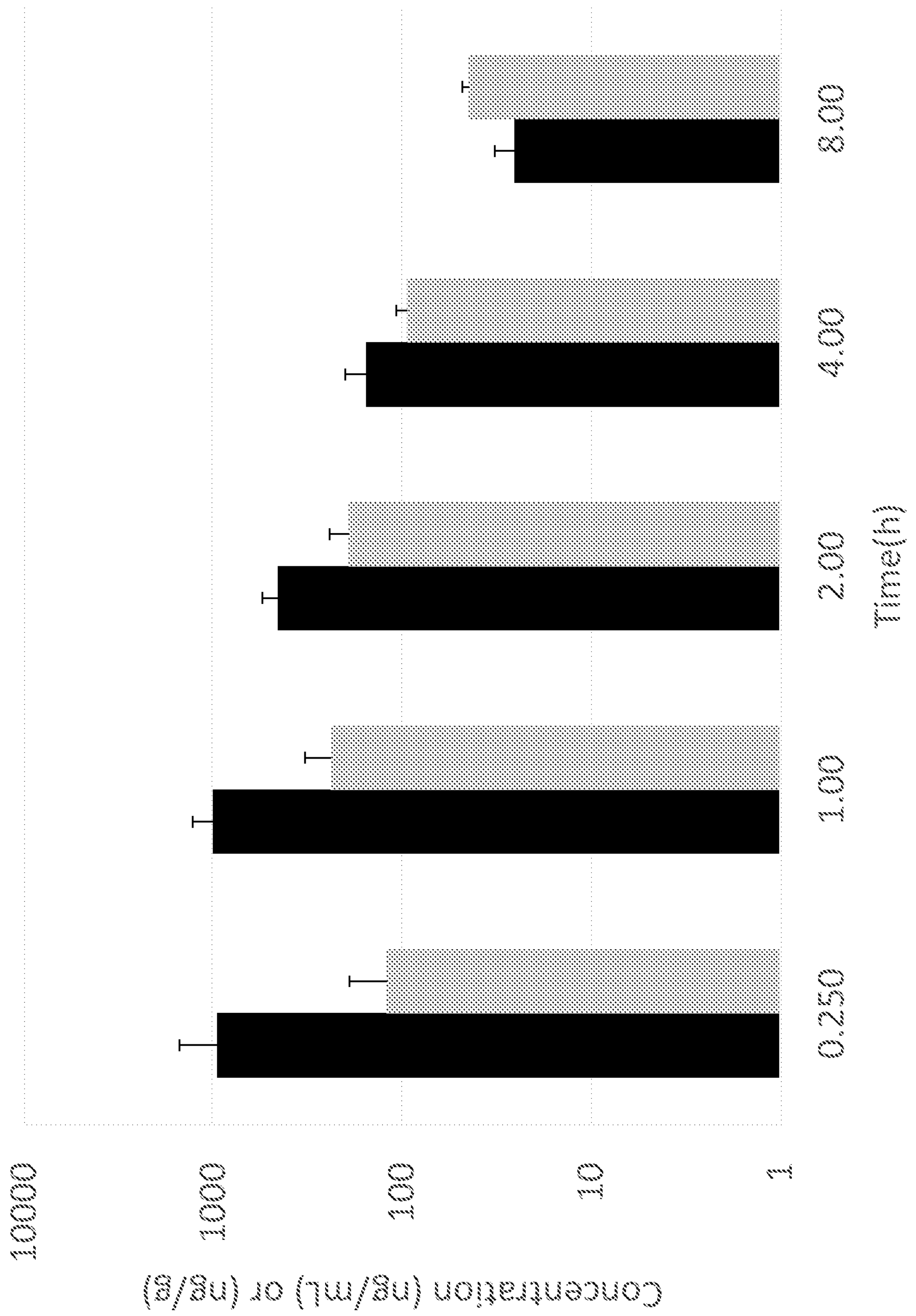
FIG. 6 is a graph showing the mean plasma and brain concentration of Compound No. 2B (15 mg/kg), wherein the black bars represent plasma concentration and the gray bars represent brain concentration.
Figure 11:
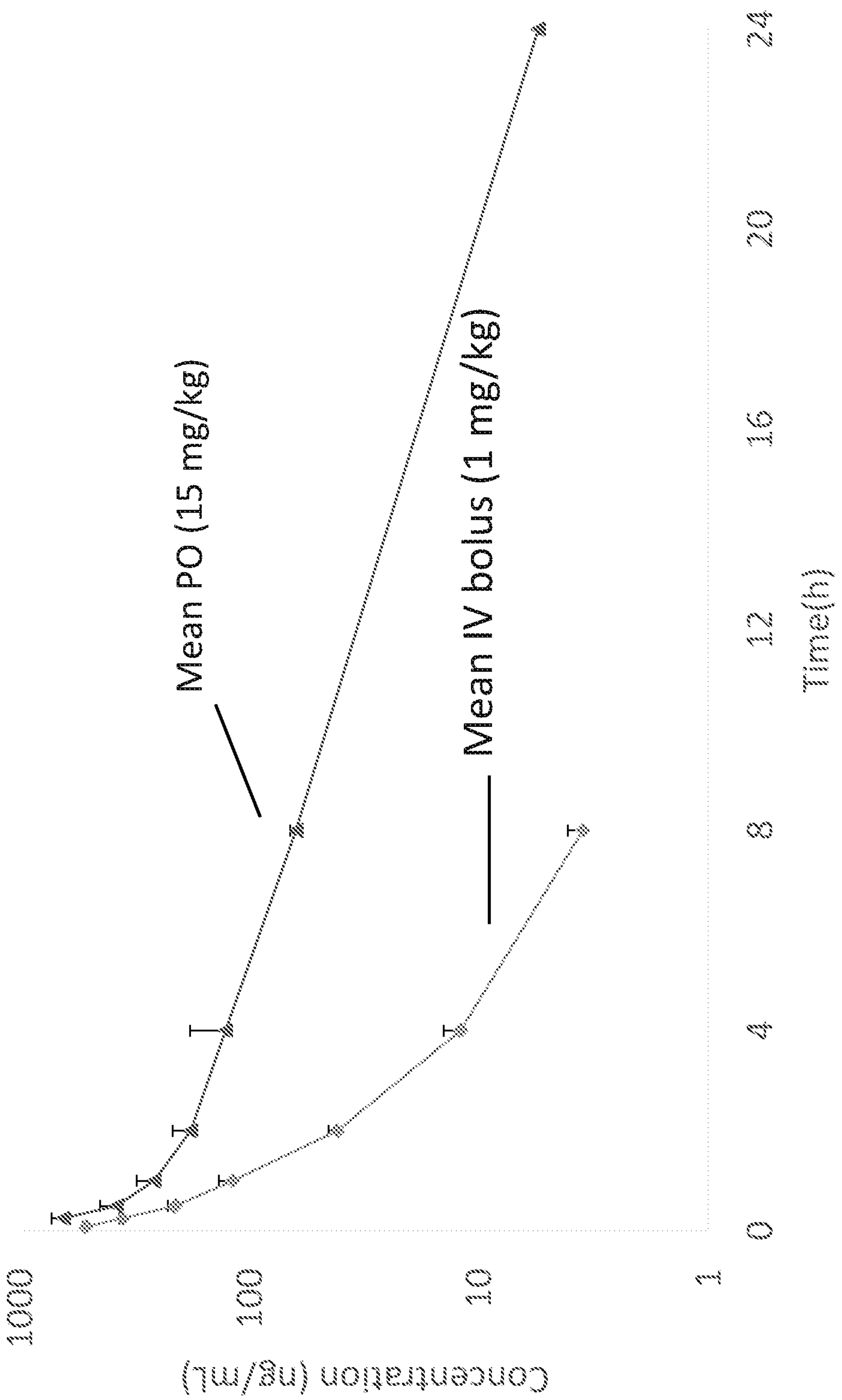
FIG. 11 is a graph showing mean plasma concentration of Compound No. 2B in mice when administered orally (PO) at 15 mg/kg and when administered via IV bolus at 1 mg/kg.

To assess the ability for Compound No. 2B to penetrate the brain, mean plasma and brain concentration was determined for Compound No. 2B when dosed at 15 mg/kg. See, e.g., FIG. 6. FIG. 11 shows the mean plasma concentration of Compound No. 2B in mice when administered orally (PO) at 15 mg/kg and when administered via IV bolus at 1 mg/kg. Pharmacokinetic (PK) parameters were measured for mice after being administered Compound No. 2B orally (PO) at 15 mg/kg and when administered via IV bolus at 1 mg/kg as shown in Table B below.

TABLE B

| | Mouse (BalbC) |
|---|---|
| IV Dose | 1 mg/kg[a] |
| $C_0$ (ng/ml) | 624 |
| $T_{1/2}$ (h) | 1.6 |
| $Vd_{ss}$ (L/kg) | 3.15 |
| Cl (mL/min/kg) | 39 |
| $AUC_{0\text{-}last}$ (ng · h/mL) | 419 |
| PO Dose | 15 mg/kg[b] |
| $C_{max}$ (ng/mL) | 653 |
| $T_{max}$ (h) | 0.25 |
| $T_{1/2}$ (h) | 3.7 |
| $AUC_{0\text{-}last}$ (ng · h/mL) | 1510 |
| Bioavailability (%) | 25 |
| AUClast_brain/AUClast_plasma | 0.379 |

[a]0.50 mg/mL in 10% DMA: 40% PEG400: 50% water, clear solution;
[b]1.50 mg/mL in 10% DMA: 40% PEG400: 50% water, clear solution. The data presented in Table B are approximate and subject to experimental and instrumental variations.

Example 7. Engagement of Allosteric EGFR Mutants In Vivo with Compound No. 2B

Figure 7:
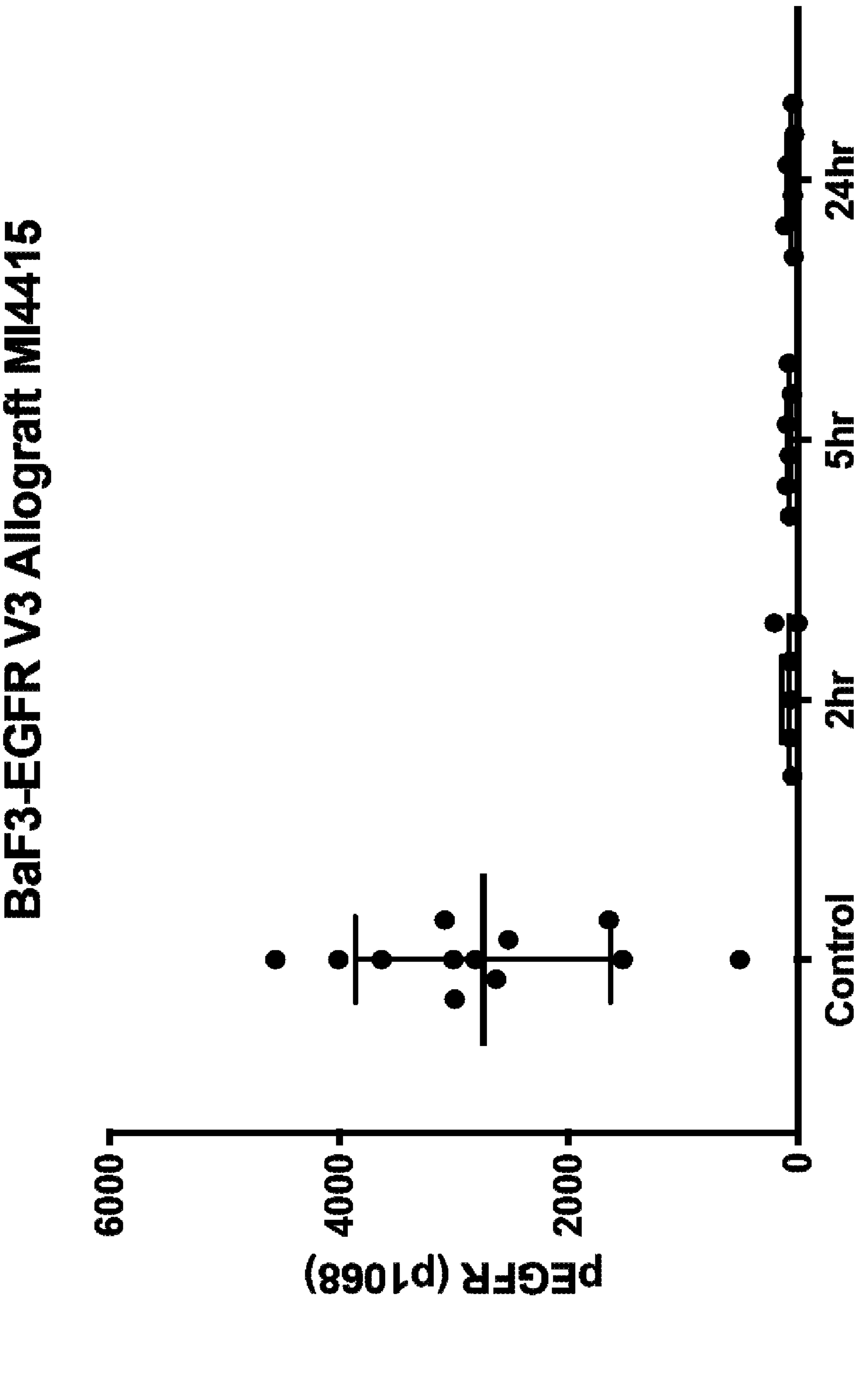
FIG. 7 is a graph showing the relationship between pEGFR (P1068) and the administration of Compound No. 2B at 50 mg/kg.

The relationship between pEGFR and administration of Compound No. 2B was determined in BaF3-EGFR V3 Xenografts MI4415. See, e.g., FIG. 7.

Figure 8:
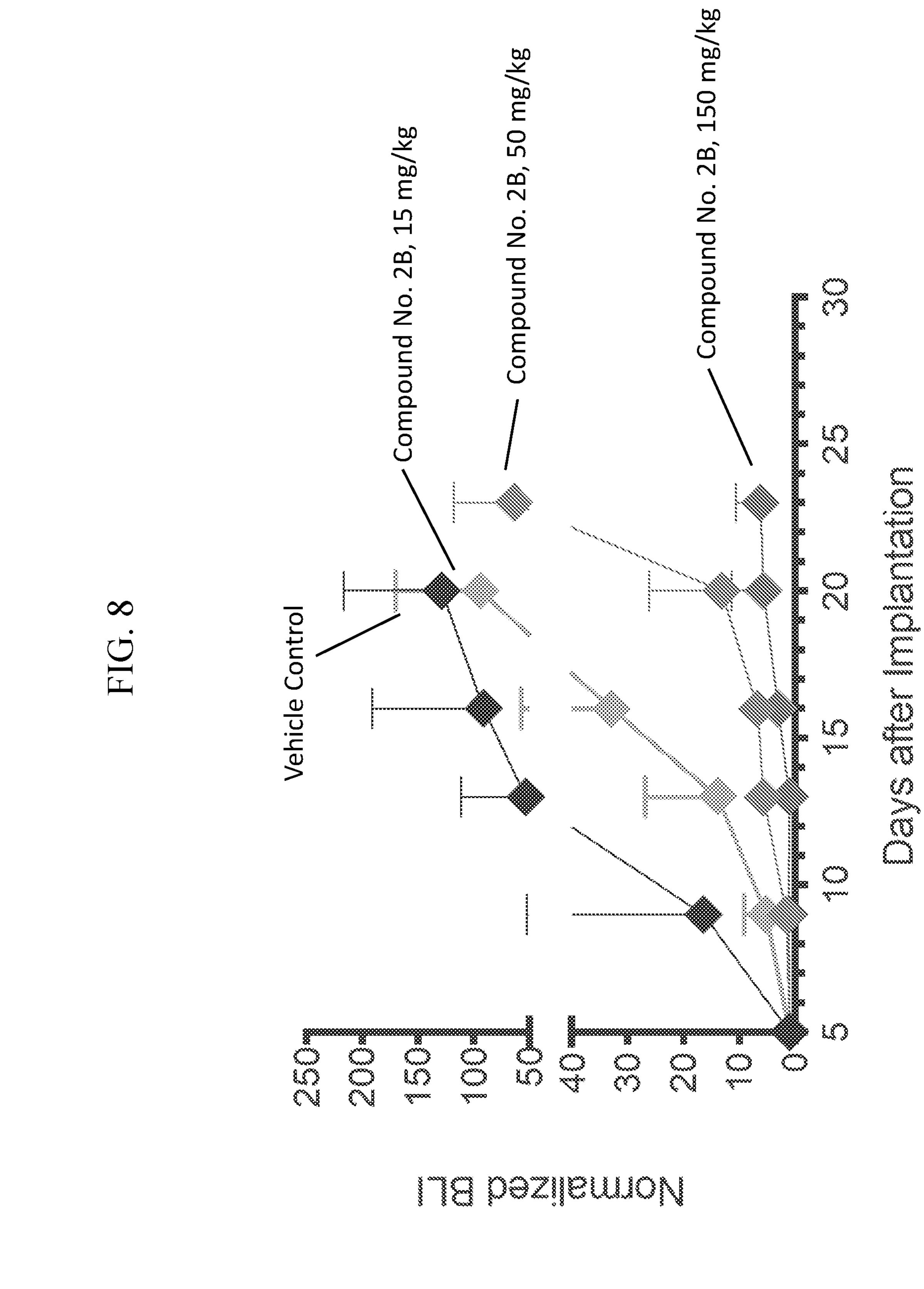
FIG. 8 is a graph showing the normalized bioluminescence intensity (BLI) of GBM6 orthotopic brain patient derived xenograft tumors expressing EGFR-Viii when treated with Compound No. 2B at 150 mg/kg, 50 mg/kg, or 15 mg/kg.

Example 8. Compound No. 2B Inhibits Tumor Growth of Intracranial PDX Tumors Expressing Allosteric EGFR Mutants To assess the ability of Compound No. 2B to inhibit tumor growth, the normalized bioluminescence intensity (BLI) of GBM6 orthotopic brain patient derived xenograft tumors expressing EGFR-Viii was determined when treated with Compound No. 2B at 150 mg/kg, 50 mg/kg, or 15 mg/kg. See, e.g., FIG. 8.

Figure 9:
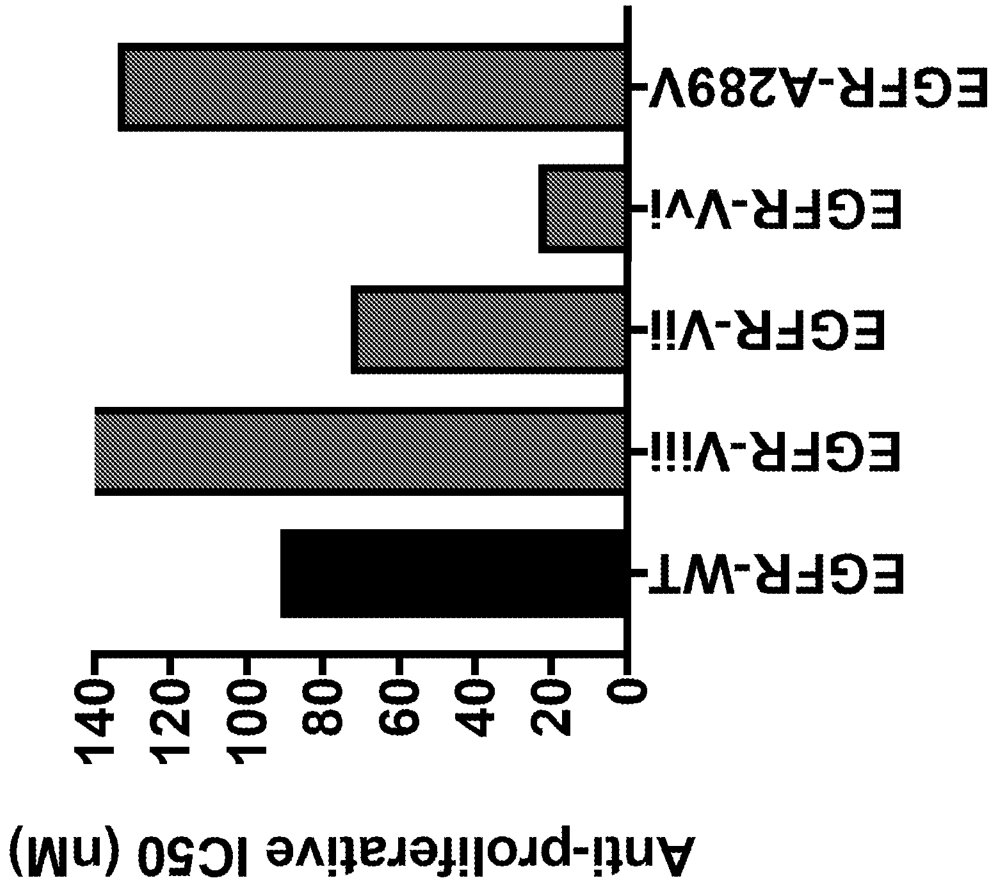
FIG. 9 is a graph showing the anti-proliferative $IC_{50}$ values for osimertinib in EGFR-WT, EGFR-Viii, EGFR-Vii, EGFR-Vvi, and EGFR-A289V.

Example 9. Selectivity of Osimertinib for Allosteric EGFR Variants Expressed in GBM To assess the selectivity for osimertinib for EGFR allosteric mutants, anti-proliferative $IC_{50}$ values were determined for osimertinib in EGFR-WT, EGFR-Viii, EGFR-Vii, EGFR-Vvi, and EGFR-A289V. See, e.g., FIG. 9. Potency and selectivity is not similarly captured by Osimertinib compared to Compound No. 1A and Compound No. 2B.

Figure 12:
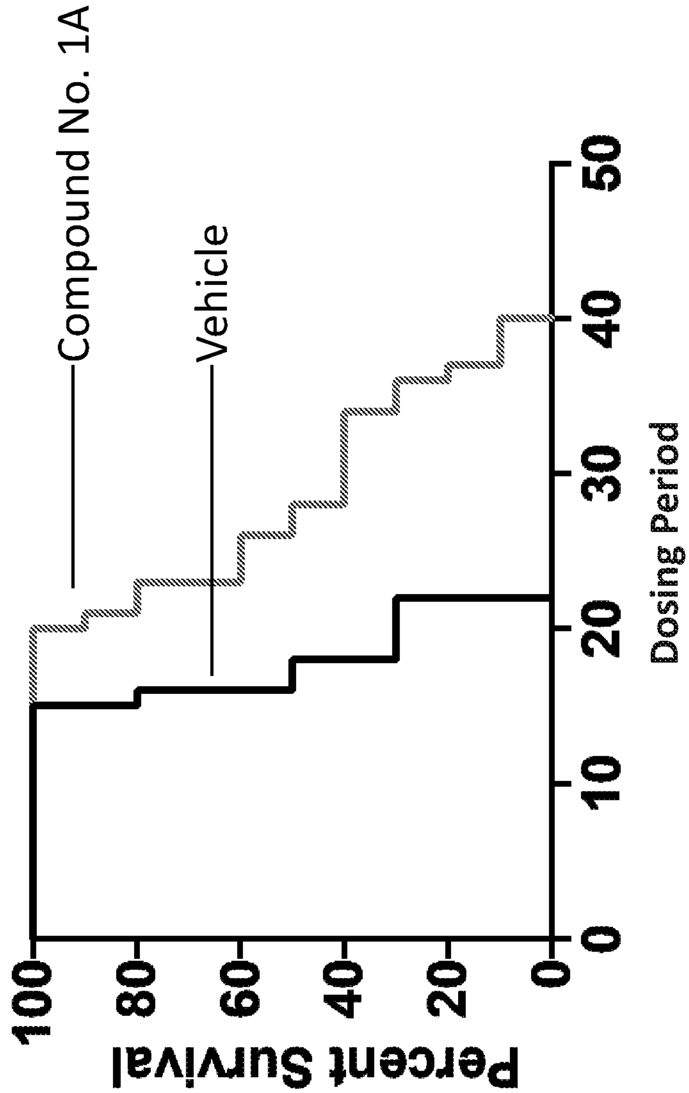
FIG. 12 is a graph showing the percent survival of mice expressing intracranial GBM6 patient derived tumors when treated orally with 50 mg/kg of Compound No. 1A.

Example 10. Compound No. 1A Increases Survival Rate in Mice Expressing Intracranial GBM6 Patient Derived Tumors To assess the efficacy for Compound No. 1A, percent survival of mice expressing intracranial GBM6 patient derived tumors when treated orally with 50 mg/kg of Compound No. 1A was determined. FIG. 12 shows percent survival increased over longer dosing periods.

Figure 13:
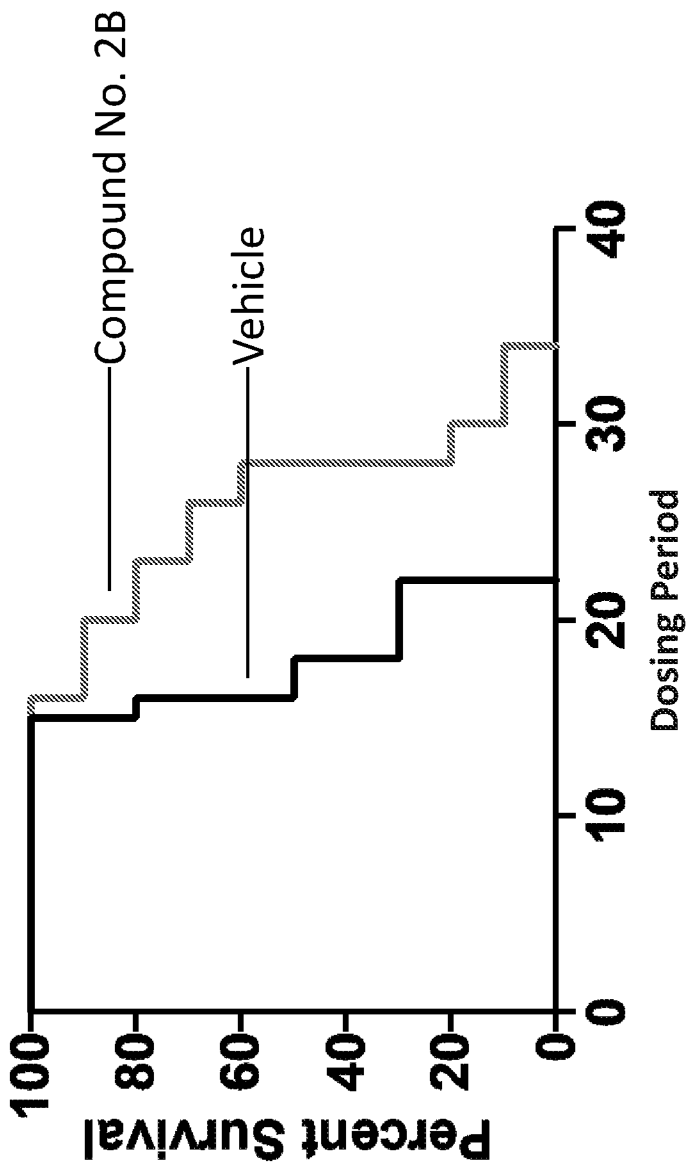
FIG. 13 is a graph showing the percent survival of mice expressing intracranial GBM6 patient derived tumors when treated orally with 50 mg/kg of Compound No. 2B.

Example 11. Compound No. 2B Increases Survival Rate in Mice Expressing Intracranial GBM6 Patient Derived Tumors To assess the efficacy for Compound No. 2B, percent survival of mice expressing intracranial GBM6 patient derived tumors when treated orally with 50 mg/kg of Compound No. 2B was determined. FIG. 13 shows percent survival increased over longer dosing periods.

Figure 14A:
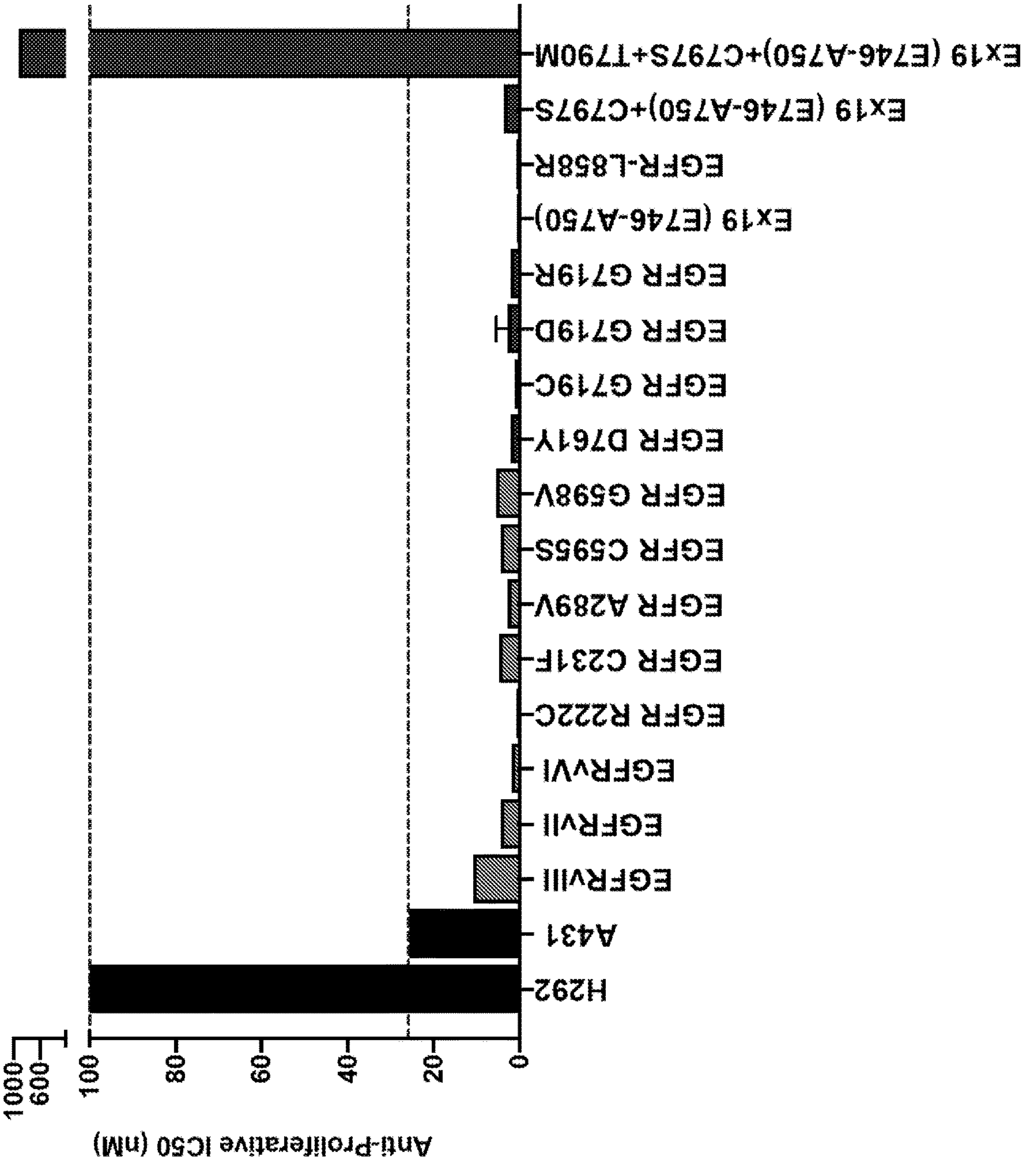
FIGS. 14A-14B are graphs showing in vitro $IC_{50}$ values against a panel of an expanded number of EGFR mutations indicating a spectrum of Compound No. 2B.
Figure 14B:
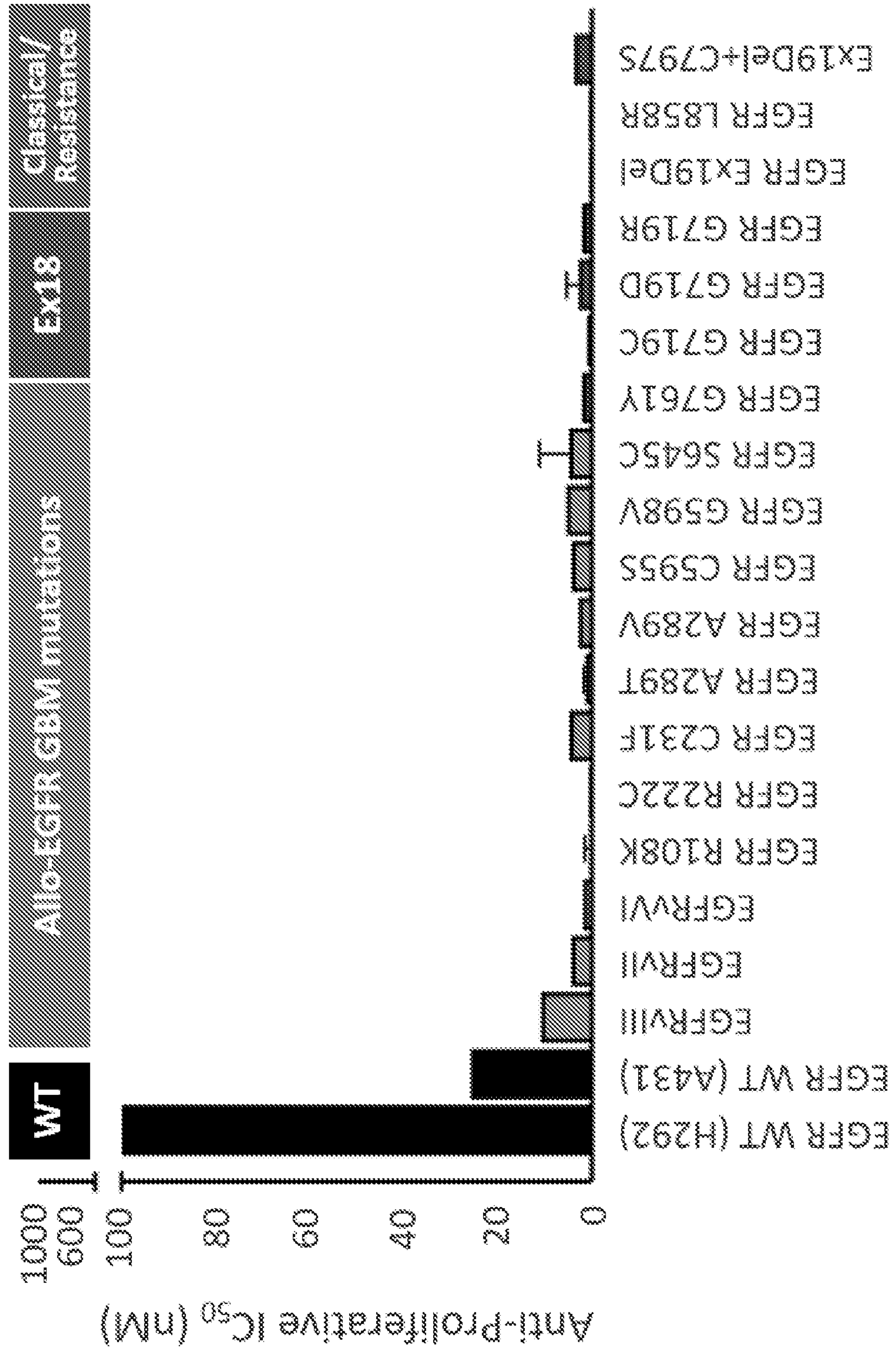
Figure 14C:
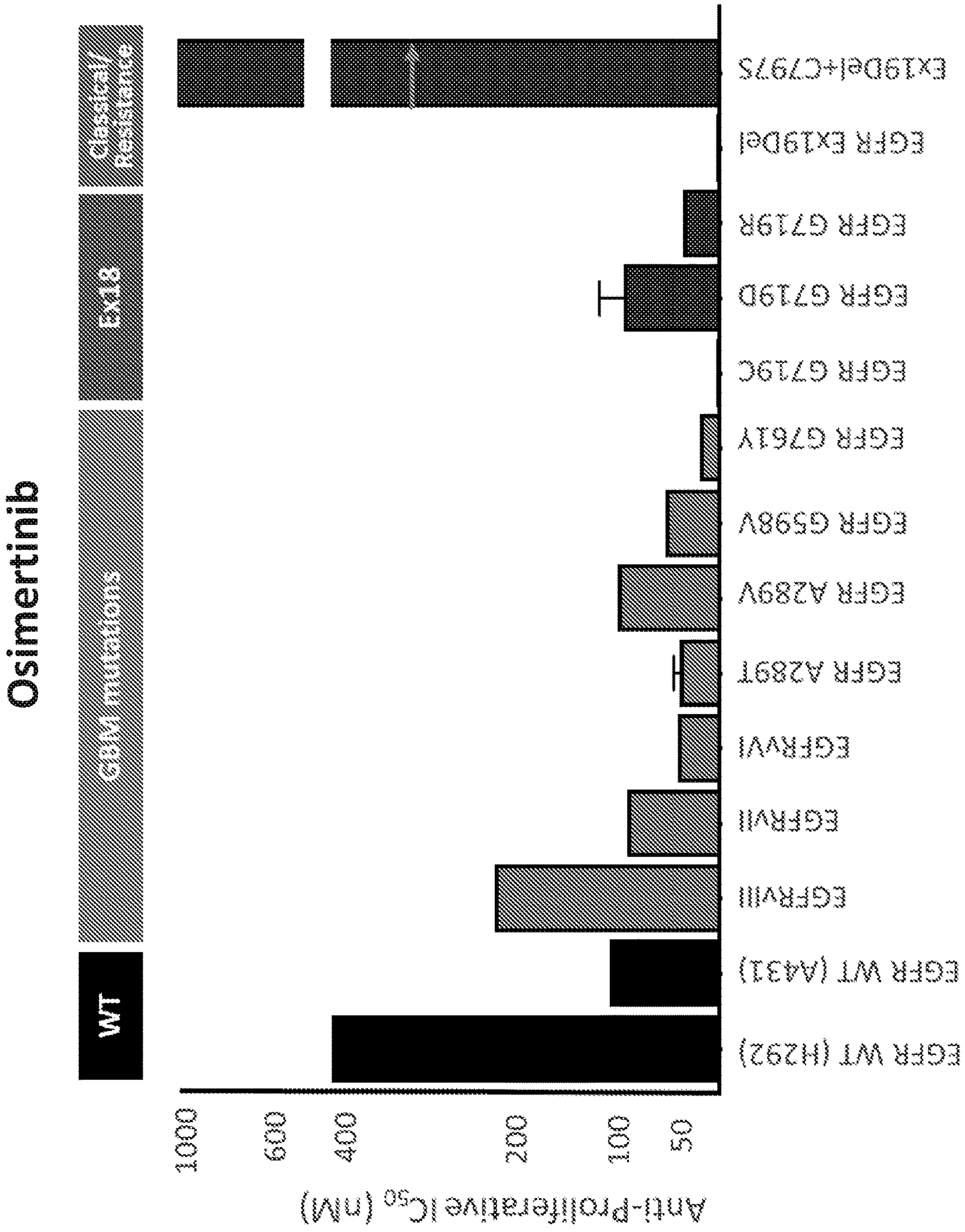
FIG. 14C is a graph showing in vitro $IC_{50}$ values for osimertinib against a panel of an expanded number of EGFR mutations.
Figure 22:
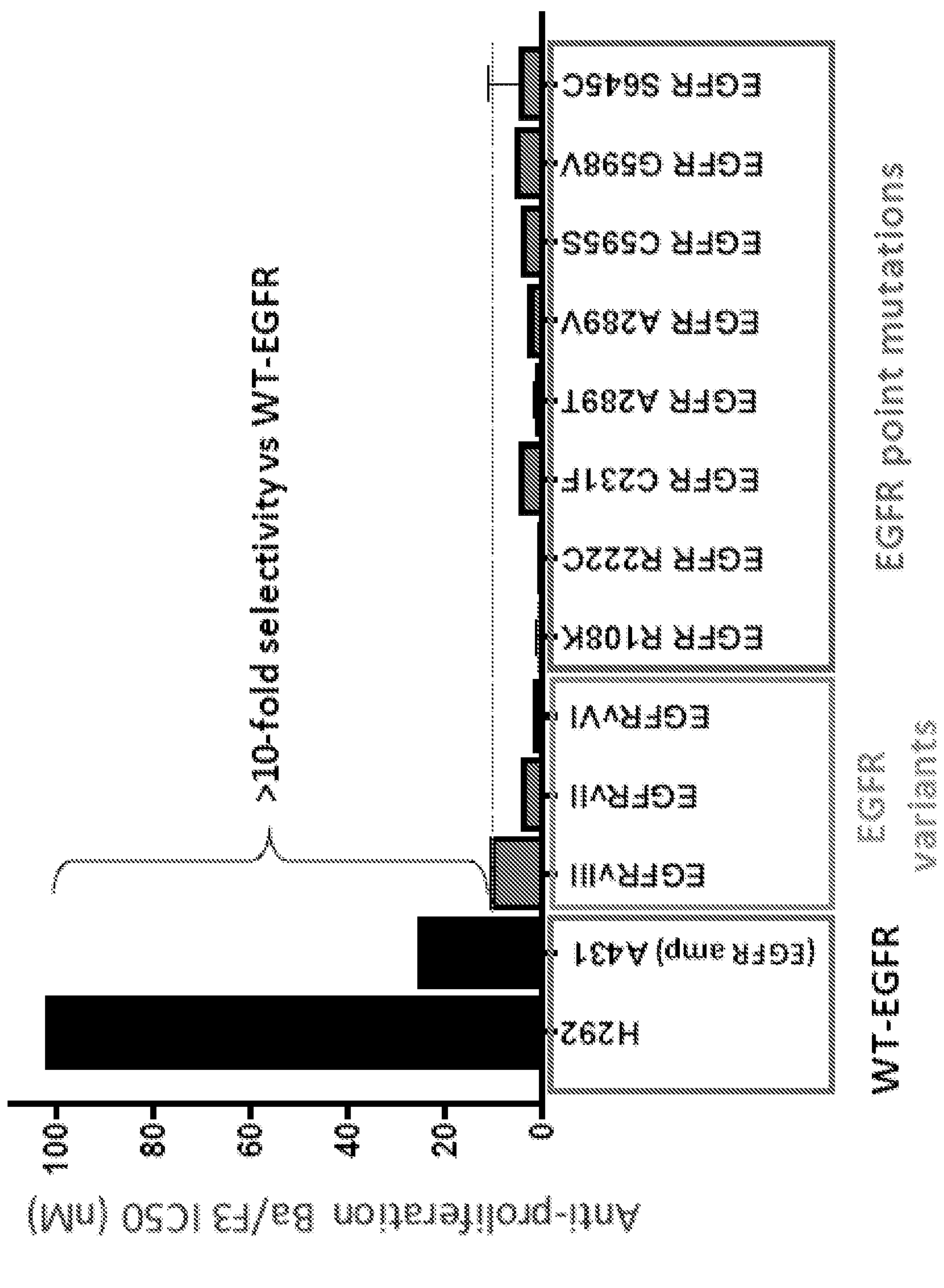
FIG. 22 is a graph showing in vitro $IC_{50}$ values against a panel of an expanded number of EGFR variants and mutants found in GBM.
Figure 23:
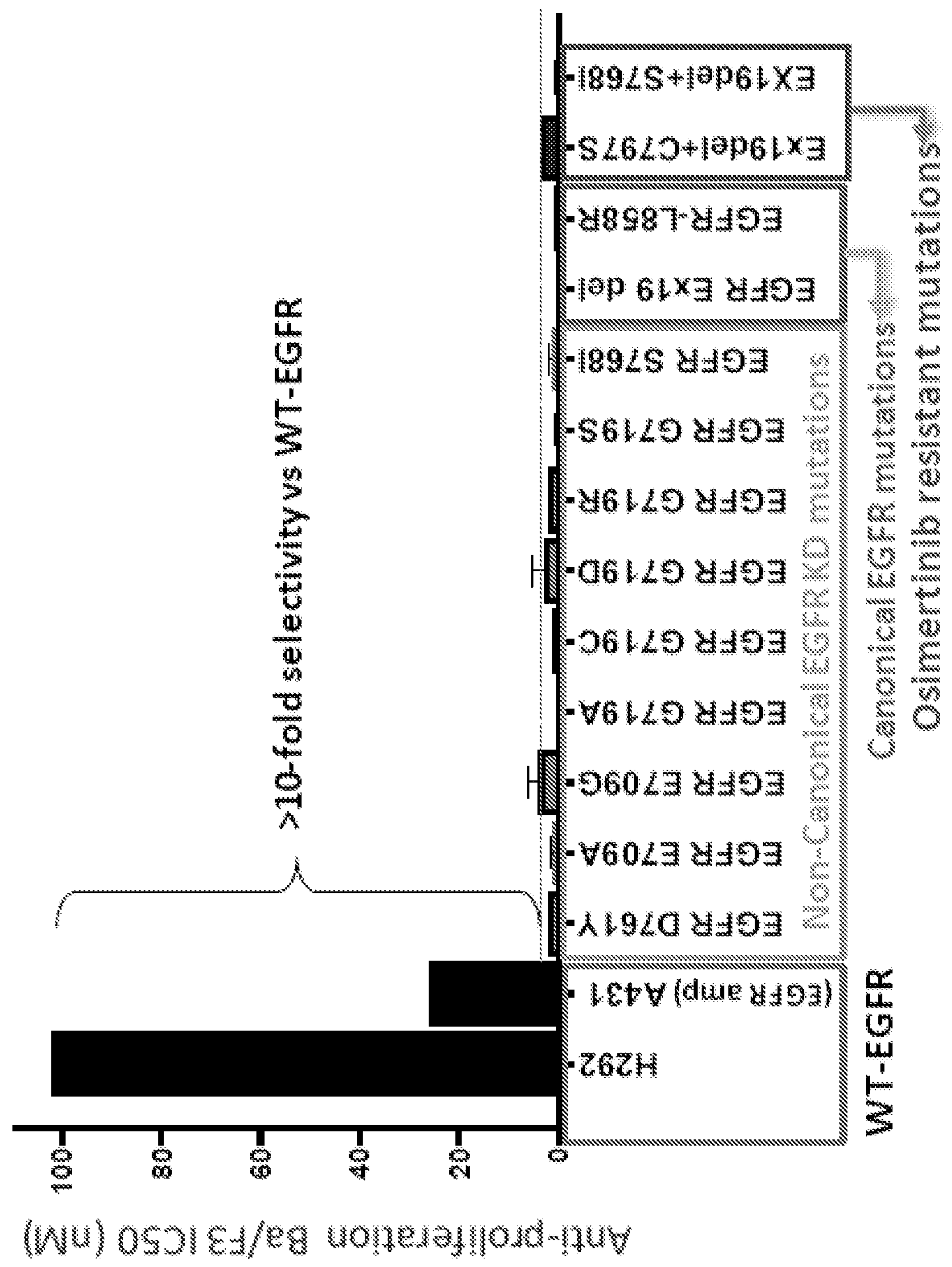
FIG. 23 is a graph showing in vitro $IC_{50}$ values against a panel of an expanded number of EGFR mutants of intrinsic resistance and acquired resistance in non-small cell lung cancer (NSCLC).

Example 12. Compound No. 2B Shown to Achieve Potent and Selective Inhibition of a Spectrum of Allosteric EGFR Variants To assess the potency of Compound No. 2B for inhibition of allosteric EGFR variants expressed in GBM and/or NSCLC, anti-proliferative $IC_{50}$ values were determined for Compound No. 2B inhibiting wild-type EGFR (H292), amplified wild-type EGFR (A431), EGFRvIII, EGFRvII, EGFRvV1, EGFR-R222C, EGFR-C231F, EGFR-A289V, EGFR-0595S, EGFR-G598V, EGFR-D761Y, EGFR-G719C, EGFR-G719D, EGFR-G719R, EGFR-E746-A750del, EGFR-L858R, EGFR-E746-A750del+C797, and EGFR-E746-A750del+C797S+T790M. See, e.g., FIG. 14A. Compound No. 2B was further demonstrated to inhibit EGFR-R108K, EGFR-A298T, EGFR-S645C with an anti-proliferative $IC_{50}$ of less than 10 nM. See, e.g., FIG. 14B. Compound No. 2B was demonstrated to have low activity against wild-type EGFR (H292) and moderate activity against amplified wild-type EGFR (A431). Anti-proliferative $IC_{50}$ values were also determined for osimertinib. See, e.g., FIG. 14C. Compound No. 2B was found to have increased potency and selectivity against EGFR mutations that occur in GBM compared to osimertinib. Additionally, Compound No. 2B demonstrated activity against the C797S resistance mutation. FIG. 22 and FIG. 23 also show greater than 10-fold selectivity in EGFR variants and mutants found in GBM and of intrinsic resistance and acquired resistance in NSCLC.

Figure 15:
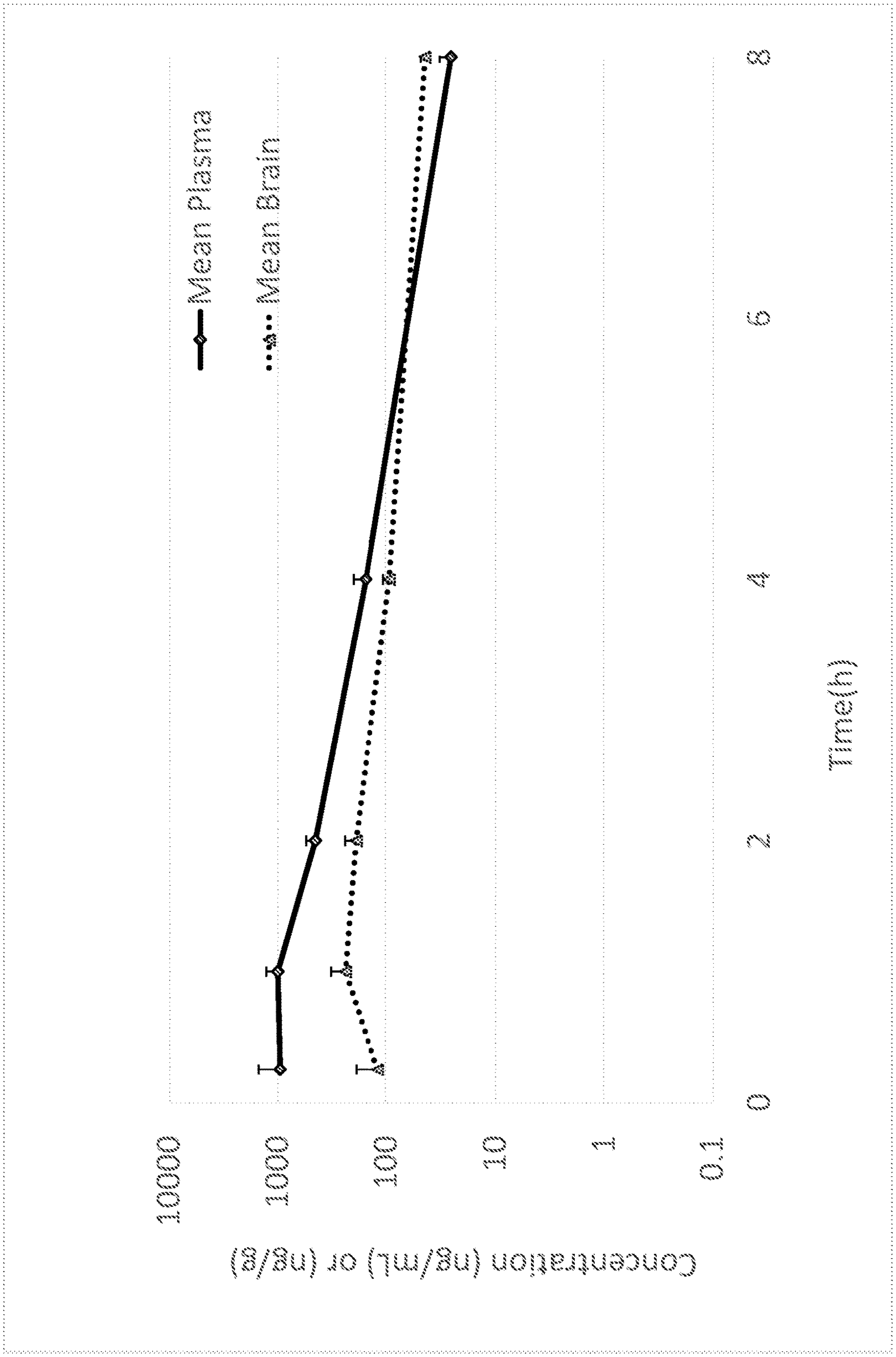
FIG. 15 is a graph showing the mean concentration of Compound No. 2B in plasma and in brain in mouse when administered PO at 15 mg/kg.
Figure 16:
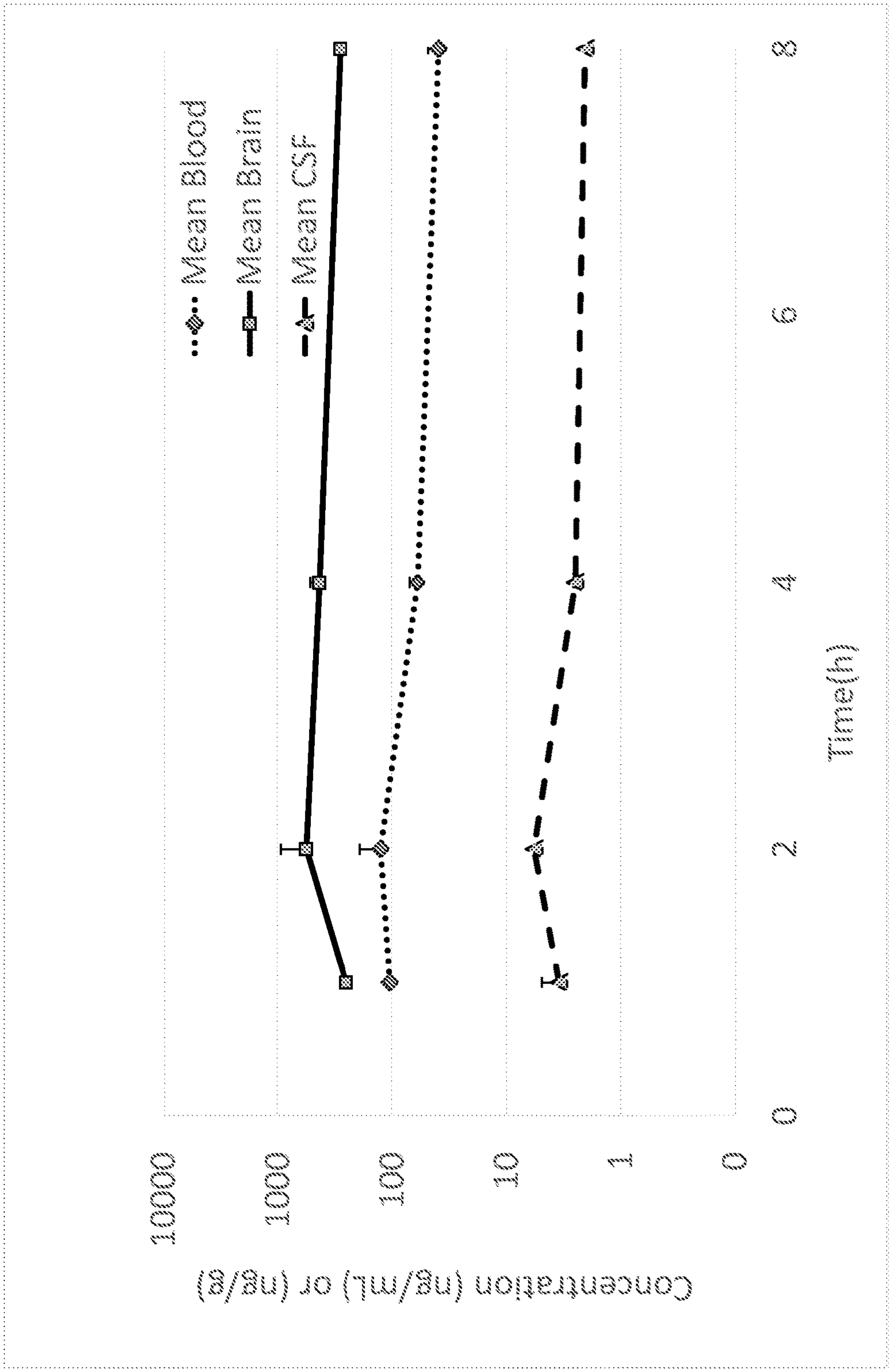
FIG. 16 is a graph showing the mean concentration of Compound No. 2B in blood, brain, and in cerebrospinal fluid (CSF) in rat when administered PO at 30 mg/kg.
Figure 17:
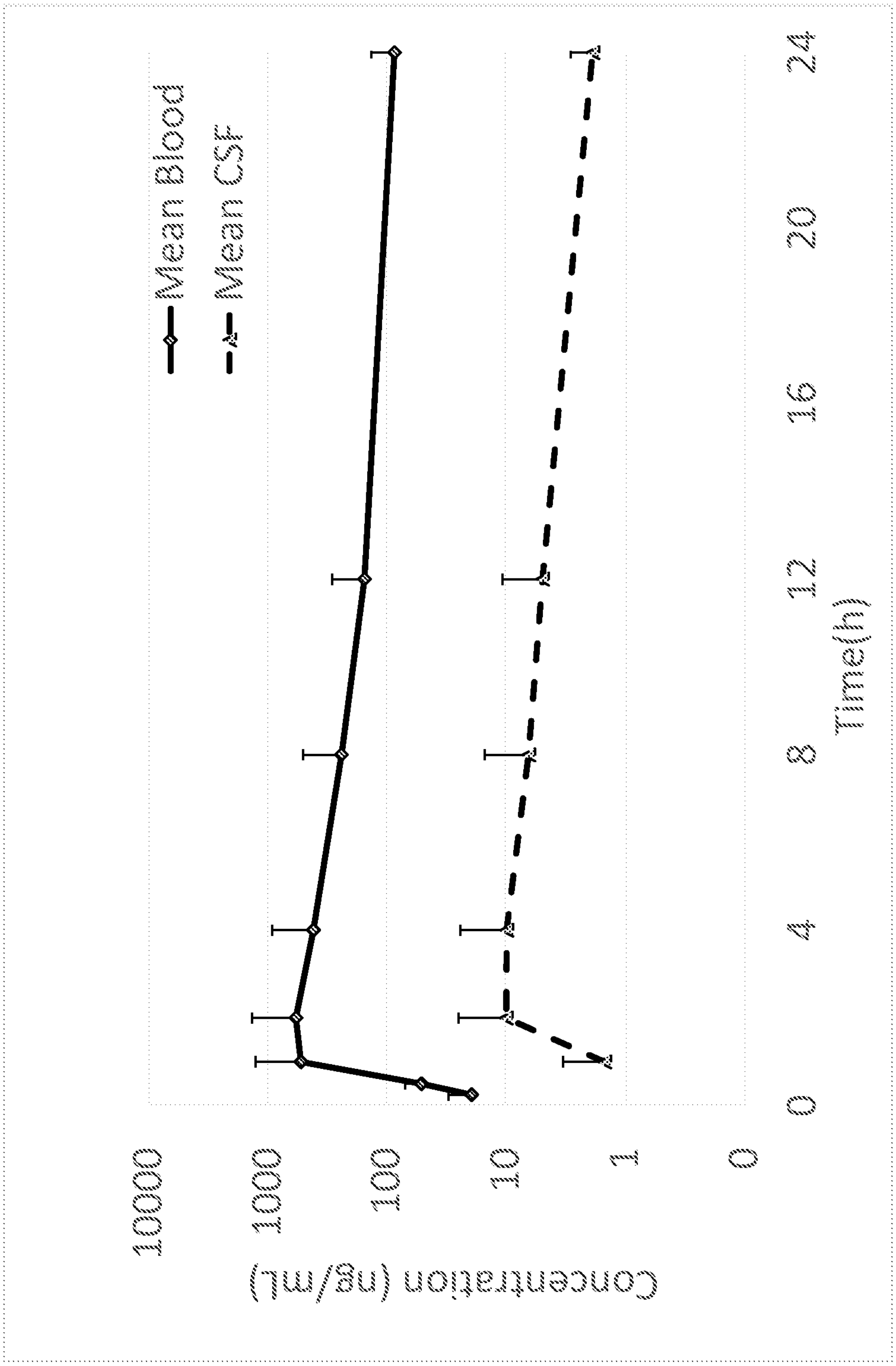
FIG. 17 is a graph showing the mean concentration of Compound No. 2B in blood and in cerebrospinal fluid (CSF) in dog when administered PO at 30 mg/kg.

Example 13. Compound No. 2B Shows Favorable Preclinical CNS PK Profiles Across Species PK parameters of were measured for PO administration of Compound No. 2B in mouse (15 mg/kg), rat (30 mg/kg), and dog (30 mg/kg). See, e.g., FIGS. 15-17. The unbound partition coefficient ($K_{puu}$) was determined to be 0.19 in the brain for mouse. The $K_{puu}$ was determined to be 0.81 in the brain and 0.90 in cerebrospinal fluid (CSF) for rat. The $K_{puu}$ was determined to be 0.22 in CSF for dog.

Example 14. Clinical Study of Compound No. 2B

This study is comprised of modules in which Compound No. 2B is be evaluated as either a single agent or in combination with other therapies for the treatment of patients with GBM or NSCLC.

Each module consists of a Dose Escalation and Dose Expansion phase. Patients are enrolled in each module are as follows:

- Module 1: GBM that has relapsed/refractory (RR) following initial surgery or NSCLC with an EGFR C797S or E18 mutation.
- Module 2: GBM in patients who are eligible for treatment with temozolomide (TMZ).
- Module 3: GBM or NSCLC with an EGFR C797S or E18 mutation eligible for surgical resection.

NSCLC patients have documented EGFR C797S or Exon 18 mutation status as confirmed by a validated NGS assay routinely used by each institution. In addition, a baseline tumor sample is provided for retrospective concordance testing by a companion diagnostic test.

Example 15. Irreversible Inhibition In Vitro with Compound No. 2B

Figure 18:
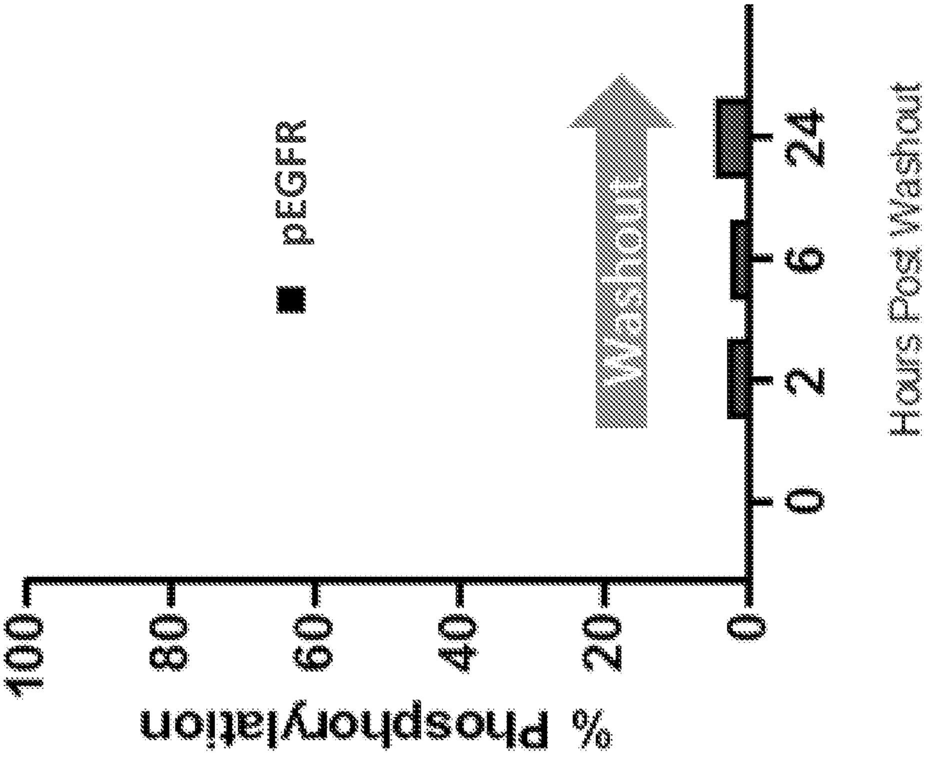
FIG. 18 is a graph showing % phosphorylation by Compound No. 2B in Ba/F3 EGFRvIII after washout.

The irreversibility of Compound No. 2B was determined in a washout study in Ba/F3 EGFRvIII. See, e.g. FIG. 18.

Figure 24:
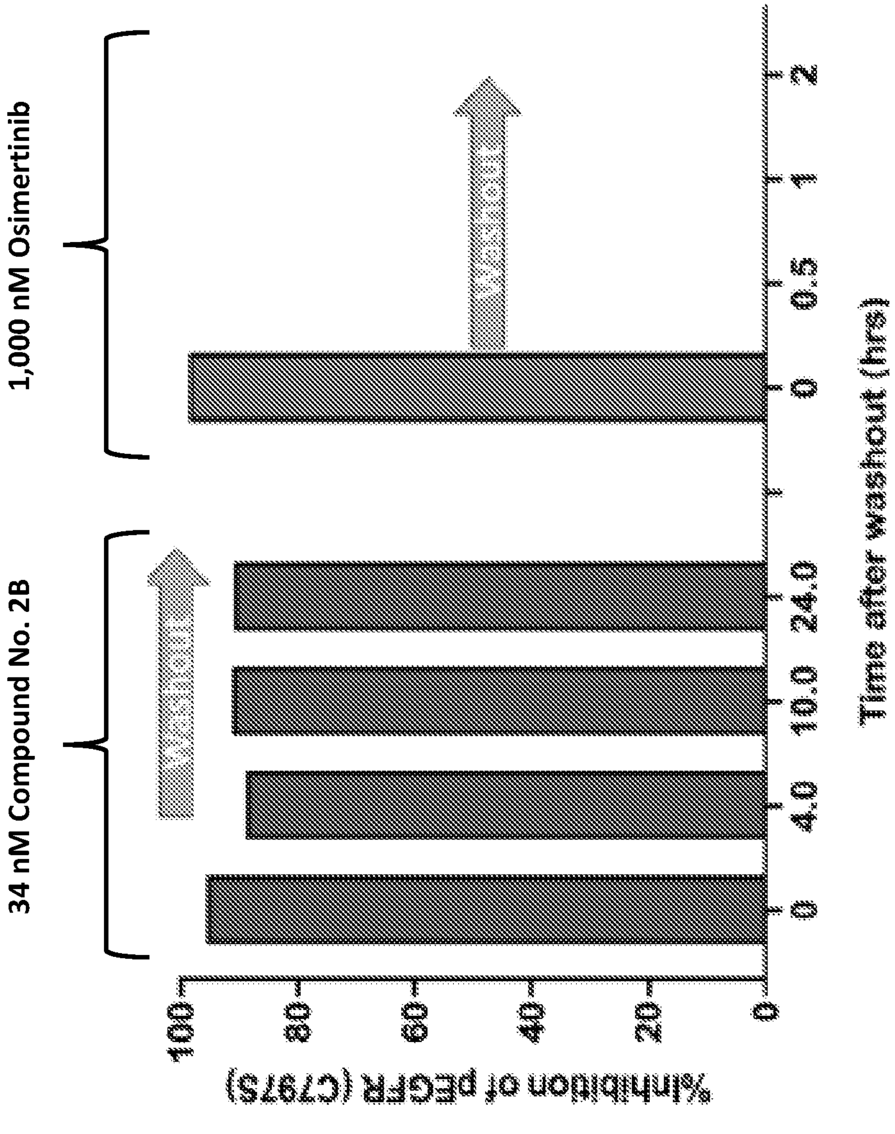
FIG. 24 is a graph showing the % inhibition of phosphorylation of the EGFR mutant protein in Ba/F3 cells expressing the EGFR Exon19del+C797S double mutation by Compound No. 2B at 34 nM and osimertinib at 1,000 nM, which shows that Compound No. 2B has >24 hours of inhibition of pEGFR Ex19/C797S.

The irreversibility of Compound No. 2B was also determined against C797S mutant, which has >24 hour inhibition of pEGFREx19/C797S at 34 nM, whereas Osimertinib at 1,000 nM shows complete washout after 0.5 hours. See, e.g., FIG. 24.

Example 16. Irreversible Inhibition In Vivo with Compound No. 1

Figure 19A:
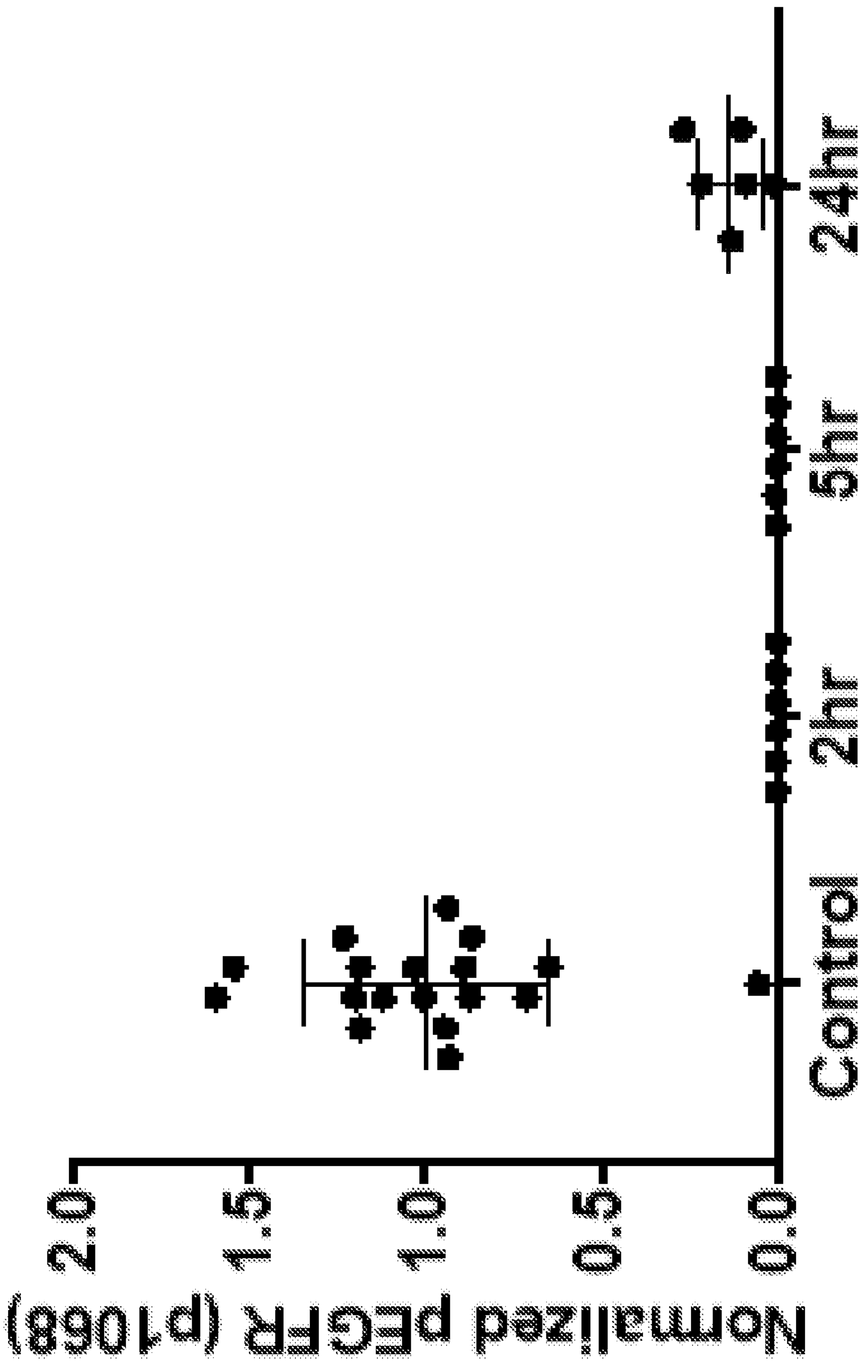
FIG. 19A is a graph showing the relationship between pEGFR (P1068) and the administration of Compound No. 1 in mice bearing BaF3 allograft tumors expressing EGFR-Viii when administered PO at 15 mg/kg.

The relationship between pEGFR (p1068) and administration of Compound No. 1 was determined in mice bearing BaF3 allograft tumors expressing EGFR-Viii. See, e.g., FIG. 19A.

Example 17. Irreversible Inhibition In Vivo with Compound No. 1A

Figure 19B:
FIG. 19B is a graph showing the relationship between pEGFR (P1068) and the administration of Compound No. 1A in mice bearing BaF3 allograft tumors expressing EGFR-Viii when administered PO at 50 mg/kg.

The relationship between pEGFR (p1068) and administration of Compound No. 1A was determined in mice bearing BaF3 allograft tumors expressing EGFR-Viii. See, e.g., FIG. 19B.

Example 18. Irreversible Inhibition In Vivo with Compound No. 2B

Figure 19C:
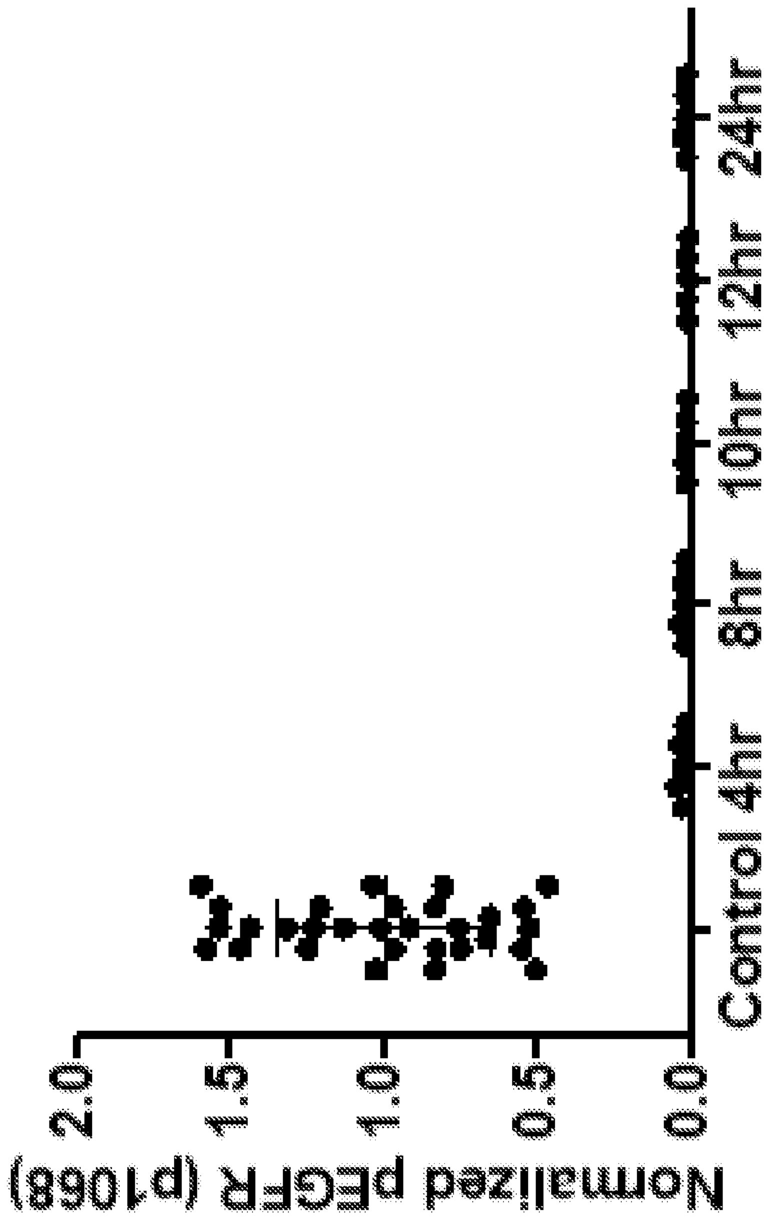
FIG. 19C is a graph showing the relationship between pEGFR (P1068) and the administration of Compound No. 2B in mice bearing Ba/F3 allograft tumors expressing EGFR-Viii when administered PO at 50 mg/kg.

The relationship between pEGFR (p1068) and administration of Compound No. 2B was determined in mice bearing BaF3 allograft tumors expressing EGFR-Viii. See, e.g., FIG. 19C.

Example 19. Tumour Growth Inhibition In Vivo with Compound No. 2B

Figure 20:
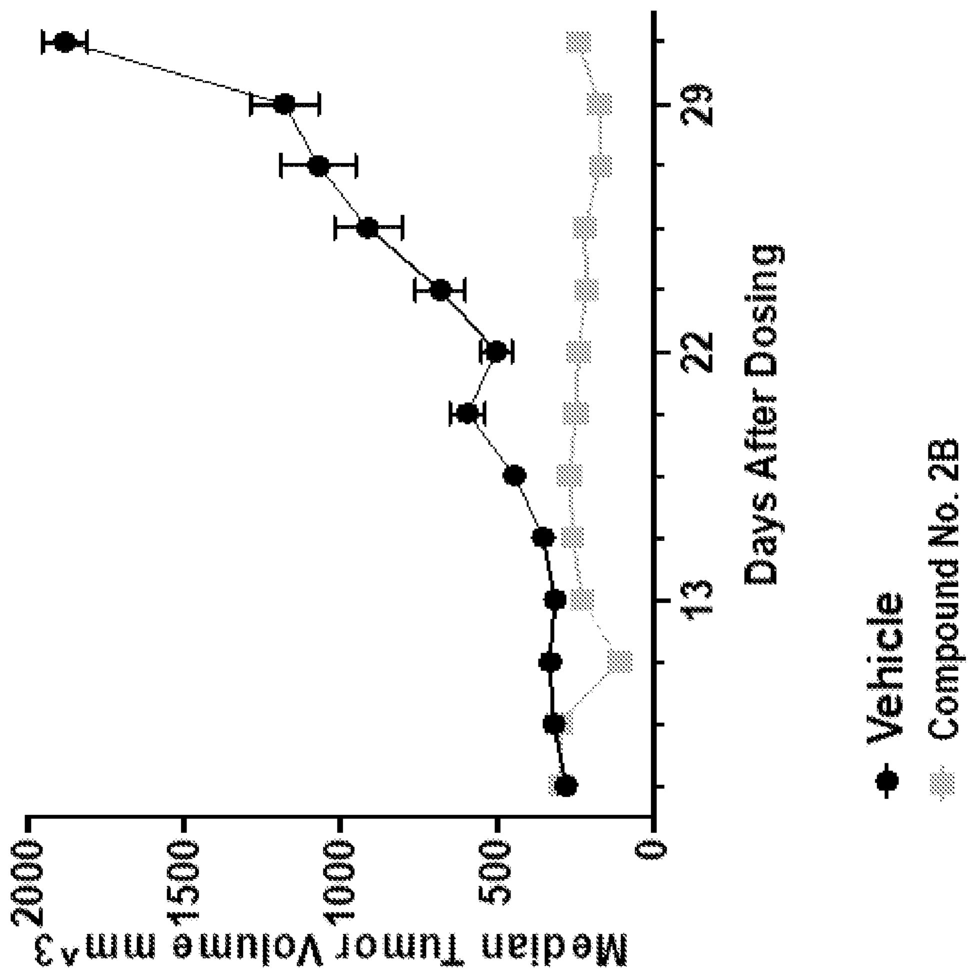
FIG. 20 is a graph showing the median tumor volume ($mm^3$) in subcutaneous GBM46 PDX expressing EGFRvII mouse models when administered Compound No. 2B at 50 mg/kg.
Figure 25:
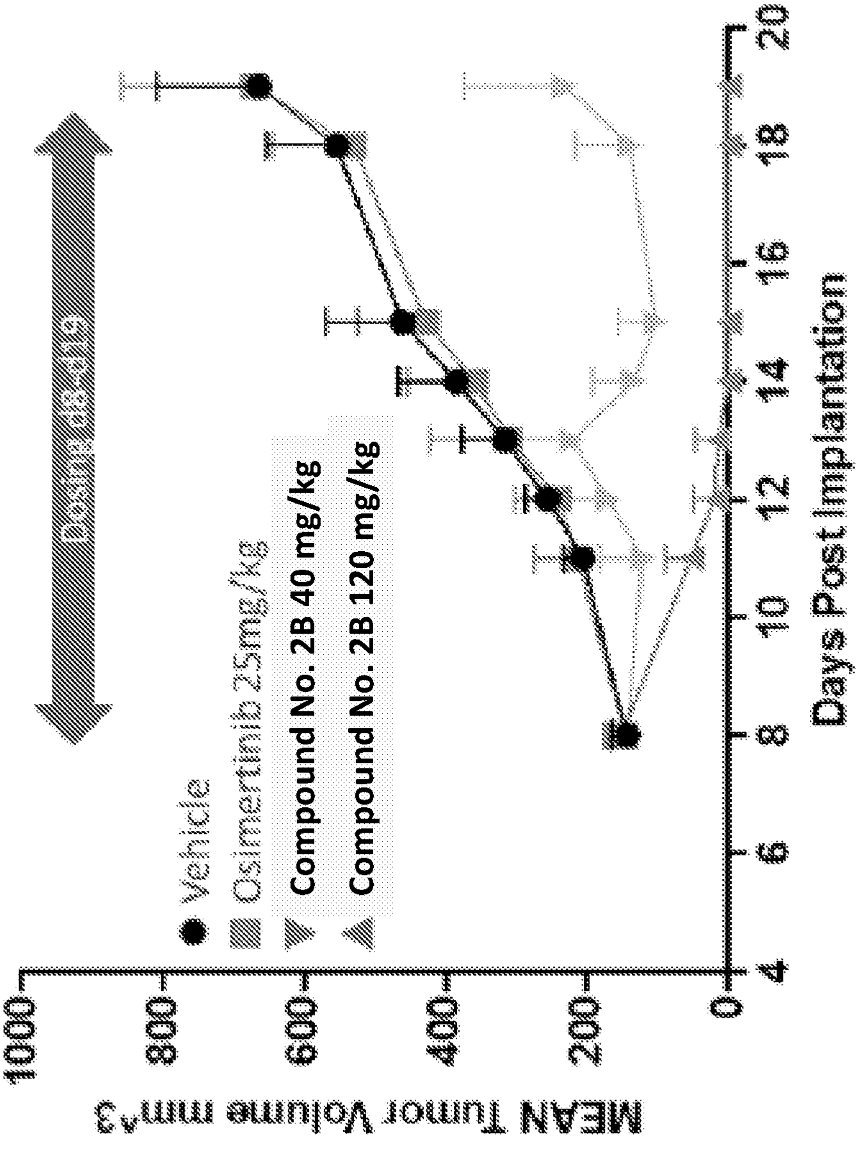
FIG. 25 is a graph showing the median tumor volume ($mm^3$) in Ba/F3-EGFR Exon19del+C797S mouse allograft models when administered a vehicle, osimertinib at 25 mg/kg, Compound No. 2B at 40 mg/kg, or Compound No. 2B at 120 mg/kg.
Figure 26:
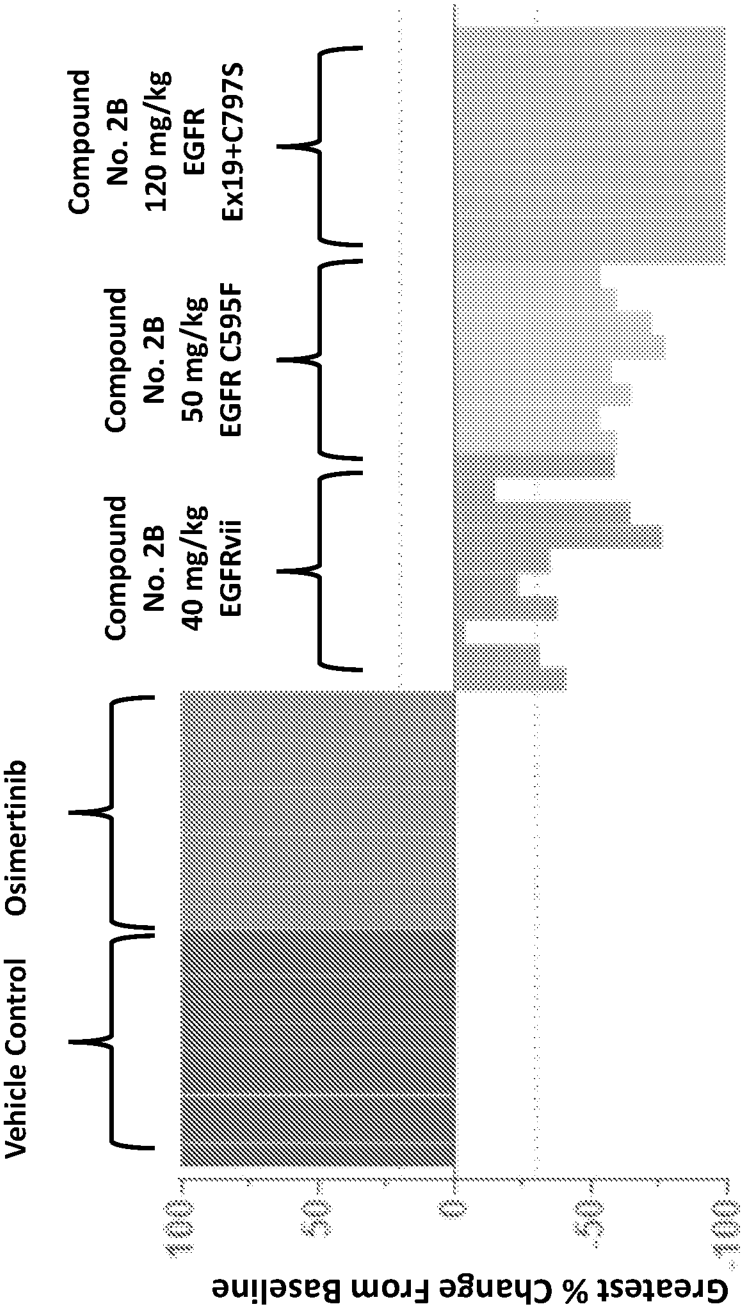
FIG. 26 is a graph showing the greatest percent change from baseline in mean tumor volume for vehicle control, osimertinib, C797S, EGFRvii, and C595F models. Vehicle control and osimertinib were tested in EGFR C797S models.

The relationship between the median tumor volume ($mm^3$) and administration of Compound No. 2B was determined in a subcutaneous GBM46 PDX expressing EGFRvII mouse model. See, e.g., FIG. 20. The relationship between the mean tumor volume ($mm^3$) and administration of Compound No. 2B was determined in Ba/F3-EGFR Exon19del+C797S mouse allograft models when administered Compound No. 2B at 40 mg/kg or at 120 mg/kg. See, e.g., FIG. 25 and FIG. 26.

Example 20. Compound No. 2B Inhibits EGFR Ex19del and Ex19del/C797S-Driven Cell Lines The ability for Compound No. 2B to selectively bind EGFR Ex19del and Ex19del/C797S-driven cell lines without sacrificing selectivity over EGFR WT is shown in Table C below. Compound No. 2B is an irreversible EGFR inhibitor that is selective for EGFR Ex19del and Ex19del/C797S over EGFR WT. The data presented in Table C are approximate and subject to experimental and instrumental variations.

TABLE C

| | Erlotinib | Gefitinib | Afatinib | Dacomitinib | Osimertinib | Compound No. 2B |
|---|---|---|---|---|---|---|
| MOA | Reversible | Reversible | Irreversible | Irreversible | Irreversible | Irreversible |
| CNS Kpuu (r) | 0.08 | 0.29 | — | 0.21 | 0.29 | 0.45 |
| EGFR-WT (H292) $IC_{50}$ (nM) | 878 | 418 | 29 | 28 | 454 | 119 |
| EGFR Ex19del (Ba/F3) $IC_{50}$ (nM) | 19 | 10 | 0.5 | 0.3 | 2.5 | 0.6 |
| EGFR Ex19del/C797S (Ba/F3) $IC_{50}$ (nM) | 15 | 11 | 8 | 9 | >1000 | 3.1 |

Example 21. Bodyweight is Unimpacted with Compound No. 2B

Figure 21:
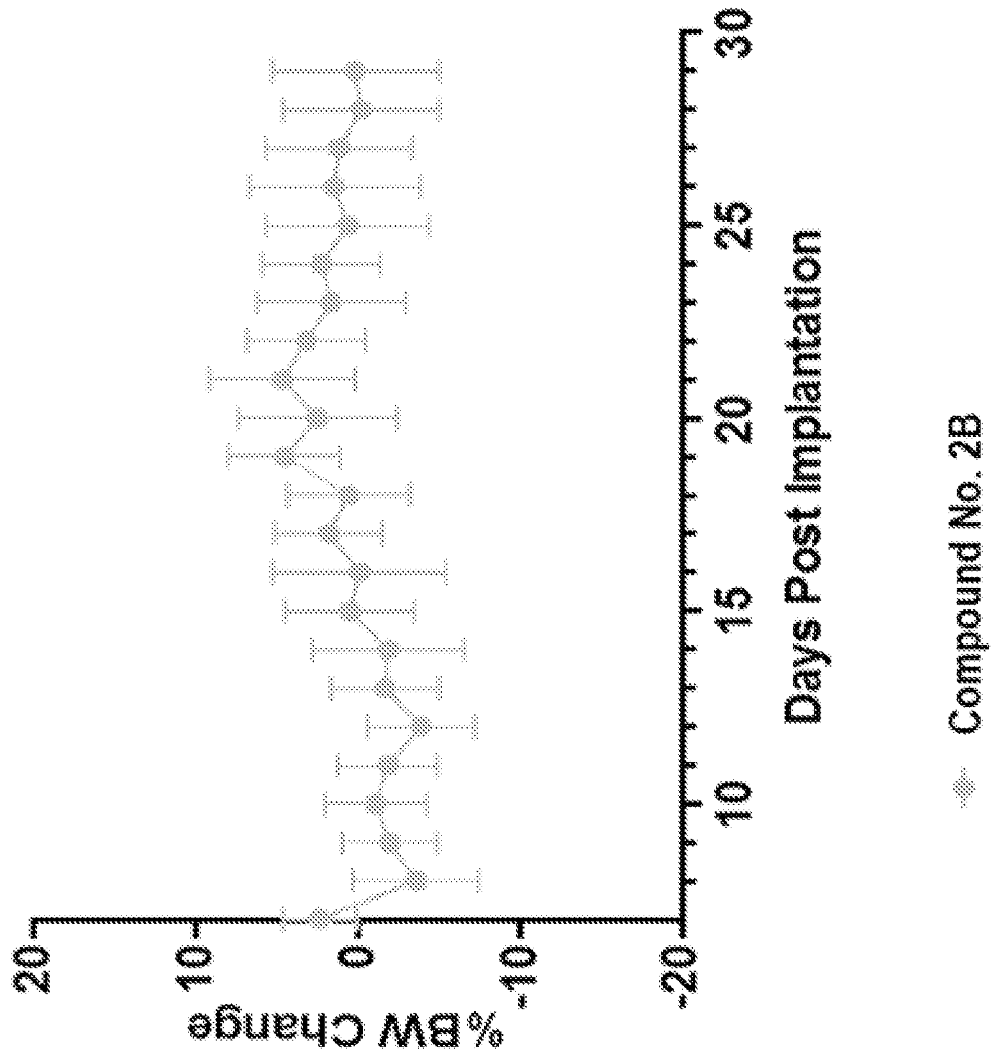
FIG. 21 is a graph showing the % body weight (BW) change in a subcutaneous GBM46 PDX expressing EGFRvII mouse model when administered Compound No. 2B at 50 mg/kg.

The relationship between the % bodyweight and administration of Compound No. 2B was determined in a subcutaneous GBM46 PDX expressing EGFRvII mouse model. See, e.g., FIG. 21.

Dose Escalation

Within each module, patients are initially enrolled in a Dose Escalation stage.

All modules use a Bayesian optimal interval (BOIN) dose escalation design using dose levels of 400 mg, 600 mg, 800 mg, and 1000 mg QD (n=7 for each dose level).

In Module 1 only, the dose escalation of Compound No. 2B initially starts as an accelerated titration of 25 mg, 50 mg, and 100 mg QD (n=1 for each dose). Potential doses are explored using the BOIN design include 200 mg, 400 mg, 600 mg, and 800 mg QD as well as 200 mg, 300 mg, 400 mg, and 500 mg BID dose levels.

In addition, 12 patients in Module 1 participate in a food or enzyme-inducing antiepileptic drug (EIAD) drug-drug interaction (DDI) evaluation (n=12 per treatment) using either a dose regimen of either 400 mg or 600 mg QD.

To evaluate the pharmacodynamic effect of Compound No. 2B in backfilled pharmacodynamic (PDc) cohorts (n=3), select GBM patients are enrolled in Module 1.

For Modules 2 and 3, three dose levels may be explored with the first dose being 1 dose level lower than the RP2D determined for Module 1.

The primary objective of the Dose Escalation stage of each Module is to identify the MTD of Compound No. 2B as a single agent or combination therapy and determine RP2D for single agent or combination agent. The safety and PK profile of Compound No. 2B are reviewed to determine whether the Dose Expansion phase of the module should be initiated, and if so, recommend an MTD.

Dose Expansion

The Dose Expansion stage assess the antitumor effect of Compound No. 2B single or combination therapy at the RP2D. The cohorts that are evaluated in each module are provided below.

- Module 1: GBM patients that has relapsed/refractory (RR) disease following initial tumor resection; and NSCLC patients with an EGFR C797S or exon 18 mutation for whom standard therapy is either not available or not appropriate.
- Module 2: GBM in patients who are eligible for treatment with temozolomide (TMZ).
- Module 3: Newly diagnosed GBM (prior to initial tumor resection); and NSCLC with an EGFR C797S or E18 mutation Study Treatment Compound No. 2B is administered orally in 21-day treatment cycles. Depending on the results of the food effect evaluation portion of Module 1 Dose Escalation stage, Compound No. 2B may be administered with food.

Study treatment continues until disease progression (PD), unacceptable drug-related toxicity, death, the start of new anticancer therapy, consent withdrawal, or are lost to follow up. Study treatment is discontinued 52 weeks after the last patient first study visit unless the patient is tolerating the study drug and deriving clinical benefit. Study treatment is discontinued in patients who have confirmed PD or who start a subsequent anticancer therapy.

Patients who complete the initial cycle of therapy without evidence of significant toxicity or clinical evidence of progressive disease) may receive additional 21-day cycles of treatment at the same dose level.

Study Assessments

Patients are required to attend clinic visits during the treatment and post-treatment periods for collection of study assessments.

Tumor imaging is performed once every 6 weeks for 1st 8 cycles and once every 12 weeks thereafter, with the tumor response assessed using RECIST, version 1.1 or by RANO, as appropriate.

Safety and tolerability are assessed through the reporting of adverse events (AEs); clinical laboratory tests; and electrocardiogram (ECG), echocardiogram (or MUGA), and physical exam findings. Dose-limiting toxicities are assessed using the NCI CTCAE, version 5.0. Pharmacokinetic sampling is collected on Days 1 and 15 of Cycle 1 and Day 1 of each subsequent cycle.

Exploratory biomarker assessments are performed on plasma ctDNA samples collected once each treatment cycle. In GBM patients, assessments are performed on CSF ctDNA collected at baseline and EOT.

Study Drug/Treatment Groups, Dose, and Mode of Administration

Patients receive the following treatments in the respective modules:

- Module 1: Single-agent Compound No. 2B
- Module 2: Compound No. 2B in combination with temozolimide
- Module 3: Compound No. 2B either as single agent or combination therapy Compound No. 2B is administered orally.

Duration of Treatment/Study:

Each patient continues study treatment until progressive disease (PD), death, or discontinuation based on the patient's or Investigator's decision. The expected duration of treatment for each patient is 6 months.

The overall duration of the study is approximately 4 years.

Example 22. Clinical Study of Compound No. 2B

Figure 27:
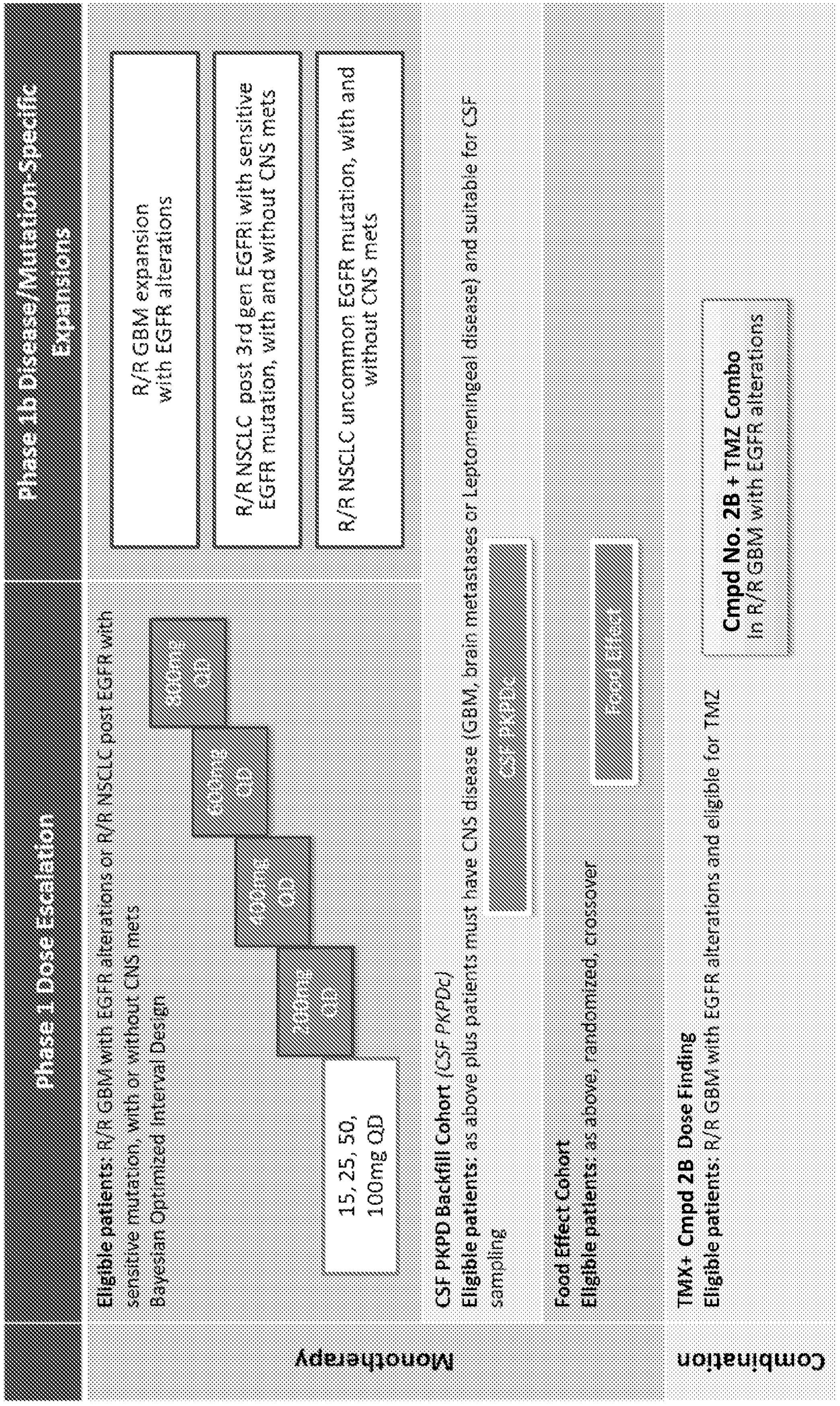
FIG. 27 is a graph depicting the schema of an exemplary study of Compound No. 2B.

A Phase 1, open-label, multicenter study of Compound No. 2B in patients with recurrent GBM harboring EGFR alterations or locally advanced or metastatic NSCLC with specific EGFR mutations was performed. The study schema is shown in FIG. 27.

The monotherapy dose escalation portion of this study evaluates Compound No. 2B in patients with either recurrent GBM expressing EGFR alterations or advanced/metastatic NSCLC harboring sensitive EGFR mutations, with or without CNS disease. The phase 1 study also includes a pilot food effect cohort as well as a leptomeningeal disease (LIVID) cohort to further assess CNS drug penetration and target related changes or ctDNA in CSF of patients with leptomeningeal disease. Once a provisional RP2D is established based on safety, PK, PDx, and tolerability data, Compound No. 2B monotherapy is explored in disease specific to further evaluate safety, PK, and preliminary assessment of efficacy. The disease specific expansions include: 1) patents with GBM with EGFR mutations and other variants, and 2) patents with advanced/metastatic NSCLC with uncommon mutations such as G719S or acquired mutations such as C797S. Once monotherapy safety is established, Compound No. 2B is administered in combination with TMZ to assess safety, tolerability, and recommended combination dose for the treatment of patients with recurrent GBM harboring EGFR mutations or variants.

Monotherapy Dose Escalation

The maximum tolerated dose (MTD) of Compound No. 2B as monotherapy is estimated using accelerated titration followed by a Bayesian optimal interval (BOIN) design. The starting dose is 15 mg once daily oral dosing. Initial dose escalation is proposed as an accelerated titration with single patient cohorts at 15 mg, 25 mg, 50 mg, and 100 mg once daily (QD) in order to minimize the number of patients receiving potentially subtherapeutic dose levels.

Multi-patient dose cohorts begin at 200 mg QD or at earlier dose levels if grade 2 or higher drug-related adverse events are observed. Additional incremental doses are explored using the BOIN design to identify an MTD. The prespecified dose levels include 200 mg, 400 mg, 600 mg, and 800 mg QD. Further expansion of previously enrolled dose levels and assessment of intermediate dose levels are conducted to further evaluate the safety, PK, preliminary efficacy, and PDx activity of Compound No. 2B.

Leptomeningeal Disease (LMD) Cohort

The LMD cohort allows patients with leptomeningeal disease to receive Compound No. 2B treatment at dose levels identified as tolerable in the monotherapy dose escalation (in patients without LIVID). CSF sampling is utilized to follow CSF malignant cell count in patients with LMD and enable assessment of study drug PK in the CSF as well as target-specific changes in malignant cells or ctDNA. The LIVID cohort open for enrollment only after a monotherapy multi-patient dose level is deemed tolerable by the SRC. LMD patients receive daily dosing of Compound No. 2B and assessments as per the monotherapy dose escalation.

Pilot Food Effect (FE) Cohort

A pilot FE cohort is evaluated to gain preliminary information about the effect of food on the PK of Compound No. 2B. Patients are be dosed in the fed/fasted state. PK is be obtained at 200 mg QD or a different dose as based on emerging PK and safety data. A dose level is not be tested in the FE cohort unless at least one dose level above it has been deemed tolerable in the monotherapy dose expansion cohorts. If data from high-fat FE indicates, the effect of a low-fat meal on the PK of Compound No. 2B is assessed as part of this cohort.

Dose Expansion Cohorts

Once the RP2D is provisionally established in the monotherapy dose escalation, confirmation of the RP2D and assessment of the preliminary efficacy are followed in disease specific expansion cohorts. Dose expansion enrolls patients in the following disease specific cohorts:

- Recurrent GBM with confirmed EGFR alterations
- Locally Advanced or Metastatic NSCLC with an acquired resistance EGFR mutation (C797S) following 3rd generation EGFR inhibitor (eg osimertinib) in the 1st line setting and platinum standard of care therapy, with and without CNS metastases.
- Locally advanced or metastatic NSCLC with oncogenic uncommon EGFR mutations (G719A/C/D/R/S, S768I, V769L, E709G/A, D716Y or other mutations validated by the Sponsor) which have progressed following EGFR inhibitor and platinum standard of care therapies, with and without CNS metastases.

A single RP2D is anticipated from dose escalations across both GBM and NSCLC. However, if disease specific dose escalation is recommended based on emerging data, then further dose adjustments occur within specific arms of patients. The RP2D, whether overall or if disease specific as needed, is selected based on overall safety and tolerability, PK, PDx and preliminary antitumor activity.

Temozolomide (TMZ) Combination

A dose-finding evaluation is performed with Compound No. 2B in combination with TMZ in patients with recurrent GBM harboring EGFR alterations. The initial dose of Compound No. 2B begins at least one dose level lower than the preliminary RP2D identified during monotherapy dose escalation. The maximum dose of Compound No. 2B in combination with TMZ does not exceed the monotherapy MTD. TMZ is administered per standard of care, in this setting: 150 mg/$m^2$ PO on Days 1 to 5 of each cycle (28 days).

Recommendations for Compound No. 2B dose escalation or de-escalation are based on the DLTs observed during Cycle 1 of combination treatment using the BOIN design and review of the totality of safety, tolerability, and available PK on the combination. The combination MTD is defined as a dose level with at least 9 patients enrolled and de-escalation is not recommended as the next step.

Study Treatment

Compound No. 2B is administered orally daily as monotherapy in 21-day treatment cycles or in combination with TMZ in 28-day treatment cycles. Study treatment continues until disease progression (PD), unacceptable drug-related toxicity, death, the start of new anticancer therapy, consent withdrawal, or lost to follow up.

Study Assessments

Tumor imaging is collected. Tumor response is assessed using RECIST, version 1.1, or by RANO, as appropriate. Safety and tolerability are assessed through the reporting of adverse events (AEs), clinical laboratory tests, electrocardiogram (ECG), echocardiogram (or MUGA), and physical exam findings. Pharmacokinetic sampling is collected and assessed during treatment cycles. Exploratory biomarker assessments are performed on plasma ctDNA, CTC, and serum samples collected during each treatment cycle. In patients with CNS disease, assessments are performed on CSF collected.

Study Drug/Treatment Groups, Dose, and Mode of Administration

Patients receive oral daily Compound No. 2B either as a single agent or in combination with TMZ administered orally.

Doses are evaluated during the Dose Escalation portion include:

- Compound No. 2B as a single agent: 15, 25, 50, 100, 200, 400, 600, and 800 mg QD administered in the fasted state. Intermediate dose levels are evaluated depending on safety and PK.
- For the Food Effect evaluation, Compound No. 2B is dosed at least 1 dose level below what has been deemed tolerable as monotherapy and will be administered in a fasted or fed (low- or high-fat meal) state. The pre-specified nominal dose for food effect cohort is 200 mg or 400 mg of Compound No. 2B depending on the emerging safety and PK data.
- For Compound No. 2B in combination with TMZ, the initial dose of Compound No. 2B in combination with TMZ begins at least one dose level lower than the preliminary RP2D identified during monotherapy dose escalation. The maximum dose of Compound No. 2B in combination with TMZ does not exceed the monotherapy MTD. TMZ is administered per standard of care in this setting: 150 $mg/m^2$ PO on days 1 to 5 of each 28-day cycle.

The provisional RP2D dose identified from the Dose Escalation portion of study is used for the dose expansion cohorts.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The foregoing description has been presented only for the purposes of illustration and is not intended to limit the disclosure to the precise form disclosed, but by the claims appended hereto.

The invention claimed is:

1. A method of treating or preventing glioblastoma (GBM) or non-small cell lung cancer (NSCLC), or a subtype of either of the foregoing in a subject, comprising administering to the subject a compound selected from Compound No. 1 and Compound No. 2:

(Compound No. 1)

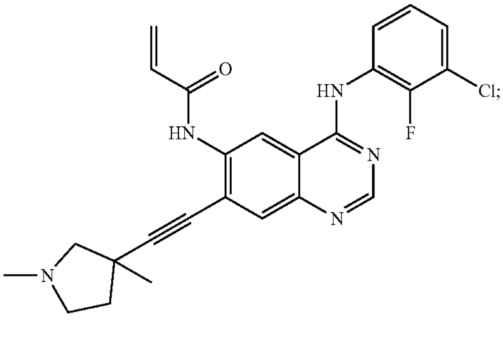

; and

-continued (Compound No. 2)

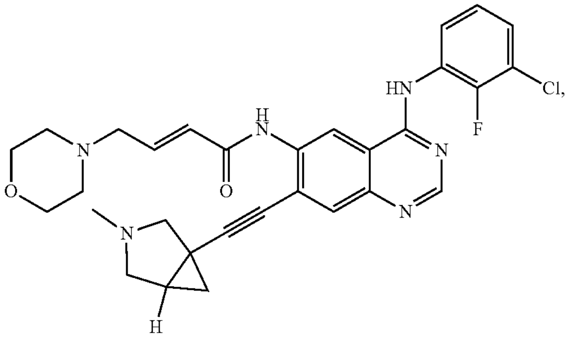

, or a stereoisomer or a pharmaceutically acceptable salt thereof, wherein the compound, or the stereoisomer thereof, is administered at a dosage of:

about 15 mg, about 25 mg, about 50 mg, about 100 mg, about 150 mg, about 200 mg, about 300 mg, about 400 mg, about 500 mg, about 600 mg, about 800 mg, or about 1000 mg.

2. The method of claim 1, wherein the GBM or NSCLC, or subtype thereof, is GBM or a subtype thereof.

3. The method of claim 1, wherein the GBM or NSCLC, or subtype thereof, is NSCLC or a subtype thereof.

4. The method of claim 1, wherein the subject has a central nervous system disease.

5. The method of claim 1, wherein the stereoisomer of Compound No. 2 is Compound No. 2A:

(Compound No. 2A)

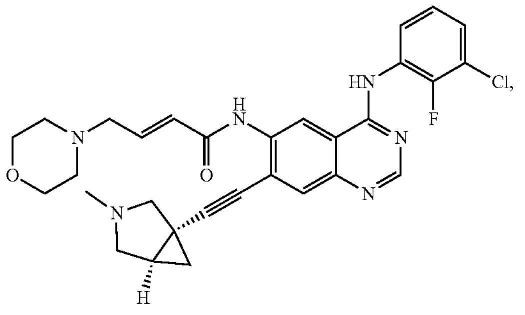

or

Compound No. 2B:

(Compound No. 2B)

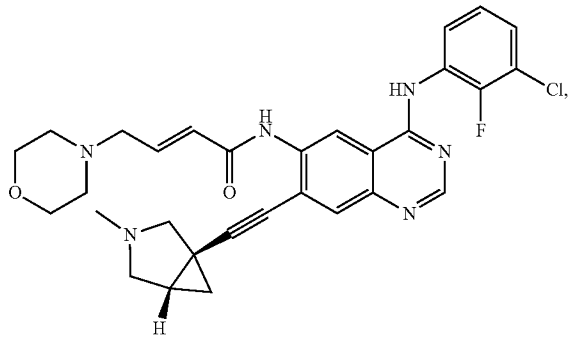

or a pharmaceutically acceptable salt thereof.

6. The method of claim 1, wherein the stereoisomer of Compound No. 2 is Compound No. 2A:

(Compound No. 2A)

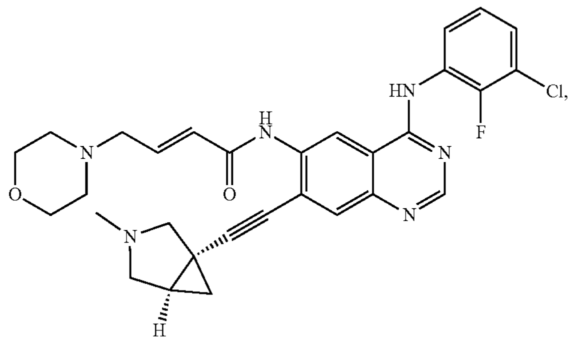

or a pharmaceutically acceptable salt thereof.

7. The method of claim 1, wherein the stereoisomer of Compound No. 2 is Compound No. 2B:

(Compound No. 2B)

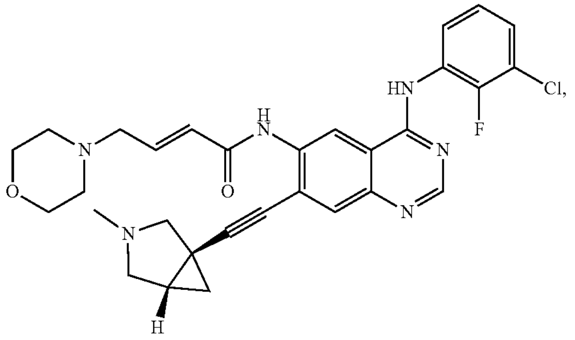

or a pharmaceutically acceptable salt thereof.

8. The method of claim 1, wherein the subject is a human.

9. The method of claim 1, wherein the compound, or the stereoisomer thereof, is administered at a dosage of about 100 mg.

10. The method of claim 1, wherein the compound, or the stereoisomer thereof, is administered at a dosage of about 150 mg.

11. The method of claim 1, wherein the compound, or the stereoisomer thereof, is administered at a dosage of about 200 mg.

12. The method of claim 1, wherein the compound, or the stereoisomer or the pharmaceutically acceptable salt thereof, is administered once daily.

13. The method of claim 1, wherein the method further comprises administering temozolomide to the subject.

14. The method of claim 1, wherein the subject has at least one EGFR mutation.

15. The method of claim 14, wherein the EGFR mutation is selected from EGFR-Vii, EGFR-A289V, EGFR-C620Y, EGFR-Viii, EGFR-A289D, EGFR-C614W, EGFR-Vvi, EGFR-H304Y, EGFR-C628F, EGFR-R222C, EGFR-G331R, EGFR-C628Y, EGFR-R252C, EGFR-P596S, EGFR-C636Y, EGFR-R252P, EGFR-P596L, EGFR-S645C, EGFR-R256Y, EGFR-P596R, EGFR-A660, EGFR-T263P, EGFR-G598V, EGFR-A768, EGFR- Y270C, EGFR-G598A, EGFR-L858R, EGFR-A289T, EGFR-G614D, EGFR-419 (deletion of Exon 19), EGFR-R108K, EGFR-V689M, EGFR-N700D, EGFR-E709K, EGFR-E709Q, EGFR- E709A, EGFR-E709G, EGFR-E709V, EGFR-S768I, EGFR-L718Q, EGFR-G719A, EGFR- G719S, EGFR-G724S, EGFR-L858R+C797S, EGFR-A19 +C797S, EGFR-C231F, EGFR- C595S, EGFR-G719C, EGFR-G719D, EGFR-G719R, EGFR-A19+C797S+T790M, EGFR- C797S, EGFR-E746-A750del+C797S, EGFR-E746-A750del, EGFR-E746- A750del+C797S+T790M, EGFR-E746-A750del+S768I, EGFR-A19+S768I, EGFR-G791S, EGFR-G719C+S768I, and EGFR-D716Y, or a combination thereof.

16. The method of claim 14, wherein the EGFR mutation is EGFR-Viii.

17. The method of claim 2, wherein the GBM is unmethylated GBM.

18. The method of claim 2, wherein the GBM is characterized by overexpression of EGFR.

19. The method of claim 3, wherein the cancer is advanced or metastatic.

20. The method of claim 3, wherein the NSCLC has metastasized to cerebrospinal fluid or to the brain.

* * * * *